US009345702B2

(12) United States Patent
Elmore et al.

(10) Patent No.: US 9,345,702 B2
(45) Date of Patent: May 24, 2016

(54) METHODS OF TREATMENT USING SELECTIVE BCL-2 INHIBITORS

(71) Applicant: AbbVie Inc., North Chicago, IL (US)

(72) Inventors: Steven Elmore, Northbrook, IL (US);
Andrew Souers, Evanston, IL (US);
Lichun Wang, North Grafton, MA (US);
Tariq Ghayur, Holliston, MA (US);
Stuart J. Perper, Bellingham, MA (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 14/535,070

(22) Filed: Nov. 6, 2014

(65) Prior Publication Data

US 2015/0150870 A1 Jun. 4, 2015

Related U.S. Application Data

(63) Continuation of application No. 13/301,898, filed on Nov. 22, 2011, now abandoned.

(60) Provisional application No. 61/416,689, filed on Nov. 23, 2010.

(51) Int. Cl.
*A61K 31/496* (2006.01)
*A61K 31/5377* (2006.01)

(52) U.S. Cl.
CPC ........... *A61K 31/496* (2013.01); *A61K 31/5377* (2013.01)

(58) Field of Classification Search
CPC .................................................. A61K 31/496
See application file for complete search history.

(56) References Cited

U.S. PATENT DOCUMENTS

| | | | |
|---|---|---|---|
| 6,004,973 A | 12/1999 | Guitard et al. |
| 6,720,338 B2 | 4/2004 | Augeri et al. |
| 6,787,534 B2 | 9/2004 | Haneda et al. |
| 6,858,638 B2 | 2/2005 | Damour et al. |
| 7,390,799 B2 | 6/2008 | Bruncko et al. |
| 7,504,512 B2 | 3/2009 | Augeri et al. |
| 7,511,013 B2 | 3/2009 | Molino et al. |
| 7,514,068 B2 | 4/2009 | Tung |
| 7,521,421 B2 | 4/2009 | Naicker et al. |
| 7,528,131 B2 | 5/2009 | Persichetti et al. |
| 7,531,685 B2 | 5/2009 | Czarnik |
| 7,534,814 B2 | 5/2009 | Ascher et al. |
| 7,538,189 B2 | 5/2009 | Naicker et al. |
| 7,642,260 B2 | 1/2010 | Bruncko et al. |
| 7,709,467 B2 | 5/2010 | Bruncko et al. |
| 7,754,886 B2 | 7/2010 | Augeri et al. |
| 7,767,684 B2 | 8/2010 | Bruncko et al. |
| 8,084,607 B2 | 12/2011 | Bruncko et al. |
| 8,173,811 B2 | 5/2012 | Bruncko et al. |
| 8,187,836 B2 | 5/2012 | Hsieh |
| 8,354,404 B2 | 1/2013 | Bruncko et al. |
| 8,546,399 B2 | 10/2013 | Bruncko et al. |
| 2002/0055631 A1 | 5/2002 | Augeri et al. |
| 2003/0144507 A1 | 7/2003 | Haneda et al. |
| 2003/0236236 A1 | 12/2003 | Chen et al. |
| 2005/0059722 A1 | 3/2005 | Damour et al. |
| 2005/0101628 A1 | 5/2005 | Jiao et al. |
| 2005/0159427 A1 | 7/2005 | Bruncko et al. |
| 2005/0163835 A1 | 7/2005 | Gellert et al. |
| 2005/0208082 A1 | 9/2005 | Papas et al. |
| 2006/0128706 A1 | 6/2006 | Bruncko et al. |
| 2007/0015787 A1 | 1/2007 | Bruncko et al. |
| 2007/0027135 A1 | 2/2007 | Bruncko et al. |
| 2007/0072860 A1 | 3/2007 | Bruncko et al. |
| 2007/0202077 A1 | 8/2007 | Brodsky et al. |
| 2008/0076779 A1 | 3/2008 | Elmore et al. |
| 2008/0182845 A1 | 7/2008 | Bardwell et al. |
| 2008/0300267 A1 | 12/2008 | Okram et al. |
| 2009/0082471 A1 | 3/2009 | Czarnik |
| 2009/0088416 A1 | 4/2009 | Czarnik |
| 2009/0093422 A1 | 4/2009 | Tung et al. |
| 2009/0105147 A1 | 4/2009 | Masse |
| 2009/0105307 A1 | 4/2009 | Galley et al. |
| 2009/0105338 A1 | 4/2009 | Czarnik |
| 2009/0111840 A1 | 4/2009 | Herold et al. |
| 2009/0118238 A1 | 5/2009 | Czarnik |
| 2009/0131363 A1 | 5/2009 | Harbeson |
| 2009/0131485 A1 | 5/2009 | Liu et al. |
| 2009/0137457 A1 | 5/2009 | Harbeson |
| 2009/0176785 A1 | 7/2009 | Bardwell et al. |
| 2009/0239259 A1 | 9/2009 | Hsieh |

(Continued)

FOREIGN PATENT DOCUMENTS

CN 1561201 A 1/2005
CN 101175738 A 5/2008

(Continued)

OTHER PUBLICATIONS

Bardwell, P.D., et al., 2009, "The Bcl-2 family antagonist ABT-737 significantly inhibits multiple animal models of autoimmunity," J. Immunol. 182(12): 7482-9.
Becker D.P., et al., "Azaadamantane Benzamide 5-HT4 Agonists: Gastrointestinal Prokinetic SC-54750" Bioorganic and Medicinal Chemistry Letters, 2004, vol. 14 (22), pp. 5509-5512.
Berge, S.M., et al., "Pharmaceutical Salts," Journal of Pharmaceutical Sciences, 1977, vol. 66 (1), pp. 1-19.
Beylot, M., et al., "In Vivo Studies of Intrahepatic Metabolic Pathways," Diabetes Metabolism, 1997, vol. 23 (3), pp. 251-257.
Blagojevic, N., et al., "Role of heavy water in Boron Neutron Capture Therapy," Topics in Dosimetry & Treatment Planning for Neutron Capture Therapy, 1994, pp. 125-134.
Blake, M. I., et al., "Studies With Deuterated Drugs," Journal of Pharmaceutical Sciences, 1975, vol. 64 (3), pp. 367-391.

(Continued)

*Primary Examiner* — Paul Zarek

(57) ABSTRACT

This invention pertains to methods of treating systemic lupus erythematosus and Sjogren's Syndrome with compounds that selectively inhibit the activity of Bcl-2 anti-apoptotic proteins. Specifically, the current invention is directed to treatment with compounds that selectively inhibit the activity of Bcl-2 proteins, with a lesser affinity for inhibiting the activity of other BCL-2 family proteins, including Bcl-$x_L$.

12 Claims, 14 Drawing Sheets

(56) References Cited

U.S. PATENT DOCUMENTS

| | | |
|---|---|---|
| 2010/0022773 A1 | 1/2010 | Bruncko et al. |
| 2010/0152183 A1 | 6/2010 | Bruncko et al. |
| 2010/0160322 A1 | 6/2010 | Bruncko et al. |
| 2010/0184750 A1 | 7/2010 | Hexamer et al. |
| 2010/0184766 A1 | 7/2010 | Kunzer et al. |
| 2010/0227838 A1 | 9/2010 | Shah et al. |
| 2010/0297194 A1 | 11/2010 | Catron et al. |
| 2010/0298321 A1 | 11/2010 | Bruncko et al. |
| 2010/0298323 A1 | 11/2010 | Bruncko et al. |
| 2010/0305122 A1 | 12/2010 | Bruncko et al. |
| 2010/0310648 A1 | 12/2010 | Packhaeuser et al. |
| 2011/0124628 A1 | 5/2011 | Bruncko et al. |
| 2012/0108590 A1 | 5/2012 | Birtalan et al. |
| 2012/0129853 A1 | 5/2012 | Elmore et al. |
| 2012/0157470 A1 | 6/2012 | Catron et al. |
| 2012/0190688 A1 | 7/2012 | Bruncko et al. |
| 2012/0277210 A1 | 11/2012 | Catron et al. |

FOREIGN PATENT DOCUMENTS

| | | |
|---|---|---|
| EP | 1880715 A1 | 1/2008 |
| EP | 1796642 B1 | 5/2008 |
| RU | 2159107 C2 | 11/2000 |
| RU | 2001103044 | 8/2003 |
| RU | 2239631 | 11/2004 |
| RU | 2239631 C2 | 11/2004 |
| RU | 2004130280 | 6/2005 |
| RU | 2004130280 A | 6/2005 |
| RU | 2318518 C2 | 3/2008 |
| RU | 2387653 | 4/2010 |
| RU | 2387653 C2 | 4/2010 |
| WO | 9507271 A1 | 3/1995 |
| WO | WO 9507271 | 3/1995 |
| WO | 9710223 A1 | 3/1997 |
| WO | WO 9710223 | 3/1997 |
| WO | 9729131 A1 | 8/1997 |
| WO | WO 9729131 | 8/1997 |
| WO | 0001389 A1 | 1/2000 |
| WO | WO 0001389 | 1/2000 |
| WO | 0057854 A2 | 10/2000 |
| WO | 0100175 A1 | 1/2001 |
| WO | 0224636 A2 | 3/2002 |
| WO | 02066470 A1 | 8/2002 |
| WO | WO 02066470 | 8/2002 |
| WO | 02098848 A1 | 12/2002 |
| WO | WO 02098848 | 12/2002 |
| WO | 03028705 A1 | 4/2003 |
| WO | 03072108 A1 | 9/2003 |
| WO | 2005049593 A2 | 6/2005 |
| WO | 2005049594 A1 | 6/2005 |
| WO | WO 2005049594 | 6/2005 |
| WO | 2005099353 A2 | 10/2005 |
| WO | WO 2005099353 | 10/2005 |
| WO | 2006008754 A1 | 1/2006 |
| WO | WO 2006008754 | 1/2006 |
| WO | WO 2006124863 | 11/2006 |
| WO | 2007002325 A1 | 1/2007 |
| WO | WO 2007002325 | 1/2007 |
| WO | 2007040650 A2 | 4/2007 |
| WO | 2006124863 A1 | 11/2007 |
| WO | 2008030836 A2 | 3/2008 |
| WO | WO 2008030836 | 3/2008 |
| WO | 2008124878 A1 | 10/2008 |
| WO | 2009045464 A1 | 4/2009 |
| WO | 2009045564 A1 | 4/2009 |
| WO | WO 2009045464 | 4/2009 |
| WO | 2009073835 A1 | 6/2009 |
| WO | 2010041051 A1 | 4/2010 |
| WO | 2010065824 A2 | 6/2010 |
| WO | 2010065865 A2 | 6/2010 |
| WO | WO 2010065824 | 6/2010 |
| WO | WO 2010065865 | 6/2010 |
| WO | 2010072734 A2 | 7/2010 |
| WO | 2010077740 A2 | 7/2010 |
| WO | 2010083441 A2 | 7/2010 |
| WO | WO 2010072734 | 7/2010 |
| WO | WO 2010077740 | 7/2010 |
| WO | WO 2010083441 | 7/2010 |
| WO | 2010138588 A2 | 12/2010 |
| WO | 2010143074 A2 | 12/2010 |
| WO | WO 2010138588 | 12/2010 |
| WO | WO 2012071336 | 5/2011 |
| WO | 2011068560 A1 | 6/2011 |
| WO | 2011068561 A1 | 6/2011 |
| WO | WO 2011068560 | 6/2011 |
| WO | WO 2011068561 | 6/2011 |
| WO | 2011149492 A1 | 12/2011 |
| WO | 2011150016 A1 | 12/2011 |
| WO | WO 2011149492 | 12/2011 |
| WO | 2012058392 A1 | 5/2012 |
| WO | 2012071336 A1 | 5/2012 |
| WO | 2012071374 A1 | 5/2012 |
| WO | WO 2012058392 | 5/2012 |
| WO | WO 2012071374 | 5/2012 |
| WO | 2012121758 A1 | 9/2012 |

OTHER PUBLICATIONS

Brickner, S.J., et al., "Synthesis and Antibacterial Activity of U-100592 and U-100766, Two Oxazolidinone Antibacterial Agents for the Potential Treatment of Multidrug-Resistant Gram-Positive Bacterial Infections," Journal of Medicinal Chemistry, 1996, vol. 39 (30), pp. 673-679.

Bruncko, M., et al., "Studies Leading to Potent, Dual Inhibitors of Bcl-2 and Bcl-XL," Journal of Medicinal Chemistry, 2007, vol. 50 (4), pp. 641-662.

Caira, M.R., "Crystalline Polymorphism of Organic Compounds," 1998, vol. 198, pp. 163-208.

Cancer [Online], [retrieved on Jul. 6, 2007]. Retrieved from the internet, <URL: http://www.nlm.nih.gov/medlineplus/cancer.html>.

Cancer [Online], [retrieved on Jul. 6, 2007]. Retrieved from the internet, <UR: http://en.wikipedia.org/wiki/Cancer>.

Certo, M., et al., "Mitochondria Primed by Death Signals Determine Cellular Addiction to Antiapoptotic Bcl-2 Family Members," Cancer Cell, 2006, vol. 9 (5), pp. 351-365.

Cross, L.C., et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.

Czajka, D. M., et al., "Effect of Deuterium Oxide on the Reproductive Potential of Mice," Annals of the New York Academy of Sciences, 1960, vol. 84, pp. 770-779.

Czajka, D. M., et al., "Physiological Effects of Deuterium on Dogs," American Journal of Physiology, 1961, vol. 201 (2), pp. 357-362.

Del Gaizo Moore, V., et al., "BCL-2 Dependence and ABT-737 Sensitivity in Acute Lymphoblastic Leukemia," Blood, 2008, vol. 111 (4), pp. 2300-2309.

Durocher Y., et al., "High-Level and High-Throughput Recombinant Protein Production by Transient Transfection of Suspension-Growing Human 293-EBNA 1 Cells," Nucleic Acids Research, 2002, vol. 30 (2), pp. e9.

Eliel, E. L., et al., "Stereochemistry of Organic Compounds," 1994, pp. 119-120, 1206, John Wiley & Sons, Inc. New York. Table of Contents.

Fairhurst, A.M., et al., "Systemic IFN-Aipha Drives Kidney Nephritis in B6.Sie123 Mice," European Journal of Immunology, 2008, vol. 38 (7), pp. 1948-1960.

Foster, A. B., et al., "Deuterium Isotope Effects in the Metabolism of Drugs and Xenobiotics: Implications for Drug Design," Advances in Drug Research, 1985, vol. 14, pp. 2-36.

Gelfand, M.C., et al., "Therapeutic Studies in NZB/W Mice II. Relative Efficacy of Azathioprine, Cyclophosphamide and Methylpredisolone," Arthritis and Rheumatism, 1972, vol. 15 (3), pp. 247-252.

Golub, T.R., et al., "Molecular Classification of Cancer: Class Discovery and Class Prediction by Gene Expression Monitoring", Science (1999), vol. 286, pp. 531-537.

(56) References Cited

OTHER PUBLICATIONS

Guo, Z., et al., "Relationship between the Expresion of bcl-2. Fas/FasL and the Apoptosis of Peripheral Lymphocytes in Patients with Systemic lupus Erythematosus," Chinese Journal of Dermatology, 2001, vol. 34 (1), pp. 25 and 27.

Harada, H., et al., "Survival Factor-Induced Extracellular Signal-Regulated Kinase Phosphorylates Bim, Inhibiting Its Association with Bax and Proapoptotic Activity," Proceedings of the National Academy of Sciences, 2004, vol. 101 (43), pp. 15313-15317.

Humerickhouse, R, "Clinical Activity of the Potent and Selective Bcl-2 Inhibitor ABT-199: . . ." Syposium presentation, Apr. 9, 2013, AACR Annual Meeting (Wash. DC), pp. 1-31.

Jones, C. D., et al., "Effects of Substitutent Modification on Face Selection in Reduction," Journal of Organic Chemistry, 1998, vol. 63 (8), pp. 2758-2760.

Kato, S., et al., "Synthesis of Deuterated Mosapride Citrate," Journal of Labelled Compounds and Radiopharmaceuticals, 1995, vol. 36 (10), pp. 927-932.

Kayagaki, N., et al., "BAFF/BLyS Receptor Binds the B Cell Survival Facor BAFF Ligand through a Discrete Surface Loop and Promotes Processing of NF-kB2," Immunity, 2002, vol. 10, pp. 515-524.

Korolkovas, A., "Development of Drugs" in: Essentials of Medicinal Chemistry, Second Edition, John Wiley and Sons, 1988, pp. 53-138.

Kushner, D.J., et al., "Pharmacological uses and perspectives of heavy water and deuterated compounds," Canadian Journal of Physiology and Pharmacology, 1999, vol. 77 (2), pp. 79-88.

Kwok, S.K., et al., "Dysfunctional Interferon-a Production by Peripheral Plasmacytoid Dendritic Cells upon Toll-like Receptor-9 Stimulation in Patients with Systemic Lupus Erythrmatosus," Arthritis Research & Therapy, 2008, vol. 10 (2), pp. R29.

Lala, P.K., et al., "Role of nitric oxide in tumor progression: lessons from experimental tumors," Cancer Metastasis Rev. Mar. 1998; vol. 17(1), pp. 91-106.

Leuner, C., et al., "Improving Drug Solubility for Oral Delivery Using Solid Dispersions,"Euopean Journal of Pharmaceutics and Biopharmaceutics : Official Journal of Arbeitsgemeinschaft Fur Pharmazeutische Verfahrenstechnik E.V., 2000, vol. 50 (1), pp. 47-60.

Liao, G., "ABT-199 BH-3 Mimetic Enters Phase Ia Trial for Chronic Lymphocytic Leukemia" [Asian Scientist Magazine online], [retrieved on Aug. 12, 2011]. Retrieved from the Internet <URL: http://www.asianscientist.com/tech-pharma/abt-199-bh-3-mimetic-wehi-phase-ia-trial-chronic-lymphocytic-leukemia>.

Liu, K., et al., "What do Mouse Models Teach us about Human SLE?," Clinical Immunology, 2006, vol. 119 (2), pp. 123-130.

Lizondo, J., et al., "Linezolid: Oxazolidinone antibacterial," Drugs of the Future, 1996, vol. 21 (11), pp. 1116-1123.

Mallehsam, B., et al., "Highly Efficient Cui-Catalyzed Coupling of Aryl Bromides with Oxazolidinones using Buchwald's Protocol: A Short Route to Linezolid and Toloxatone," Organic Letters, 2003, vol. 5 (7), pp. 963-965.

Marquina, R., et al., "Inhibition of B Cell Death causes the Development of an IgA Nephropathy in (New Zealand White x C57BL/6) F(1)-bcl-2 Transgenic Mice," Journal of Immunology, 2004, vol. 172 (11), pp. 7177-7185.

Mason, K.D., et al., "Programmed anuclear cell death delimits platelet life span," Cell, 2007, vol. 128 (6), pp. 1173-1186.

Mathian, A., et al., "IFN-a induces Early Lethal Lupus in Preautoimmune (New Zealand Black x New Zealand White) F1 but not in BALB/c Mice," Journal of Immunology, 2005, vol. 174 (5), pp. 2499-2506.

Mizushima, S., et al., "pEF-BOS, a Powerful Mammalian Expression Vector," Nucleic Acids Research, 1990, vol. 18 (17), p. 5322.

Oltersdorf, T., et al., "An inhibitor of Bcl-2 family proteins induces regression of solid tumours," Nature, 2005, 435: 677-681.

Park, C.M., et al., "Discovery of an Orally Bioavailable Small Molecule Inhibitor of Prosurvival B-Cell Lymphoma 2 Proteins," Journal of Medicinal Chemistry, 2008, vol. 51 (21), pp. 6902-6915.

Ramos, M.A., et al., "Modulation of Autoantibody Production by Mycophenolate Mofetil: Effects on the Development of SLE in (NZB x NZW)F1 Mice," Nephrology Dialysis Transplantation, 2003, vol. 18 (5), p. 878-883.

Roberti, M., et al., "Synthesis and Biological Evaluation of Resveratrol and Analogues as Apoptosis-Inducing Agents," J. Med. Chem. 2003, 46, 3546-3554.

Sharma, D.K., et al., "Solubility Enhancement Strategies for Poorly Water-Soluble Drugs in Solid Dispersions: A Review," Asian Journal of Pharmecutics, 2007, vol. 1(1), pp. 9-19.

Skoug, J.W., et al., Enabling Discovery through Formulation. American Association of Pharmaceutical Scientists (AAPS) Webinar [online]. Presented Mar. 18, 2010, 12:30 PM to 2:00PM EDT. Obtained from webinar conductors.

Souers, A.J., et al., "ABT-199, a potent and selective BCL-2 inhibitor, achieves antitumor activity while sparing platelets," Nature Medicine, 2013, 19: 202-208.

Thomson, J.F., "Physiological Effects of D20 in Mammals," Annals of the New York Academy of Sciences, 1960, vol. 84, pp. 736-744.

Vandenberg, C.J. and Cory, S., "ABT-199, a new Bcl-2-specific BH3 mimetic, . . ." Blood, Prepublished online Jan. 22, 2013; doi:1 0.1182/blood-2013-01-475855.

Wang, Z.X., "An Exact Mathematical Expression for Describing Competitive Binding of Two Different Ligands to a Protein Molecule," FEBS Letters, 1995, vol. 360 (2), pp. 111-114.

Wendt, M.D., "Discovery of ABT-263, a Bcl-Family Protein Inhibitor: Observations on Targeting a Large Protein-Protein Interaction," Expert Opinion on Drug Discovery, 2008, vol. 3 (9), pp. 1123-1143.

Wilson, L.E., et al., "Autoimmune Disease Complicating Antiviral Therapy for Hepatitis C Virus Infection," Seminars in Arthritis and Rheumatism, 2002, vol. 32(3), pp. 163-173.

Xie, M., et al., "Apoptosis and Fas/bcl-2 Expression in Peripheral Blood Lymphocytes of Patients with Systemic Lupus Erythematosus," Chinese Medical Journal, 1999, vol. 113, pp. 1072.

Zhang, H., et al., "Bcl-2 Family Proteins are Essential for Platelets Survival," cell Death and Differentiation, 2007, vol. 14 (5), pp. 943-951.

Zhang, R., et al., "Effect of Interferon-Alpha in Systemic Lupus Erthematosus (SLE) Serum on the Differentiation and Maturation of Dendritic Cells derived from CD34+ Hematopoietic Precursor Cells," Journal of Nanjing Medical University, 2009, vol. 23 (6), pp. 380-385.

International Searching Authority, Supplementary International Search Report mailed Feb. 24, 2011 f or Application No. PCT/US2009/066722, 2 pages.

International Searching Authority, Supplementary International Search Report mailed Mar. 24, 2011 for Application No. PCT/US2009/066790, 2 pages.

International Searching Authority, Supplementary International Search Report mailed Sep. 8, 2011 for Application No. PCT/US2010/036198, 2 pages.

International Searching Authority, Supplementary International Search Report mailed Jun. 28, 2012 for Application No. PCT/US2010/057587, 2 pages.

International Searching Authority, International Search Report mailed Aug. 4, 2010 for Application No. PCT/US2009/066722, 4 pages.

International Searching Authority, International Search Report mailed Jul. 28, 2010 for Application No. PCT/US2009/066790, 4 pages.

International Searching Authority, International Search Report mailed Jul. 28, 2010 for Application No. PCT/US2009/067335, 4 pages.

International Searching Authority, International Search Report mailed Jun. 17, 2010 for Application No. PCT/EP2009/067689, 4 pages.

International Searching Authority, International Search Report mailed Feb. 9, 2011 for Application No. PCT/US2010/036198, 3 pages.

International Searching Authority, International Search Report mailed Aug. 16, 2010 for Application No. PCT/US2010/036844, 3 pages.

(56) References Cited

OTHER PUBLICATIONS

International Searching Authority, International Search Report for Application No. for PCT/US2010/03619, mailed Aug. 19, 2010, 3 pages.
International Searching Authority, International Search Report for Application No. PCT/US2010/057587, mailed Apr. 28, 2011, 2 pages.
International Searching Authority, International Search Report for Application No. PCT/US2011/058024, mailed Jan. 27, 2012, 3 pages.
International Searching Authority, International Search Report for Application No. PCT/US2011/061678, mailed Feb. 3, 2012, 3 pages.
International Searching Authority, International Search Report for Application No. PCT/US2011/061769, mailed Feb. 14, 2012, 3 pages.
International Searching Authority, International Search Report for Application No. PCT/US2011/054959, mailed Dec. 16, 2011, 3 pages.
International Searching Authority, Written Opinion for Application No. PCT/US2007/077579, mailed Mar. 10, 2009, 9 pages.
International Searching Authority, Written Opinion for Application No. PCT/US2009/066722, mailed Jun. 7, 2011, 7 pages.
International Searching Authority, Written Opinion for Application No. PCT/US2010/036198 mailed Nov. 29, 2011, 7 pages.
International Searching Authority, Written Opinion for Application No. PCT/US2010/036844, mailed Jun. 5, 2012, 8 pages.
International Searching Authority, Written Opinion for Application No. PCT/US2010/036919, mailed Jun. 5, 2012, 7 pages.
Bardwell P.D., et al., "The Bcl-2 Family Antagonist ABT-737 Significantly Inhibits Multiple Animal Models of Autoimmunity," Journal of Immunology, 2009, vol. 182 (12), pp. 7482-7489.
Becker D.P., et al., "Azaadamantane Benzamide 5-HT4 Agonists: Gastrointestinal Prokinetic SC-54750," Bioorganic and Medicinal Chemistry Letters, 2004, vol. 14 (22), pp. 5509-5512.
Berge, S. M. et al., "Pharmaceutical Salts," Journal of Pharmaceutical Sciences, 1977, vol. 66 (1), pp. 1-19.
Beylot, M. et al., "In Vivo Studies of Intrahepatic Metabolic Pathways," Diabetes & Metabolism, 1997, vol. 23 (3), pp. 251-257.
Blagojevic, N. et al., "Role of Heavy Water in Boron Neutron Capture Therapy," Topics in Dosimetry & Treatment Planning for Neutron Capture Therapy, 1994, pp. 125-134.
Blake, M. I. et al., "Studies With Deuterated Drugs," Journal of Pharmaceutical Sciences, 1975, vol. 64 (3), pp. 367-391.
Brickner, S.J. et al., "Synthesis and Antibacterial Activity of U-100592 and U-100766, Two Oxazolidinone Antibacterial Agents for the Potential Treatment of Multidrug-Resistant Gram-Positive Bacterial Infections," Journal of Medicinal Chemistry, 1996, vol. 39 (3), pp. 673-679.
Bruncko, M., et al., "Studies Leading to Potent, Dual Inhibitors of Bcl-2 and Bcl-xL," Journal of Medicinal Chemistry, 2007, vol. 50 (4), pp. 641-662.
Cancer [online], [retrieved on Jul. 6, 2007]. Retrieved from the internet, <URL:http://www.nlm.nih.gov/medlineplus/cancer.html>, 8 pgs.
Cancer [online], [retrieved on Jul. 6, 2007]. Retrieved from the internet, <URL: http://en.wikipedia.org/wiki/Cancer>, 34 pgs.
Cross, L.C. et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.
Crowley, M. M., et al., "Pharmaceutical Applications of Hot-Melt Extrusion: Part 1," Drug Development and Industrial Pharmacy, 2007, vol. 33 (9), pp. 909-926.
Czajka, D. M. et al., "Effect of Deuterium Oxide on the Reproductive Potential of Mice," Annals New York Academy of Sciences, 1960, vol. 84, pp. 770-779.
Czajka, D. M. et al., "Physiological Effects of Deuterium on Dogs," American Journal of Physiology, 1961, vol. 201 (2), pp. 357-362.
Durocher Y., et al., "High-Level and High-Throughput Recombinant Protein Production by Transient Transfection of Suspension-Growing Human 293-EBNA1 Cells," Nucleic Acids Research, 2002, vol. 30 (2), pp. e9.
Eliel, E. L. et al., "Stereochemistry of Organic Compounds," 1994, John Wiley & Sons, Inc., New York. Table of Contents. 6 pgs.
Fairhurst A.M., et al., "Systemic IFN-Alpha Drives Kidney Nephritis in B6.Sle123 Mice," European Journal of Immunology, 2008, vol. 38 (7), pp. 1948-1960.
Foster, A. B. et al., "Deuterium Isotope Effects in the Metabolism of Drugs and Xenobiotics: Implications for Drug Design," Advances in Drug Research, 1985, vol. 14, pp. 2-36.
Gelfand M.C., et al., "Therapeutic Studies in NZB/W Mice II. Relative Efficacy of Azathioprine, Cyclophosphamide and Methylprednisolone," Arthritis and Rheumatism,1972, vol. 15 (3), pp. 247-252.
Guo Z., et al., "Relationship between the Expression of bc1-2. Fas/FasL and the Apoptosis of Peripheral Lymphocytes in Patients with Systemic lupus Erythematosus," Chinese Journal of Dermatology, 2001, vol. 34 (1), pp. 25 and 27.
Gupta, P. K., "Solutions and Phase Equilibria", Remington, The Science and Practice of Pharmacy, 21st Edition, Chapter 16, (2005) pp. 211-230.
Hanahan, D., et al., "The Hallmarks of Cancer," Cell, 2000, vol. 100 (1 ), pp. 57-70.
Hoepfner, E.M., et al., eds., "Fiedler Encyclopedia of Excipients for Pharmaceuticals, Cosmetics and Related Areas," 5th Edition, Editio Cantor Verlag Aulendorf, 2002, Table of Contents, 6 pgs.
Holzelova, E. et al., "Autoimmune Lymphoproliferative Syndrome with Somatic Fas Mutations," New England Journal of Medicine, 2004, vol. 351 (14), pp. 1409-1418.
Hovorka, S. W. et al., "Oxidative Degradation of Pharmaceuticals: Theory, Mechanisms and Inhibition," J. Pharm. Sciences, 2001, vol. 90 (3), 253-269.
Humerickhouse, R, "Clinical Activity of the Potent and Selective Bcl-2 Inhibitor ABT-199: Proving the Concept," Symposium presentation, Apr. 9, 2013, AACR Annual Meeting (Wash. DC), 31 pgs.
Jones, C.D. et al., "Effects of Substituent Modification on Face Selection in Reduction," Journal of Organic Chemistry, 1998, vol. 63 (8), pp. 2758-2760.
Kato, S. et al., "Synthesis of Deuterated Mosapride Citrate," Journal of Labelled Compounds and Radiopharmaceuticals, 1995, vol. 36 (10), pp. 927-932.
Kayagaki N., et al., "BAFF/BLyS Receptor 3 Binds the B Cell Survival Factor BAFF Ligand Through a Discrete Surface Loop and Promotes Processing of NF-kB2," Immunity, 2002, vol. 10, pp. 515-524.
Kibbe, A.H., Handbook of Pharmaceutical Excipients, Third Edition, 2000, American Pharmaceutical Association, Table of Contents, 4 pgs.
Klein, C.E., et al., "The Tablet Formulation of Lopinavir/Ritonavir Provides Similar Bioavailability to the Soft-Gelatin Capsule Formulation with Less Pharmacokinetic Variability and Diminished Food Effect," Journal of Acquired Immune Deficiency Syndromes, 2007, vol. 44 (4), pp. 401-410.
Korolkovas A., "Development of Drugs" in: Essentials of Medicinal Chemistry, Second Edition, John Wiley and Sons, 1988, pp. 53-139.
Kushner, et al., "Pharmacological uses and perspectives of heavy water and deuterated compounds," Canadian Journal of Physiology and Pharmacology, 1999, vol. 77 (2), pp. 79-88.
Kwok S.K., et al., "Dysfunctional Interferon-a Production by Peripheral Plasmacytoid Dendritic Cells upon Toll-like Receptor-9 Stimulation in Patients with Systemic Lupus Erythematosus," Arthritis Research & Therapy, 2008, vol. 10 (2), 11 pgs.
Lala, P.K., et al., "Role of nitric oxide in tumor progression: Lessons from experimental tumors." Cancer and Metastasis Reviews, 1998, vol. 17(1 ), pp. 91-106.
Laurent, S.A., et al., "Synthesis of "Trioxaquantel" Derivatives as Potential New Antischistosomal Drugs," European Journal of Organic Chemistry, 2008, vol. 5, pp. 895-913.

(56) References Cited

OTHER PUBLICATIONS

Leuner, C., et al., "Improving Drug Solubility for Oral Delivery Using Solid Dispersions," European Journal of Pharmaceutics and Biopharmaceutics: Official Journal of Arbeitsgemeinschaft Fur Pharmazeutische Verfahrenstechnik E.V., 2000, vol. 50 (1), pp. 47-60.

Liao, G., "ABT-199 BH-3 Mimetic Enters Phase Ia Trial for Chronic Lymphocytic Leukemia", [Asian Scientist Magazine online], [retrieved on Aug. 12, 2011]. Retrieved from the Internet <URL:http://www.asianscientist.com/tech-pharma/abt- 199-bh-3-mimetic-wehiphase-ia-trial-chronic-lymphocytic-leukemia>, 2 pgs.

Liu K., et al., "What do Mouse Models Teach us about Human SLE?," Clinical Immunology, 2006, vol. 119 (2), pp. 123-130.

Lizondo, J. et al., "Linezolid: Oxazolidinone Antibacterial," Drugs of the Future, 1996, vol. 21 (11), pp. 1116-1123.

Mallesham, B. et al., "Highly Efficient CuI-Catalyzed Coupling of Aryl Bromides with Oxazolidinones Using Buchwald's Protocol: A Short Route to Linezolid and Toloxatone," Organic Letters, 2003, vol. 5 (7), pp. 963-965.

Marquina R., et al , "Inhibition of B Cell Death Causes the Development of an IgA Nephropathy in (New Zealand White x C57BL/6) $F_1$-bcl-2 Transgenic Mice," Journal of Immunology, 2004, vol. 172 (11), pp. 7177-7185.

Mason K.D., et al, "Programmed Anuclear Cell Death Delimits Platelet Life Span," Cell, 2007, vol. 128 (6), pp. 1173-1186.

Mathian A., et al., "IFN-a induces Early Lethal Lupus in Preautoimmune (New Zealand Black x New Zealand White) $F_1$ but not in BALB/c Mice," Journal of Immunology, 2005, vol. 174 (5), pp. 2499-2506.

Mizushima S., et al., "pEF-BOS, a Powerful Mammalian Expression Vector," Nucleic Acids Research, 1990, vol. 18 (17), pp. 5322.

Moschwitzer, J. et al., "Development of an Intravenously Injectable Chemically Stable Aqueous Omeprazole Formulation Using Nanosuspension Technology" Eur. J. Pharmaceutics and Biopharmaceutics, 58 (3), 2004, pp. 615-619.

Oltersdorf, T., et al., "An inhibitor of Bcl-2 family proteins induces regression of solid tumours," Nature, 2005, vol. 435 (2), pp. 677-681.

Puck J.M., et al., "Immune Disorders Caused by Defects in the Caspase Cascade," Current Allergy and Asthma Reports, 2003, vol. 3, pp. 378-384.

Ramos M.A., et al., "Modulation of Autoantibody Production by Mycophenolate Mofetil: Effects on the Development of Sle in (NZB x NZW)$F_1$ Mice," Nephrology Dialysis Transplantation, 2003, vol. 18 (5), pp. 878-883.

Rengan R., et al., "Actin Cytoskeletal Function is Spared, but Apoptosis is Increased, in WAS Patient Hematopoietic Cells," Blood, 2000, vol. 95 (4), pp. 1283-1292.

Roberti, M., et al., "Synthesis and Biological Evaluation of Resveratrol and Analogues as Apoptosis-Inducing Agents," J. Med. Chem. 2003, 46, 3546-3554.

Sharma, D.K, et al., "Solubility Enhancement Strategies for Poorly Water-Soluble Drugs in Solid Dispersions: A Review," Asian Journal of Pharmaceutics, 2007, vol. 1 (1), pp. 9-19.

Shimazaki K., et al., "Evaluation of Apoptosis as a Prognostic Factor in Myelodysplastic Syndromes," British Journal of Haematology, 2000, vol. 110 (3), pp. 584-590.

Skoug, J.W., et al., Enabling Discovery Through Formulation, American Association of Pharmaceutical Scientists (AAPS) Webinar [online]. Presented Mar. 18, 2010, 12:30 PM to 2:00PM EDT, 51 pgs.

Souers, Andrew J. et al, "ABT-199, a potent and selective BCL-2 inhibitor, achieves antitumor activity while sparing platelets," Nature Medicine, (2013), 9 pgs.

Sperling, L. H., "Introduction to Physical Polymer Science," Second Edition, John Wiley & Sons, Inc., 1992, Table of Contents, 18 pgs.

Sutton, V.R., et al., "Bcl-2 Prevents Apoptosis Induced by Perforin' and Granzyme B, But not that Mediated by Whole Cytotoxic Lymphocytes," Journal of Immunology, 1997, vol. 158 (12), pp. 5783-5790.

Thomson, J.F., "Physiological Effects of $D_2O$ in Mammals," Annals New York Academy of Sciences, 1960, vol. 84, pp. 736-744.

Tse, C., et al., "ABT-263: A Potent and Orally Bioavailable Bcl-2 Family Inhibitor," Cancer Research, 2008, vol. 68 (9), pp. 3421-3428—Including Supplementary Data.

U.S. Department of Health and Human Services Food and Drug Administration Center for Drug Evaluation and Research, Guidance for Industry, Aug. 2000, [retrieved on Jan. 25, 2012]. Retrieved from the internet <URL: http://www. f <la.gov / downloads/Drugs/ GuidanceComplianceRegulatorylnformation/Guidances/ ucm070246. pdf.>, 16 pgs.

Vandenberg, C.J. et al., "ABT-199, a new Bcl-2-specific BH3 mimetic, has in vivo efficacy against aggressive Myc-driven mouse lymphomas without provoking thrombocytopenia", Blood First Edition Paper, prepublished online Jan. 22, 2013; DOI 10.1182/blood-2013-01-475855, 12 pgs.

Vasanthavada, M. et al., "Development of Solid Dispersion of Poorly Water-Soluble Drugs", in Water-Insoluble Drug Formulation, Liu, R., ed., 2nd Edition, (2008), pp. 499-529.

Wendt, M.D., "Discovery of ABT-263, a Bcl-Family Protein Inhibitor: Observations on Targeting a Large Protein-Protein Interaction," Expert Opinion on Drug Discovery, 2008, vol. 3 (9), pp. 1123-1143.

Wilson L.E., et al., "Autoimmune Disease Complicating Antiviral Therapy for Hepatitis C Virus Infection," Seminars in Arthritis and Rheumatism, 2002, vol. 32 (3), pp. 163-173.

Xie M., et al., "Apoptosis and Fas/bcl-2 Expression in Peripheral Blood Lymphocytes of Patients with Systemic Lupus Erythematosus," Chinese Medical Journal, 1999, vol. 113, p. 1072.

Zhang R., et al., "Effect of Interferon-Alpha in Systemic Lupus Erthematosus (SLE) Serum on the Differentiation and Maturation of Dendritic Cells derived from CD34+Hematopoietic Precursor Cells," Journal of Nanjing Medical University, 2009, vol. 23 (6), pp. 380-385.

Zhang, H., et al., "Bcl-2 Family Proteins are Essential for Platelet Survival," Cell Death and Differentiation, 2007, vol. 14 (5), pp. 943-951.

Janssens et al., "Formulation and characterization of ternary solid dispersions made up of Itraconazole and two excipients, TPGS 1000 and PVPA 64, that were selected based on a supersaturation screening study," European Journal of Pharmaceutics and Biopharmaceutics 69, 2008, pp. 158-166.

METHODS OF TREATMENT USING SELECTIVE BCL-2 INHIBITORS

RELATED APPLICATION INFORMATION

This application is a continuation of U.S. application Ser. No. 13/301,898, filed Nov. 22, 2011, which claims the benefit of U.S. Provisional Application No. 61/416,689, filed on Nov. 23, 2010, the contents of each of which are herein incorporated by reference.

FIELD OF THE INVENTION

This invention pertains to methods of treating systemic lupus erythematosus, lupus nephritis, and Sjogren's Syndrome with compounds that selectively inhibit the activity of Bcl-2 anti-apoptotic proteins. Specifically, the current invention is directed to treatment with compounds that selectively inhibit the activity of Bcl-2 proteins, with a lesser affinity for inhibiting the activity of other Bcl-2 family proteins, including Bcl-$x_L$.

BACKGROUND OF THE INVENTION

Anti-apoptotic Bcl-2 proteins are associated with a number of diseases. There is therefore an existing need in the therapeutic arts for compounds that inhibit the activity of anti-apoptotic Bcl-2 proteins. The Bcl-2 family of proteins are the key regulators of mitochondria-dependent apoptosis in nucleated cells and consists of both anti-apoptotic (Bcl-$x_L$, Bcl-2, Bcl-w, A1, Mcl-1) and pro-apoptotic (Bak, Bax, Bid, Bim, Bad, Bik, Bmf, Noxa, Puma) members Generally, the expression of Bcl-2 protein is associated with many physiologic functions, including the inhibition of apoptosis in the body, in some cases resulting in proliferation of cells affected by the Bcl-2 inhibition. As such, inhibition of Bcl-2 protein may reduce cell proliferation, leading to improved outcomes related to the treatment and prevention of cancer.

Involvement of Bcl-2 proteins in bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer, spleen cancer, and the like is described in commonly-owned PCT US 2004/36770, published as WO 2005/049593, and PCT US 2004/37911, published as WO 2005/024636.

SUMMARY OF INVENTION

One embodiment of the current invention pertains to a method for treating systemic lupus erythematosus (SLE) and lupus nephritis by administering a therapeutically effective amount of a compound that selectively inhibits Bcl-2 proteins. The selective Bcl-2 inhibitors generally have the following Formula (I):

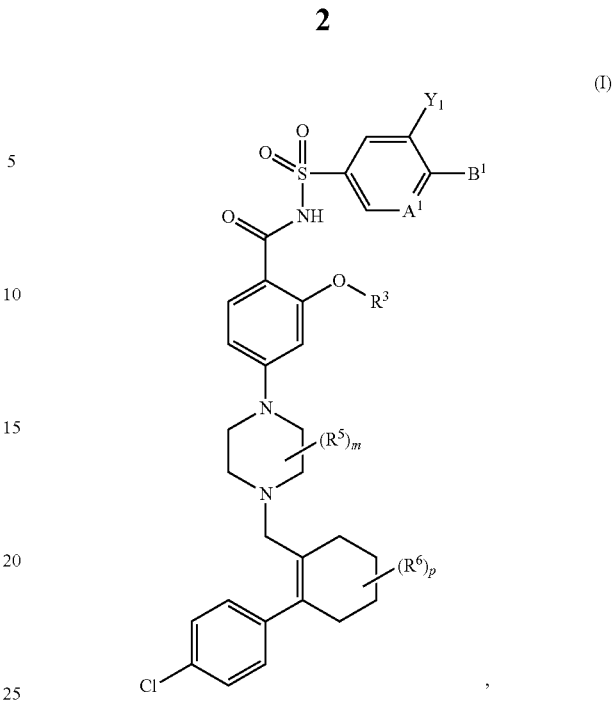

wherein
$A^1$ is N or CH;
$B^1$ is $OR^1$ or $NHR^1$;
$Y^1$ is CN, $NO_2$, $CF_3$, F or Cl;
$R^1$ is $(CH_2)_n R^2$;
$R^2$ is cycloalkyl or heterocyclyl; wherein the heterocyclyl and cycloalkyl are optionally substituted with one or more independently selected $R^4$, $OR^4$, OH, CN, or F;
$R^3$ is heteroaryl; wherein the heteroaryl is optionally substituted with one or more independently selected $NH_2$, Cl, or F;
$R^4$ is alkyl, cycloalkyl, heterocyclyl, or spiroheterocyclyl; wherein the alkyl is optionally substituted with one or more F;
$R^5$ is deuterium;
each $R^6$ is independently selected from $CH_3$, spirocyclopropyl and OH;
m is 0, 1, 2, 3, 4, 5, or 6;
n is 0 or 1; and
p is 0, 1, or 2.

The method of treating SLE or lupus nephritis may also comprise administering a pharmaceutically acceptable salt of a selective Bcl-2 inhibitor. Generally, a selective Bcl-2 inhibitor has a binding affinity ($K_i$) of less than about 1 nanomolar for Bcl-2. In another embodiment, a selective Bcl-2 inhibitor has a binding affinity ($K_i$) of less than about 100 picomolar for Bcl-2. A selective Bcl-2 inhibitor may also have a binding affinity ($K_i$) for Bcl-2 that is approximately 500 times less than the binding affinity for Bcl-$x_L$. In this embodiment, the selective Bcl-2 inhibitor may include N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-[(6-fluoro-1H-indazol-4-yl)oxy]benzamide; 4-(4-{[2-(4-chlorophenyl)-4,4-dimethylcyclohex-1-en-1-yl]methyl}piperazin-1-yl)-N-{[4-({[(2S)-4-cyclopropylmorpholin-2-yl]methyl}amino)-3-nitrophenyl]sulfonyl}-2-(1H-pyrrolo[2,3-b]pyridin-5-yloxy)benzamide; N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]

methyl}piperazin-1-yl)-2-(1H-indazol-4-yloxy)benzamide; 4-(4-{[2-(4-chlorophenyl)-4,4-dimethylcyclohex-1-en-1-yl]methyl}piperazin-1-yl)-2-[(6-fluoro-1H-indol-5-yl)oxy]-N-({4-[(4-fluorotetrahydro-2H-pyran-4-yl)methoxy]-3-nitrophenyl}sulfonyl)benzamide; 4-(4-{[2-(4-chlorophenyl)-4,4-dimethylcyclohex-1-en-1-yl]methyl}piperazin-1-yl)-N-[(4-{[(4,4-difluorocyclohexyl)methyl]amino}-3-nitrophenyl)sulfonyl]-2-(1H-pyrrolo[2,3-b]pyridin-5-yloxy)benzamide; 2-(1H-benzimidazol-4-yloxy)-4-(4-{[2-(4-chlorophenyl)-4,4-dimethylcyclohex-1-en-1-yl]methyl}piperazin-1-yl)-N-({5-fluoro-6-[(4-fluorotetrahydro-2H-pyran-4-yl)methoxy]pyridin-3-yl}sulfonyl)benzamide; 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide; N-({3-chloro-4-[(4-fluorotetrahydro-2H-pyran-4-yl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide; 2-(1H-benzimidazol-4-yloxy)-4-(4-{[2-(4-chlorophenyl)-4,4-dimethylcyclohex-1-en-1-yl]methyl}piperazin-1-yl)-N-[(4-{[(4-cyanocyclohexyl)methyl]amino}-3-nitrophenyl)sulfonyl]benzamide; N-({5-chloro-6-[(cis-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide; N-[(3-chloro-4-{[4-fluoro-1-(oxetan-3-yl)piperidin-4-yl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide; 4-(4-{[2-(4-chlorophenyl)-4,4-dimethylcyclohex-1-en-1-yl]methyl}piperazin-1-yl)-N-({5-cyano-6-[(4-fluorotetrahydro-2H-pyran-4-yl)methoxy]pyridin-3-yl}sulfonyl)-2-(1H-indol-4-yloxy)benzamide; 4-(4-{[2-(4-chlorophenyl)-4,4-dimethylcyclohex-1-en-1-yl]methyl}piperazin-1-yl)-N-[(4-{[(4-fluorotetrahydro-2H-pyran-4-yl)methyl]amino}-3-nitrophenyl)sulfonyl]-2-(1H-pyrrolo[2,3-b]pyridin-5-yloxy)benzamide; N-({3-chloro-4-[(4-fluorotetrahydro-2H-pyran-4-yl)methoxy]phenyl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide; 4-(4-{[2-(4-chlorophenyl)-4,4-dimethylcyclohex-1-en-1-yl]methyl}piperazin-1-yl)-N-({5-fluoro-6-[(4-fluorotetrahydro-2H-pyran-4-yl)methoxy]pyridin-3-yl}sulfonyl)-2-(1H-indazol-4-yloxy)benzamide; 4-(4-{[2-(4-chlorophenyl)-4,4-dimethylcyclohex-1-en-1-yl]methyl}piperazin-1-yl)-N-{4-({[(2R)-4-cyclopropylmorpholin-2-yl]methyl}amino)-3-nitrophenyl]sulfonyl}-2-(1H-pyrrolo[2,3-b]pyridin-5-yloxy)benzamide; 4-(4-{[2-(4-chlorophenyl)-4,4-dimethylcyclohex-1-en-1-yl]methyl}piperazin-1-yl)-N-[(4-{[(trans-4-cyanocyclohexyl)methyl]amino}-3-nitrophenyl)sulfonyl]-2-(1H-pyrrolo[2,3-b]pyridin-5-yloxy)benzamide; Trans-2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)benzamide; 4-(4-{[2-(4-chlorophenyl)-4,4-dimethylcyclohex-1-en-1-yl]methyl}piperazin-1-yl)-N-{4-({(3R)-1-[2-fluoro-1-(fluoromethyl)ethyl]pyrrolidin-3-yl}amino)-3-nitrophenyl]sulfonyl}-2-(1H-pyrrolo[2,3-b]pyridin-5-yloxy)benzamide; Trans-N-({5-chloro-6-[(4-hydroxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide; N-({3-chloro-4-[(trans-4-hydroxycyclohexyl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide; N-({5-chloro-6-[(trans-4-hydroxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-[(6-fluoro-1H-indazol-4-yl)oxy]benzamide; 2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[trans-4-(morpholin-4-yl)cyclohexyl]amino}-3-nitrophenyl)sulfonyl]benzamide; 4-(4-{[2-(4-chlorophenyl)-4,4-dimethylcyclohex-1-en-1-yl]methyl}piperazin-1-yl)-N-[(4-{[(cis-4-hydroxy-4-methylcyclohexyl)methyl]amino}-3-nitrophenyl)sulfonyl]-2-(1H-pyrrolo[2,3-b]pyridin-5-yloxy)benzamide; 4-(4-{[2-(4-chlorophenyl)-4,4-dimethylcyclohex-1-en-1-yl]methyl}piperazin-1-yl)-N-({5-cyano-6-[(4-fluorotetrahydro-2H-pyran-4-yl)methoxy]pyridin-3-yl}sulfonyl)-2-(1H-indazol-4-yloxy)benzamide; N-[(5-chloro-6-{[4-fluoro-1-(oxetan-3-yl)piperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide; 2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide; 4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)-2-(1H-pyrrolo[2,3-b]pyridin-5-yloxy)benzamide; Trans-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]-2-(1H-pyrrolo[2,3-b]pyridin-5-yloxy)benzamide; Trans-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide; 4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-(1H-pyrrolo[2,3-b]pyridin-5-yloxy)benzamide; 2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(3R)-1-(2,2-difluoroethyl)pyrrolidin-3-yl]amino}-3-nitrophenyl)sulfonyl]benzamide; N-({5-chloro-6-[(trans-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide; N-({5-chloro-6-[(cis-1-fluoro-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide; 2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]benzamide; N-({5-chloro-6-[(trans-1-fluoro-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide; 4-(4-{[2-(4-chlorophenyl)-4,4-dimethylcyclohex-1-en-1-yl]methyl}piperazin-1-yl)-N-[(4-{[(trans-4-hydroxy-4-methylcyclohexyl)methyl]amino}-3-nitrophenyl)sulfonyl]-2-(1H-pyrrolo[2,3-b]pyridin-5-yloxy)benzamide; 2-[(3-amino-1H-indazol-4-yl)oxy]-4-(4-{[2-(4-chlorophenyl)-4,4-dimethylcyclohex-1-en-1-yl]methyl}piperazin-1-yl)-N-[(4-

{[(trans-4-methoxycyclohexyl)methyl]amino}-3-nitrophenyl)sulfonyl]benzamide; 4-(4-{[2-(4-chlorophenyl)-4,4-dimethylcyclohex-1-en-1-yl]methyl}piperazin-1-yl)-N-({3-nitro-4-[(2-oxaspiro[3.5]non-7-ylmethyl)amino]phenyl}sulfonyl)-2-(1H-pyrrolo[2,3-b]pyridin-5-yloxy)benzamide; 4-(4-{[2-(4-chlorophenyl)-4,4-dimethylcyclohex-1-en-1-yl]methyl}piperazin-1-yl)-N-({5-cyano-6-[(trans-4-hydroxy-4-methylcyclohexyl)methoxy]pyridin-3-yl}sulfonyl)-2-(1H-indazol-4-yloxy)benzamide; 4-(4-{[2-(4-chlorophenyl)-4,4-dimethylcyclohex-1-en-1-yl]methyl}piperazin-1-yl)-2-[(6-fluoro-1H-indol-5-yl)oxy]-N-{[3-nitro-44 {[4-(oxetan-3-yl)morpholin-2-yl]methyl}amino)phenyl]sulfonyl}benzamide; N-({5-chloro-6-[(trans-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-[(6-fluoro-1H-indazol-4-yl)oxy]benzamide; 4-(4-{[2-(4-chlorophenyl)-4,4-dimethylcyclohex-1-en-1-yl]methyl}piperazin-1-yl)-N-[0-cyano-6-{[4-fluoro-1-(oxetan-3-yl)piperidin-4-yl]methoxy}pyridin-3-yl)sulfonyl]-2-(1H-pyrrolo[2,3-b]pyridin-5-yloxy)benzamide; 2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4-hydroxycyclohexyl)methyl]amino}-3-nitrophenyl)sulfonyl]benzamide; N-({5-chloro-6-[(trans-4-hydroxy-4-methylcyclohexyl)methoxy]pyridin-3-yl}sulfonyl)-2-[(3-chloro-1H-indazol-4-yl)oxy]-4-(4-{[2-(4-chlorophenyl)-4,4-dimethylcyclohex-1-en-1-yl]methyl}piperazin-1-yl)benzamide; 4-[4-{[2-(4-chlorophenyl)-4,4-dimethylcyclohex-1-en-1-yl]methyl}($^2$H$_8$)piperazin-1-yl]-N-({3-nitro-4-[(tetrahydro-2H-pyran-4-ylmethyl)amino]phenyl}sulfonyl)-2-(1H-pyrrolo[2,3-b]pyridin-5-yloxy)benzamide; N-({5-chloro-6-[(trans-1-fluoro-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide; 4-(4-{[2-(4-chlorophenyl)-4,4-dimethylcyclohex-1-en-1-yl]methyl}piperazin-1-yl)-N-[(6-{[(cis-4-hydroxy-4-methylcyclohexyl)methyl]amino}-5-nitropyridin-3-yl)sulfonyl]-2-(1H-pyrrolo[2,3-b]pyridin-5-yloxy)benzamide; 4-(4-{[2-(4-chlorophenyl)-4,4-dimethylcyclohex-1-en-1-yl]methyl}piperazin-1-yl)-N-({5-nitro-6-[(tetrahydro-2H-pyran-4-ylmethyl)amino]pyridin-3-yl}sulfonyl)-2-(1H-pyrrolo[2,3-b]pyridin-5-yloxy)benzamide; 4-(4-{[2-(4-chlorophenyl)-4,4-dimethylcyclohex-1-en-1-yl]methyl}piperazin-1-yl)-N-({6-[(trans-4-hydroxy-4-methylcyclohexyl)methoxy]-5-(trifluoromethyl)pyridin-3-yl}sulfonyl)-2-(1H-indazol-4-yloxy)benzamide; 4-(4-{[2-(4-chlorophenyl)-4,4-dimethylcyclohex-1-en-1-yl]methyl}piperazin-1-yl)-N-[(4-{[(cis-4-ethyl-4-hydroxycyclohexyl)methyl]amino}-3-nitrophenyl)sulfonyl]-2-(1H-pyrrolo[2,3-b]pyridin-5-yloxy)benzamide; and 4-(4-{[2-(4-chlorophenyl)-4,4-dimethylcyclohex-1-en-1-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide.

Another embodiment of the current invention pertains to a method for treating Sjogren's Syndrome by administering a therapeutically effective amount of a compound that selectively inhibits Bcl-2 proteins. The selective Bcl-2 inhibitors generally have the following Formula (I):

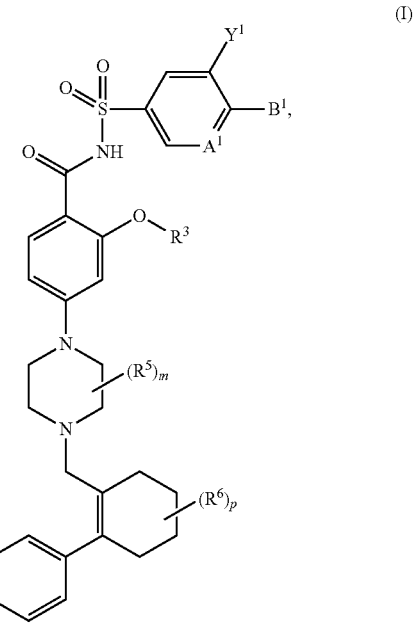

(I)

wherein
$A^1$ is N or CH;
$B^1$ is $OR^1$ or $NHR^1$;
$Y^1$ is CN, $NO_2$, $CF_3$, F or Cl;
$R^1$ is $(CH_2)_nR^2$;
$R^2$ is cycloalkyl or heterocyclyl; wherein the heterocyclyl and cycloalkyl are optionally substituted with one or more independently selected $R^4$, $OR^4$, OH, CN, or F;
$R^3$ is heteroaryl; wherein the heteroaryl is optionally substituted with one or more independently selected $NH_2$, Cl, or F;
$R^4$ is alkyl, cycloalkyl, heterocyclyl, or spiroheterocyclyl; wherein the alkyl is optionally substituted with one or more F;
$R^5$ is deuterium;
each $R^6$ is independently selected from $CH_3$, spirocyclopropyl and OH;
m is 0, 1, 2, 3, 4, 5, or 6;
n is 0 or 1; and
p is 0, 1, or 2.

The method of treating Sjogren's Syndrome may also comprise administering a pharmaceutically acceptable salt of a selective Bcl-2 inhibitor. Generally, a selective Bcl-2 inhibitor has a Bcl-2 binding affinity ($K_i$) of less than about 1 nanomolar. In another embodiment, a selective Bcl-2 inhibitor has a Bcl-2 binding affinity ($K_i$) of less than about 100 picomolar. The selective Bcl-2 inhibitor may also have a binding affinity ($K_i$) for Bcl-2 that is approximately 500 times less than the binding affinity ($K_i$) for Bcl-$x_L$. In this embodiment, the selective Bcl-2 inhibitor may include N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-[(6-fluoro-1H-indazol-4-yl)oxy]benzamide; 4-(4-{[2-(4-chlorophenyl)-4,4-dimethylcyclohex-1-en-1-yl]methyl}piperazin-1-yl)-N-{[4-({[(2S)-4-cyclopropylmorpholin-2-yl]methyl}amino)-3-nitrophenyl]sulfonyl}-2-(1H-pyrrolo[2,3-b]pyridin-5-yloxy)benzamide; N-({5-chloro-6-[(4-fluorotetrahydro-2H-pyran-4-yl)methoxy]pyridin-3-yl}sulfonyl)-4-(4-{[2-(4-chlorophenyl)-4,4- dimethylcyclohex-1-en-1-yl]methyl}piperazin-1-yl)-2-(1H-indazol-4-yloxy)benzamide; 4-(4-{[2-(4-chlorophenyl)-4,4-dimethylcyclohex-1-en-1-yl]methyl}piperazin-1-yl)-2-[(6-fluoro-1H-indol-5-yl)oxy]-N-({4-[(4-fluorotetrahydro-2H-pyran-4-yl)methoxy]-3-nitrophenyl}sulfonyl)benzamide; 4-(4-{[2-(4-chlorophenyl)-4,4-dimethylcyclohex-1-en-1-yl]methyl}piperazin-1-yl)-N-[(4-{[(4,4-difluorocyclohexyl)methyl]amino}-3-nitrophenyl)sulfonyl]-2-(1H-pyrrolo[2,3-b]pyridin-5-yloxy)benzamide; 2-(1H-benzimidazol-4-yloxy)-4-(4-{[2-(4-chlorophenyl)-4,4-dimethylcyclohex-1-en-1-yl]methyl}piperazin-1-yl)-N-({5-fluoro-6-[(4-fluorotetrahydro-2H-pyran-4-yl)methoxy]pyridin-3-yl}sulfonyl)benzamide; 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide; N-({3-chloro-4-[(4-fluorotetrahydro-2H-pyran-4-yl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide; 2-(1H-benzimidazol-4-yloxy)-4-(4-{[2-(4-chlorophenyl)-4,4-dimethylcyclohex-1-en-1-yl]methyl}piperazin-1-yl)-N-[(4-{[(4-cyanocyclohexyl)methyl]amino}-3-nitrophenyl)sulfonyl]benzamide; N-({5-chloro-6-[(cis-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide; N-[(3-chloro-4-{[4-fluoro-1-(oxetan-3-yl)piperidin-4-yl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide; 4-(4-{[2-(4-chlorophenyl)-4,4-dimethylcyclohex-1-en-1-yl]methyl}piperazin-1-yl)-N-({5-cyano-6-[(4-fluorotetrahydro-2H-pyran-4-yl)methoxy]pyridin-3-yl}sulfonyl)-2-(1H-indol-4-yloxy)benzamide; 4-(4-{[2-(4-chlorophenyl)-4,4-dimethylcyclohex-1-en-1-yl]methyl}piperazin-1-yl)-N-[(4-{[(4-fluorotetrahydro-2H-pyran-4-yl)methyl]amino}-3-nitrophenyl)sulfonyl]-2-(1H-pyrrolo[2,3-b]pyridin-5-yloxy)benzamide; N-({3-chloro-4-[(4-fluorotetrahydro-2H-pyran-4-yl)methoxy]phenyl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide; 4-(4-{[2-(4-chlorophenyl)-4,4-dimethylcyclohex-1-en-1-yl]methyl}piperazin-1-yl)-N-({5-fluoro-6-[(4-fluorotetrahydro-2H-pyran-4-yl)methoxy]pyridin-3-yl}sulfonyl)-2-(1H-indazol-4-yloxy)benzamide; 4-(4-{[2-(4-chlorophenyl)-4,4-dimethylcyclohex-1-en-1-yl]methyl}piperazin-1-yl)-N-{4-({[(2R)-4-cyclopropylmorpholin-2-yl]methyl}amino)-3-nitrophenyl]sulfonyl}-2-(1H-pyrrolo[2,3-b]pyridin-5-yloxy)benzamide; 4-(4-{[2-(4-chlorophenyl)-4,4-dimethylcyclohex-1-en-1-yl]methyl}piperazin-1-yl)-N-[(4-{[(trans-4-cyanocyclohexyl)methyl]amino}-3-nitrophenyl)sulfonyl]-2-(1H-pyrrolo[2,3-b]pyridin-5-yloxy)benzamide; Trans-2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)benzamide; 4-(4-{[2-(4-chlorophenyl)-4,4-dimethylcyclohex-1-en-1-yl]methyl}piperazin-1-yl)-N-{4-({(3R)-1-[2-fluoro-1-(fluoromethyl)ethyl]pyrrolidin-3-yl}amino)-3-nitrophenyl]sulfonyl}-2-(1H-pyrrolo[2,3-b]pyridin-5-yloxy)benzamide; Trans-N-({5-chloro-6-[(4-hydroxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide; N-({3-chloro-4-[(trans-4-hydroxycyclohexyl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide; N-({5-chloro-6-[(trans-4-hydroxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-[(6-fluoro-1H-indazol-4-yl)oxy]benzamide; 2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[trans-4-(morpholin-4-yl)cyclohexyl]amino}-3-nitrophenyl)sulfonyl]benzamide; 4-(4-{[2-(4-chlorophenyl)-4,4-dimethylcyclohex-1-en-1-yl]methyl}piperazin-1-yl)-N-[(4-{[(cis-4-hydroxy-4-methylcyclohexyl)methyl]amino}-3-nitrophenyl)sulfonyl]-2-(1H-pyrrolo[2,3-b]pyridin-5-yloxy)benzamide; 4-(4-{[2-(4-chlorophenyl)-4,4-dimethylcyclohex-1-en-1-yl]methyl}piperazin-1-yl)-N-({5-cyano-6-[(4-fluorotetrahydro-2H-pyran-4-yl)methoxy]pyridin-3-yl}sulfonyl)-2-(1H-indazol-4-yloxy)benzamide; N-[(5-chloro-6-{[4-fluoro-1-(oxetan-3-yl)piperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide; 2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide; 4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)-2-(1H-pyrrolo[2,3-b]pyridin-5-yloxy)benzamide; Trans-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]-2-(1H-pyrrolo[2,3-b]pyridin-5-yloxy)benzamide; Trans-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide; 4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-(1H-pyrrolo[2,3-b]pyridin-5-yloxy)benzamide; 2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(3R)-1-(2,2-difluoroethyl)pyrrolidin-3-yl]amino}-3-nitrophenyl)sulfonyl]benzamide; N-({5-chloro-6-[(trans-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide; N-({5-chloro-6-[(cis-1-fluoro-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide; 2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]benzamide; N-({5-chloro-6-[(trans-1-fluoro-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide; 4-(4-{[2-(4-chlorophenyl)-4,4-dimethylcyclohex-1-en-1-yl]methyl}piperazin-1-yl)-N-[(4-{[(trans-4-hydroxy-4-methylcyclohexyl)methyl]amino}-3-nitrophenyl)sulfonyl]-2-(1H-pyrrolo[2,3-b]pyridin-5-yloxy)benzamide; 2-[(3-amino-1H-indazol-4-yl)oxy]-4-(4-{[2-(4-chlorophenyl)-4,4-dimethylcyclohex-1-en-1-yl]methyl}piperazin-1-yl)-N-[(4-

{[(trans-4-methoxycyclohexyl)methyl]amino}-3-nitrophenyl)sulfonyl]benzamide; 4-(4-{[2-(4-chlorophenyl)-4,4-dimethylcyclohex-1-en-1-yl]methyl}piperazin-1-yl)-N-({3-nitro-4-[(2-oxaspiro[3.5]non-7-ylmethyl)amino]phenyl}sulfonyl)-2-(1H-pyrrolo[2,3-b]pyridin-5-yloxy)benzamide; 4-(4-{[2-(4-chlorophenyl)-4,4-dimethylcyclohex-1-en-1-yl]methyl}piperazin-1-yl)-N-({5-cyano-6-[(trans-4-hydroxy-4-methylcyclohexyl)methoxy]pyridin-3-yl}sulfonyl)-2-(1H-indazol-4-yloxy)benzamide; 4-(4-{[2-(4-chlorophenyl)-4,4-dimethylcyclohex-1-en-1-yl]methyl}piperazin-1-yl)-2-[(6-fluoro-1H-indol-5-yl)oxy]-N-{[3-nitro-4-({[4-(oxetan-3-yl)morpholin-2-yl]methyl}amino)phenyl]sulfonyl}benzamide; N-({5-chloro-6-[(trans-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-[(6-fluoro-1H-indazol-4-yl)oxy]benzamide; 4-(4-{[2-(4-chlorophenyl)-4,4-dimethylcyclohex-1-en-1-yl]methyl}piperazin-1-yl)-N-[(5-cyano-6-{[4-fluoro-1-(oxetan-3-yl)piperidin-4-yl]methoxy}pyridin-3-yl)sulfonyl]-2-(1H-pyrrolo[2,3-b]pyridin-5-yloxy)benzamide; 2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4-hydroxycyclohexyl)methyl]amino}-3-nitrophenyl)sulfonyl]benzamide; N-({5-chloro-6-[(trans-4-hydroxy-4-methylcyclohexyl)methoxy]pyridin-3-yl}sulfonyl)-2-[(3-chloro-1H-indazol-4-yl)oxy]-4-(4-{[2-(4-chlorophenyl)-4,4-dimethylcyclohex-1-en-1-yl]methyl}piperazin-1-yl)benzamide; 4-[4-{[2-(4-chlorophenyl)-4,4-dimethylcyclohex-1-en-1-yl]methyl}($^2$H$_8$)piperazin-1-yl]-N-({3-nitro-4-[(tetrahydro-2H-pyran-4-ylmethyl)amino]phenyl}sulfonyl)-2-(1H-pyrrolo[2,3-b]pyridin-5-yloxy)benzamide; N-({5-chloro-6-[(trans-1-fluoro-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide; 4-(4-{[2-(4-chlorophenyl)-4,4-dimethylcyclohex-1-en-1-yl]methyl}piperazin-1-yl)-N-[(6-{[(cis-4-hydroxy-4-methylcyclohexyl)methyl]amino}-5-nitropyridin-3-yl)sulfonyl]-2-(1H-pyrrolo[2,3-b]pyridin-5-yloxy)benzamide; 4-(4-{[2-(4-chlorophenyl)-4,4-dimethylcyclohex-1-en-1-yl]methyl}piperazin-1-yl)-N-({5-nitro-6-[(tetrahydro-2H-pyran-4-ylmethyl)amino]pyridin-3-yl}sulfonyl)-2-(1H-pyrrolo[2,3-b]pyridin-5-yloxy)benzamide; 4-(4-{[2-(4-chlorophenyl)-4,4-dimethylcyclohex-1-en-1-yl]methyl}piperazin-1-yl)-N-({6-[(trans-4-hydroxy-4-methylcyclohexyl)methoxy]-5-(trifluoromethyl)pyridin-3-yl}sulfonyl)-2-(1H-indazol-4-yloxy)benzamide; 4-(4-{[2-(4-chlorophenyl)-4,4-dimethylcyclohex-1-en-1-yl]methyl}piperazin-1-yl)-N-[(4-{[(cis-4-ethyl-4-hydroxycyclohexyl)methyl]amino}-3-nitrophenyl)sulfonyl]-2-(1H-pyrrolo[2,3-b]pyridin-5-yloxy)benzamide; and 4-(4-{[2-(4-chlorophenyl)-4,4-dimethylcyclohex-1-en-1-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide.

BRIEF DESCRIPTION OF THE DRAWINGS

FIG. 2 illustrates the effects of treating mice NZBWF1 with Compound 3 at doses of 30 mg/kg and 100 mg/kg, compared to treatment with phosal vehicle control, and also illustrates the exposure of Compound 3, as measured 24 hours after the last dose.

FIG. 3 illustrates the reduction in CD4+ T cells, CD8+ T Cells, and CD19+ B cells in mice treated with doses of Compound 3 including 30 mg/kg, 100 mg/kg, and 300 mg/kg.

FIG. 4 further illustrates the efficacy of treatment with a selective Bcl-2 inhibitor (Compound 17) in a spontaneous (NZBxNZW)F$_1$ murine model of lupus as assessed by (C) incidence of severe proteinuria (PU≥300 mg/dL) and (D) Kaplan-Meier cumulative survival. Asterisks represent a statistical significance of P<0.05.

FIG. 7 illustrates a statistically significant improvement in glomerulonephritis, tubular changes, and perivascular infiltrates in the mice receiving treatment with 30 mg/kg and 100 mg/kg Compound 1.

DETAILED DESCRIPTION

Figure 1:
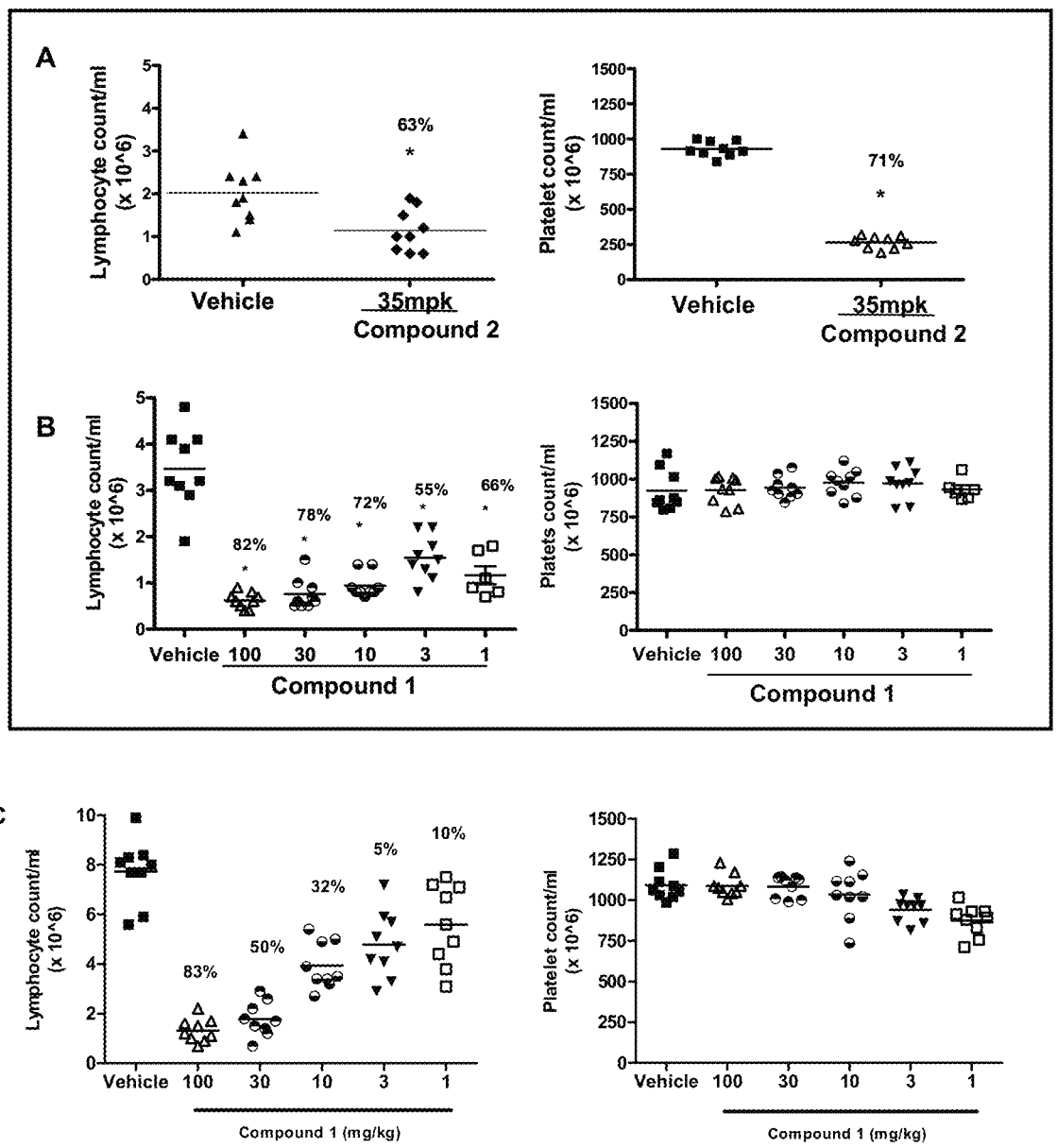
FIG. 1 illustrates the (A) effect of treatment with a non-selective Bcl-2 inhibitor (Compound 2) on both lymphocyte (left) and platelet (right) counts, as well as the (B) effect of treatment with a selective Bcl-2 inhibitor (Compound 1) on both lymphocyte numbers (left) and 1 platelet counts (right) in peripheral blood of (NZBxNZW)F$_1$ mice. (C), (D), (E), (F), (G), (H) and (I) further illustrate the effects of Compounds 1, 17, 5, 7, 8, 9, and 12, respectively, on the lymphocyte numbers (left) and platelet counts (right) in peripheral blood of C57BL6 mice.
Figure 1:
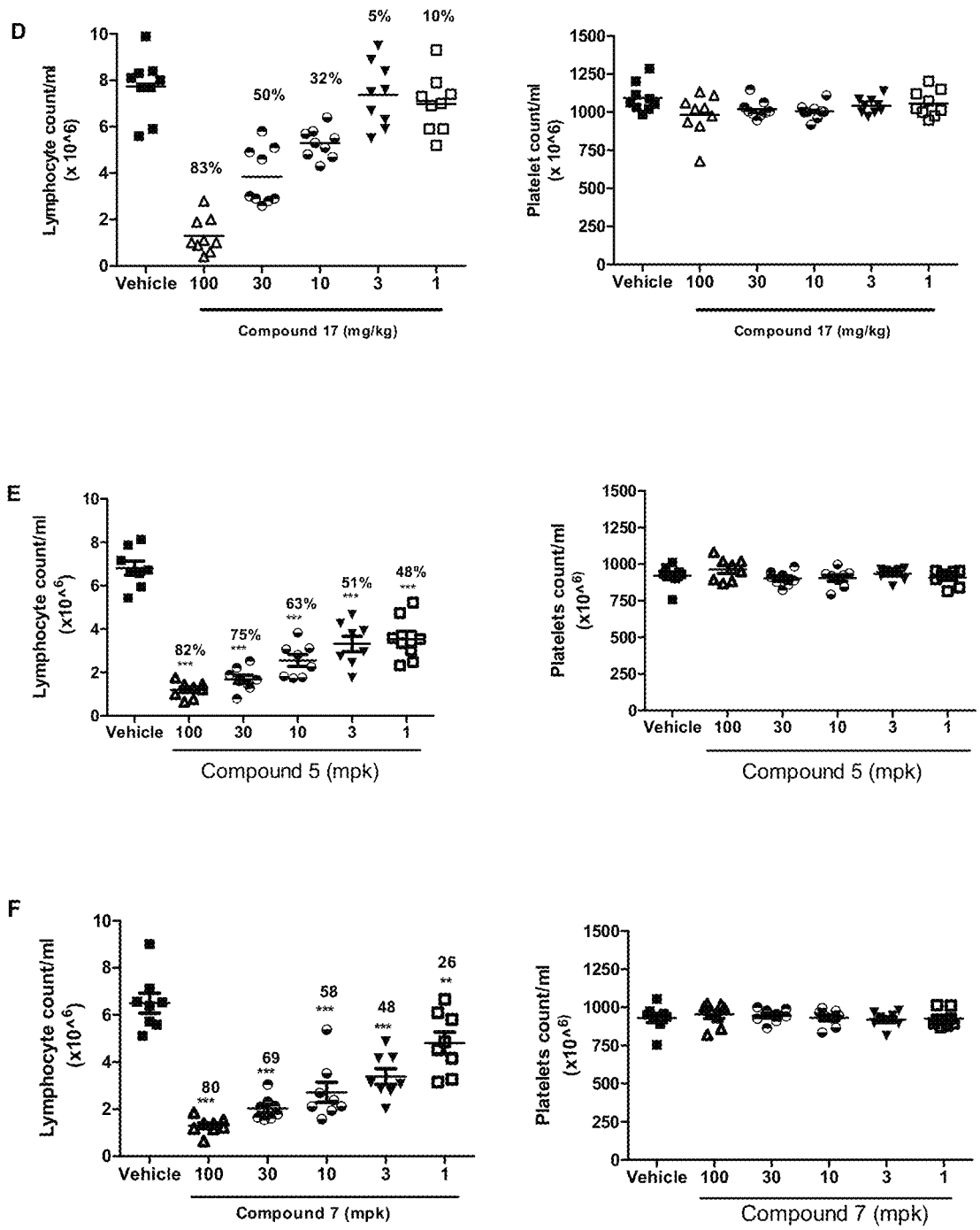
Figure 1:
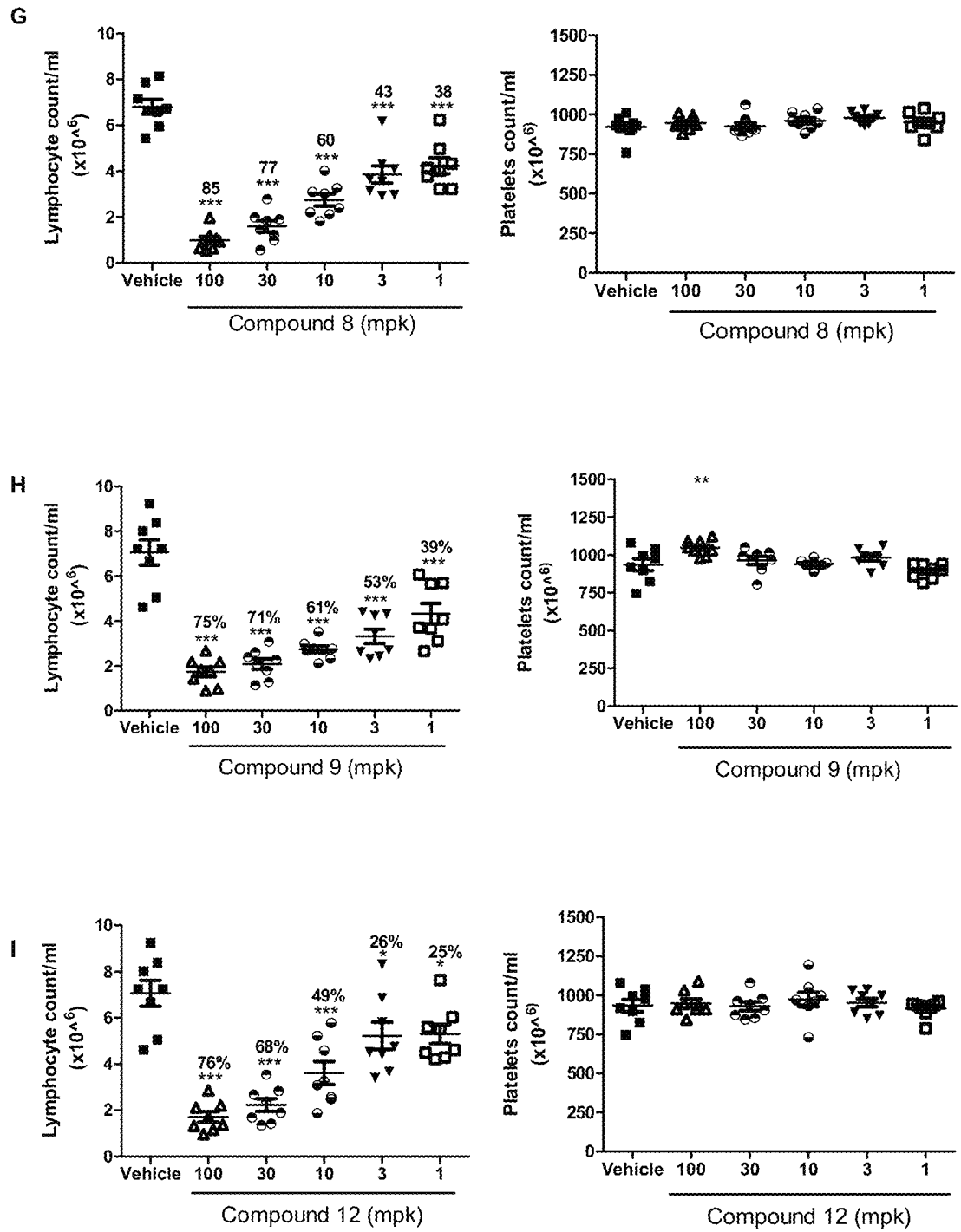

The methods of the current invention are directed to treating various disease states by administering to a patient in need thereof a therapeutically effective amount of a selective Bcl-2 inhibitor. Bcl-2 expression may play a role in the development and disease state progression associated with a number of autoimmune disorders. The inhibition of Bcl-2 protein may also have a positive impact on the treatment of autoimmune diseases including systemic lupus erythematosus (SLE) and lupus nephritis.

Involvement of Bcl-2 proteins in immune and autoimmune diseases is described in *Current Allergy and Asthma Reports* 2003, 3, 378-384; *British Journal of Haematology* 2000, 110 (3), 584-90; *Blood* 2000, 95(4), 1283-92; and *New England Journal of Medicine* 2004, 351(14), 1409-1418. Involvement of Bcl-2 proteins in arthritis is disclosed in commonly-owned U.S. Provisional Patent Application Ser. No. 60/988,479. Involvement of Bcl-2 proteins in bone marrow transplant rejection is disclosed in commonly-owned U.S. patent application Ser. No. 11/941,196.

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. In this application, the use of "or" means "and/or" unless stated otherwise. Furthermore, the use of the term "including", as well as other forms, such as "includes" and "included", is not limiting. With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below. For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated in a useful degree of purity from a reaction mixture.

The terms "treat", "treating" and "treatment" refer to a method of alleviating or abrogating a disease and/or its attendant symptoms.

The terms "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The term "therapeutically effective amount" refers to that amount of the compound being administered sufficient to prevent development of or alleviate to some extent one or more of the symptoms of the condition or disorder being treated.

The term "modulate" refers to the ability of a compound to increase or decrease the function, or activity, of a Bc-2 protein."

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The "subject" is defined herein to include animals such as mammals, including, but not limited to, primates (e.g., humans), cows, sheep, goats, horses, dogs, cats, rabbits, rats, mice and the like. In suitable embodiments, the subject is a human.

The disease states that may be treated with the methods of the current invention include those that result from autoimmune and inflammatory process, specifically systemic lupus erythematosus (SLE), lupus nephritis, and Sjogren's Syndrome. SLE is a chronic systemic autoimmune disease (or autoimmune connective tissue disease) that can affect any part of the body. As occurs in other autoimmune diseases, the immune system attacks the body's cells and tissue, resulting in inflammation and tissue damage. SLE most commonly affects the heart, joints, skin, lungs, blood vessels, liver, kidneys, and nervous system. Accordingly, disease states in which the SLE has affected the kidneys may be termed lupus nephritis. Additionally, Sjogren's Syndrome, also known as "Mikulicz disease" and "Sicca syndrome," is a systemic autoimmune disease in which immune cells attack and destroy the exocrine glands that produce tears and saliva. As such, patients suffering from Sjogren's Syndrome typically suffer from a decreased ability to adequately produce saliva and tears, resulting in excessive dry mouth and dry eyes. Accordingly, in one embodiment, the methods of the current invention are directed to the treatment of SLE and lupus nephritis. In another embodiment, the methods of the invention are directed to the treatment of Sjogren's Syndrome.

As noted, the methods of the current invention comprise treatment with a selective Bcl-2 inhibitor. It is important to note that the term "Ki" is used as an objective measurement for comparative binding affinity. A compound that has a higher binding affinity for the target substrate compared to a second substrate, will display a Ki value for the target substrate that is lower than the second substrate. This is due to the fact that the compound has a higher affinity for the target substrate, and a lesser concentration of the compound is required to bind to and elicit an effect on the target substrate, as compared to the second substrate. For example, selective Bcl-2 inhibitors have a higher affinity for Bcl-2 proteins compared to Bcl-xL proteins, meaning that a lesser concentration of the selective Bcl-2 inhibitor is required to elicit an effect on the Bcl-2 inhibitor, as compared to the concentration required to elicit an effect on the Bcl-xL proteins. As referenced herein, the language stating that a compound has a competitive binding affinity ($K_i$) for Bcl-2 that is less than the binding affinity ($K_i$) for Bcl-$x_L$ should be construed to mean that the compound has a more selective affinity for Bcl-2 than Bcl-$x_L$, as evidenced by a $K_i$ value for Bcl-2 that is less than the $K_i$ value for Bcl-$x_L$.

Specifically, the phase "selective Bcl-2 inhibitor" refers to compounds that have a binding affinity ($K_i$) of (a) less than about 500 nanomolar, less than about 400 nanomolar, less than about 300 nanomolar, less than about 200 nanomolar, less than about 100 nanomolar, less than about 50 nanomolar, less than about 25 nanomolar, less than about 10 nanomolar, less than about 5 nanomolar, less than about 1 nanomolar, less than about 900 picomolar, less than about 800 picomolar, less than about 700 picomolar, less than about 600 picomolar, less than about 500 picomolar, less than about 400 picomolar, less than about 300 picomolar, less than about 200 picomolar, less than about 100 picomolar, and less than about 50 picomolar to Bcl-2; and (b) a competitive binding affinity ($K_i$) for Bcl-2 that is at least about 500, at least about 1000, at least about 2000, at least about 2500, at least about 3000, at least about 3500, and at least about 4000 times less than the binding affinity ($K_i$) for Bcl-$x_L$. In some embodiments of the present invention, the selective Bcl-2 inhibitor compounds that can be used in the methods of the present invention are those compounds having a binding affinity ($K_i$) of less than about 100 picomolar for Bcl-2 and a binding affinity ($K_i$) for Bcl-2 that is approximately 500 times less than the binding affinity for Bcl-$x_L$, a binding affinity ($K_i$) of less than about 100 picomolar for Bcl-2 and a binding affinity ($K_i$) for Bcl-2 that is approximately 1000 times less than the binding affinity for Bcl-$x_L$, a binding affinity ($K_i$) of less than about 100 picomolar for Bcl-2 and a binding affinity ($K_i$) for Bcl-2 that is approximately 2000 times less than the binding affinity for Bcl-$x_L$, a binding affinity ($K_i$) of less than about 100 picomolar for Bcl-2 and a binding affinity ($K_i$) for Bcl-2 that is approximately 2500 times less than the binding affinity for Bcl-$x_L$, a binding affinity (Ki) of less than about 100 picomolar for Bcl-2 and a binding affinity (Ki) for Bcl-2 that is approximately 3000 times less than the binding affinity for Bcl-$x_L$, a binding affinity (Ki) of less than about 100 picomolar for Bcl-2 and a binding affinity (Ki) for Bcl-2 that is approximately 3500 times less than the binding affinity for Bcl-$x_L$, a binding affinity (Ki) of less than about 100 picomolar for Bcl-2 and a binding affinity (Ki) for Bcl-2 that is approximately 4000 times less than the binding affinity for Bcl-$x_L$.

Selective Bcl-2 inhibitor compounds that can be used in the methods of the current invention may generally be considered any compound having the following Formula (I):

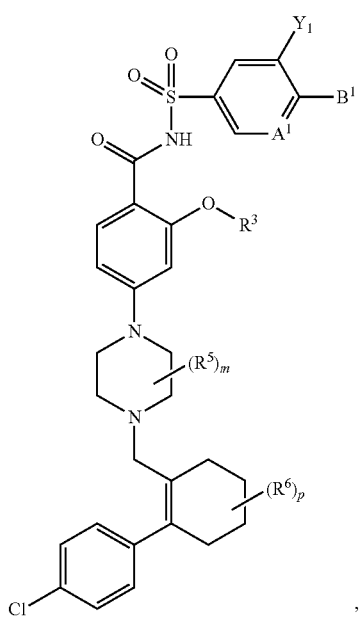

wherein
$A^1$ is N or CH;
$B^1$ is $OR^1$ or $NHR^1$;
$Y^1$ is CN, $NO_2$, $CF_3$, F or Cl;
$R^1$ is $(CH_2)_n R^2$;
$R^2$ is cycloalkyl or heterocyclyl; wherein the heterocyclyl and cycloalkyl are optionally substituted with one or more independently selected $R^4$, $OR^4$, OH, CN, or F;
$R^3$ is heteroaryl; wherein the heteroaryl is optionally substituted with one or more independently selected $NH_2$, Cl, or F;
$R^4$ is alkyl, cycloalkyl, heterocyclyl, or spiroheterocyclyl; wherein the alkyl is optionally substituted with one or more F;
$R^5$ is deuterium;
each $R^6$ is independently selected from $CH_3$, spirocyclopropyl and OH;
m is 0, 1, 2, 3, 4, 5, or 6;
n is 0 or 1; and
p is 0, 1, or 2.

Methods for making selective Bcl-2 inhibitors, such as those encompassed by Formula (I) and which can be used in the methods of the present invention are described in U.S. Ser. No. 12/787,682, filed on May 26, 2010, U.S. Ser. No. 12/793,418 filed on Jun. 3, 2010 which is a continuation-in-part of U.S. Ser. No. 12/631,404 filed on Dec. 4, 2009, and U.S. Ser. No. 12/793,413 filed on Jun. 3, 2010 which is a continuation in part of U.S. Ser. No. 12/631,367, filed on Dec. 4, 2009, the contents of each of which are herein incorporated by reference.

With regard to the various selective Bcl-2 inhibitor compounds encompassed by the current invention, it should be understood that variable moieties herein are represented by identifiers (capital letters with numerical and/or alphabetical superscripts) and may be specifically embodied.

It is meant to be understood that proper valences are maintained for all moieties and combinations thereof, that monovalent moieties having more than one atom are drawn from left to right and are attached through their left ends, and that divalent moieties are also drawn from left to right.

It is also meant to be understood that a specific embodiment of a variable moiety herein may be the same or different as another specific embodiment having the same identifier.

The term "alkenyl" as used herein, means a straight or branched hydrocarbon chain containing from 2 to 10 carbons and containing at least one carbon-carbon double bond. The term "$C_x$-$C_y$ alkyl" means a straight or branched hydrocarbon chain containing at least one carbon-carbon double bond containing x to y carbon atoms. The term "$C_2$-$C_4$ alkenyl" means an alkenyl group containing 2-4 carbon atoms. Representative examples of alkenyl include, but are not limited to buta-2,3-dienyl, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of 2 to 4 carbon atoms and contains at least one carbon-carbon double bond. The term "$C_x$-$C_y$ alkylene" means a divalent group derived from a straight or branched hydrocarbon chain containing at least one carbon-carbon double bond and containing x to y carbon atoms. Representative examples of alkenylene include, but are not limited to, —CH=CH— and —CH$_2$CH=CH—.

The term "alkyl" as used herein, means a straight or branched, saturated hydrocarbon chain containing from 1 to 10 carbon atoms. The term "$C_x$-$C_y$ alkyl" means a straight or branched chain, saturated hydrocarbon containing x to y carbon atoms. For example "$C_2$-$C_{10}$ alkyl" means a straight or branched chain, saturated hydrocarbon containing 2 to 10 carbon atoms. Examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" means a divalent group derived from a straight or branched, saturated hydrocarbon chain of 1 to 10 carbon atoms, for example, of 1 to 4 carbon atoms. The term "$C_x$-$C_y$ alkylene" means a divalent group derived from a straight or branched chain, saturated hydrocarbon containing x to y carbon atoms. For example "$C_2$-$C_6$ alkylene" means a straight or branched chain, saturated hydrocarbon containing 2 to 6 carbon atoms. Examples of alkylene include, but are not limited to, —$CH_2$—, —$CH_2CH_2$—, —$CH_2CH_2CH_2$—, —$CH_2CH_2CH_2CH_2$—, and —$CH_2CH(CH_3)CH_2$—.

The term "alkynyl" as used herein, means a straight or branched chain hydrocarbon group containing from 2 to 10 carbon atoms and containing at least one carbon-carbon triple bond. The term "$C_x$-$C_y$ alkynyl" means a straight or branched chain hydrocarbon group containing from x to y carbon atoms. Representative examples of alkynyl include, but are not limited, to acetylenyl, 1-propynyl, 2-propynyl, 3-butynyl, 2-pentynyl, and 1-butynyl.

The term "alkynylene," as used herein, means a divalent radical derived from a straight or branched chain hydrocarbon group containing from 2 to 10 carbon atoms and containing at least one carbon-carbon triple bond.

The term "aryl" (alone or in combination with another term(s)) means an aromatic carbocyclyl containing from 6 to 14 carbon ring atoms. An aryl may be monocyclic or polycyclic (i.e., may contain more than one ring). In the case of polycyclic aromatic rings, only one ring the polycyclic system is required to be unsaturated while the remaining ring(s) may be saturated, partially saturated or unsaturated. Examples of aryls include phenyl, naphthalenyl, indenyl, indanyl, and tetrahydronapthyl.

The term "carbocyclyl" (alone or in combination with another term(s)) means a saturated cyclic (i.e., "cycloalkyl"), partially saturated cyclic (i.e., "cycloalkenyl"), or completely unsaturated (i.e., "aryl") hydrocarbyl substituent containing from 3 to 14 carbon ring atoms ("ring atoms" are the atoms bound together to form the ring or rings of a cyclic substituent). A carbocyclyl may be a single-ring (monocyclic) or polycyclic ring structure.

A carbocyclyl may be a single ring structure, which typically contains from 3 to 8 ring atoms, more typically from 3 to 6 ring atoms, and even more typically 5 to 6 ring atoms. Examples of such single-ring carbocyclyls include cyclopropyl(cyclopropanyl), cyclobutyl(cyclobutanyl), cyclopentyl(cyclopentanyl), cyclopentenyl, cyclopentadienyl, cyclohexyl(cyclohexanyl), cyclohexenyl, cyclohexadienyl, and phenyl. A carbocyclyl may alternatively be polycyclic (i.e., may contain more than one ring). Examples of polycyclic carbocyclyls include bridged, fused, and spirocyclic carbocyclyls. In a spirocyclic carbocyclyl, one atom is common to two different rings. An example of a spirocyclic carbocyclyl substituent is spirocyclopropyl. In a spirocyclic carbocyclyl, one atom is common to two different rings. An example of a spirocyclic carbocyclyl is spiropentanyl. In a bridged carbocyclyl, the rings share at least two common non-adjacent atoms. Examples of bridged carbocyclyls include bicyclo[2.2.1]heptanyl, bicyclo[2.2.1]hept-2-enyl, and adamantanyl. In a fused-ring carbocyclyl system, two or more rings may be fused together, such that two rings share one common bond. Examples of two- or three-fused ring carbocyclyls include naphthalenyl, tetrahydronaphthalenyl(tetralinyl), indenyl, indanyl(dihydroindenyl), anthracenyl, phenanthrenyl, and decalinyl.

The term "cyclic moiety," as used herein, means benzene, phenyl, phenylene, cycloalkane, cycloalkyl, cycloalkylene, cycloalkene, cycloalkenyl, cycloalkenylene, cycloalkyne, cycloalkynyl, cycloalkynylene, heteroarene, heteroaryl, heterocycloalkane, heterocycloalkyl, heterocycloalkene, heterocycloalkenyl and spiroalkyl.

The term "cycloalkylene" or cycloalkyl" or "cycloalkane" as used herein, means a monocyclic or bridged hydrocarbon ring system. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The monocyclic ring may contain one or two alkylene bridges, each consisting of one, two, or three carbon atoms, each linking two non-adjacent carbon atoms of the ring system. Non-limiting examples of such bridged cycloalkyl ring systems include bicyclo[3.1.1]heptane, bicyclo[2.2.1]heptane, bicyclo[2.2.2]octane, bicyclo[3.2.2]nonane, bicyclo[3.3.1]nonane, bicyclo[4.2.1]nonane, tricyclo[3.3.1.0$^{3,7}$]nonane (octahydro-2,5-methanopentalene or noradamantane), and tricyclo[3.3.1.1$^{3,7}$]decane (adamantane). The monocyclic and bridged cycloalkyl can be attached to the parent molecular moiety through any substitutable atom contained within the ring system.

The term "cycloalkenylene," or "cycloalkenyl" or "cycloalkene" as used herein, means a monocyclic or a bridged hydrocarbon ring system. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two, or three double bonds. Representative examples of monocyclic cycloalkenyl groups include, but are not limited to, cyclobutenyl, cyclopentenyl, cyclohexenyl, cycloheptenyl, and cyclooctenyl. The monocyclic cycloalkenyl ring may contain one or two alkylene bridges, each consisting of one, two, or three carbon atoms, each linking two non-adjacent carbon atoms of the ring system. Representative examples of the bicyclic cycloalkenyl groups include, but are not limited to, 4,5,6,7-tetrahydro-3aH-indene, octahydronaphthalenyl, and 1,6-dihydro-pentalene. The monocyclic and bicyclic cycloalkenyl can be attached to the parent molecular moiety through any substitutable atom contained within the ring systems.

The term "cycloalkyne," or "cycloalkynyl," or "cycloalkynylene," as used herein, means a monocyclic or a bridged hydrocarbon ring system. The monocyclic cycloalkynyl has eight or more carbon atoms, zero heteroatoms, and one or more triple bonds. The monocyclic cycloalkynyl ring may contain one or two alkylene bridges, each consisting of one, two, or three carbon atoms, each linking two non-adjacent carbon atoms of the ring system. The monocyclic and bridged cycloalkynyl can be attached to the parent molecular moiety through any substitutable atom contained within the ring systems.

The term "heteroarene," or "heteroaryl," or "heteroarylene," as used herein, means a five-membered or six-membered aromatic ring having at least one carbon atom and one or more than one independently selected nitrogen, oxygen or sulfur atom. The heteroarenes of this invention are connected through any adjacent atoms in the ring, provided that proper valences are maintained. Specifically, the term "heteroaryl" (alone or in combination with another term(s)) means an aromatic heterocyclyl containing from 5 to 14 ring atoms. A heteroaryl may be a single ring or 2 or 3 fused rings. Examples of heteroaryl substituents include 6-membered ring substituents such as pyridyl, pyrazyl, pyrimidinyl, pyridazinyl, and 1,3,5-, 1,2,4- or 1,2,3-triazinyl; 5-membered ring substituents such as imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 65-membered fused ring substituents such as benzothiofuranyl, benzisoxazolyl, benzoxazolyl, imidazolyl, indolyl, benzoimidazolyl, pyrrolo[2,3-b]pyridinyl, purinyl, and anthranilyl; and 66-membered fused rings such as benzopyranyl, quinolinyl, isoquinolinyl, cinnolinyl, quinazolinyl, and benzoxazinyl.

The term "heterocyclyl" (alone or in combination with another term(s)) means a saturated (i.e., "heterocycloalkyl"), partially saturated (i.e., "heterocycloalkenyl"), or completely unsaturated (i.e., "heteroaryl") ring structure containing a total of 3 to 14 ring atoms. At least one of the ring atoms is a heteroatom (i.e., oxygen, nitrogen, or sulfur), with the remaining ring atoms being independently selected from the group consisting of carbon, oxygen, nitrogen, and sulfur. A heterocyclyl may be a single-ring (monocyclic) or polycyclic ring structure. A heterocyclyl may be a single ring, which typically contains from 3 to 7 ring atoms, more typically from 3 to 6 ring atoms, and even more typically 5 to 6 ring atoms. Examples of single-ring heterocyclyls include furanyl, dihydrofuranyl, tetrahydrofuranyl, tetrahydropyranyl, thiophenyl (thiofuranyl), dihydrothiophenyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, oxazolidinyl, isoxazolidinyl, isoxazolyl, thiazolyl, isothiazolyl, thiazolinyl, isothiazolinyl, thiazolidinyl, isothiazolidinyl, thiodiazolyl, oxadiazolyl (including 1,2,3-oxadiazolyl, 1,2,4-oxadiazolyl, 1,2,5-oxadiazolyl(furazanyl), or 1,3,4-oxadiazolyl), oxatriazolyl (including 1,2,3,4-oxatriazolyl or 1,2,3,5-oxatriazolyl), oxetanyl, dioxazolyl (including 1,2,3-dioxazolyl, 1,2,4-dioxazolyl, 1,3,2-dioxazolyl, or 1,3,4-dioxazolyl), oxathiazolyl, oxathiolyl, oxathiolanyl, pyranyl, dihydropyranyl, thiopyranyl, tetrahydrothiopyranyl, pyridinyl(azinyl), piperidinyl, diazinyl (including pyridazinyl(1,2-diazinyl), pyrimidinyl(1,3-diazinyl), or pyrazinyl(1,4-diazinyl)), piperazinyl, triazinyl (including 1,3,5-triazinyl, 1,2,4-triazinyl, and 1,2,3-triazinyl)), oxazinyl (including 1,2-oxazinyl, 1,3-oxazinyl, or 1,4-oxazinyl)), oxathiazinyl (including 1,2,3-oxathiazinyl, 1,2,4-oxathiazinyl, 1,2,5-oxathiazinyl, or 1,2,6-oxathiazinyl)), oxadiazinyl (including 1,2,3-oxadiazinyl, 1,2,4-oxadiazinyl, 1,4,2-oxadiazinyl, or 1,3,5-oxadiazinyl)), morpholinyl, azepinyl, oxepinyl, thiepinyl, and diazepinyl.

A heterocyclyl may alternatively be polycyclic (i.e., may contain more than one ring). Examples of polycyclic heterocyclyls include bridged, fused, and spirocyclic heterocyclyls. In a spirocyclic heterocyclyl, one atom is common to two different rings. Examples of spirocyclic heterocyclyls include 2-oxaspiro[3.5]nonanyl. Examples of polycyclic heterocyclyls include bridged, fused, and spirocyclic heterocyclyls. In a spirocyclic heterocyclyl, one atom is common to two different rings. Examples of spirocyclic heterocyclyl include 2-oxaspiro[3.5]nonanyl. In a bridged heterocyclyl, the rings share at least two common non-adjacent atoms. In a fused-ring heterocyclyl, two or more rings may be fused together, such that two rings share one common bond. Examples of fused ring heterocyclyls containing two or three rings include indolizinyl, pyranopyrrolyl, 4H-quinolizinyl, purinyl, naphthyridinyl, pyrrolo[2,3-b]pyridinyl, pyridopyridinyl (including pyrido[3,4-b]-pyridinyl, pyrido[3,2-b]-pyridinyl, or pyrido[4,3-b]-pyridinyl), and pteridinyl. Other examples of fused-ring heterocyclyls include benzo-fused heterocyclyls, such as indolyl, indazoyl, isoindolyl(isobenzazolyl, pseudoisoindolyl), indoleninyl(pseudoindolyl), isoindazolyl(benzpyrazolyl), benzoimidazolyl, benzazinyl (including quinolinyl(1-benzazinyl) or isoquinolinyl(2-benzazinyl)), phthalazinyl, quinoxalinyl, quinazolinyl, benzodiazinyl (including cinnolinyl(1,2-benzodiazinyl) or quinazolinyl(1,3-benzodiazinyl)), benzopyranyl (including chromanyl or isochromanyl), benzoxazinyl (including 1,3,2-benzoxazinyl, 1,4,2-benzoxazinyl, 2,3,1-benzoxazinyl, or 3,1,4-benzoxazinyl), and benzisoxazinyl (including 1,2-benzisoxazinyl or 1,4-benzisoxazinyl).

The term "heterocycloalkyl" (alone or in combination with another term(s)) means a saturated heterocyclyl.

The term "heterocycloalkene," or "heterocycloalkenyl," or "heterocycloalkenylene," as used herein, means monocyclic or bridged three-, four-, five-, six-, seven-, or eight-membered ring containing at least one heteroatom independently selected from the group consisting of O, N, and S and one or more double bonds. The monocyclic and bridged heterocycloalkene are connected to the parent molecular moiety through any substitutable carbon atom or any substitutable nitrogen atom contained within the rings. The nitrogen and sulfur heteroatoms in the heterocycle rings may optionally be oxidized and the nitrogen atoms may optionally be quarternized. Representative examples of heterocycloalkene groups include, but are not limited to, tetrahydrooxocinyl, 1,4,5,6-tetrahydropyridazinyl, 1,2,3,6-tetrahydropyridinyl, dihydropyranyl, imidazolinyl, isothiazolinyl, oxadiazolinyl, isoxazolinyl, oxazolinyl, pyranyl, pyrazolinyl, pyrrolinyl, thiadiazolinyl, thiazolinyl, and thiopyranyl.

The term "phenylene," as used herein, means a divalent radical formed by removal of a hydrogen atom from phenyl.

The term "spiroalkyl," as used herein, means alkylene, both ends of which are attached to the same carbon atom and is exemplified by $C_2$-spiroalkyl, $C_3$-spiroalkyl, $C_4$-spiroalkyl, $C_5$-spiroalkyl, $C_6$-spiroalkyl, $C_7$-spiroalkyl, $C_8$-spiroalkyl, $C_9$-spiroalkyl and the like.

The term "spiroheteroalkyl," as used herein, means spiroalkyl having one or two $CH_2$ moieties replaced with independently selected O, C(O), CNOH, CNOCH$_3$, S, S(O), $SO_2$ or NH and one or two CH moieties unreplaced or replaced with N.

The term "spiroheteroalkenyl," as used herein, means spiroalkenyl having one or two $CH_2$ moieties replaced with independently selected O, C(O), CNOH, CNOCH$_3$, S, S(O), $SO_2$ or NH and one or two CH moieties unreplaced or replaced with N and also means spiroalkenyl having one or two $CH_2$ moieties unreplaced or replaced with independently selected 0, C(O), CNOH, CNOCH$_3$, S, S(O), $SO_2$ or NH and one or two CH moieties replaced with N.

The term, "spirocyclo," as used herein, means two substituents on the same carbon atom, that, together with the carbon atom to which they are attached, form a cycloalkane, heterocycloalkane, cycloalkene, or heterocycloalkene ring.

The term "$C_2$-$C_5$-spiroalkyl," as used herein, means $C_2$-spiroalkyl, $C_3$-spiroalkyl, $C_4$-spiroalkyl, and $C_5$-spiroalkyl.

The term "$C_2$-spiroalkyl," as used herein, means eth-1,2-ylene, both ends of which replace hydrogen atoms of the same $CH_2$ moiety.

The term "$C_3$-spiroalkyl," as used herein, means prop-1,3-ylene, both ends of which replace hydrogen atoms of the same $CH_2$ moiety.

The term "$C_4$-spiroalkyl," as used herein, means but-1,4-ylene, both ends of which replace hydrogen atoms of the same $CH_2$ moiety.

The term "$C_5$-spiroalkyl," as used herein, means pent-1,5-ylene, both ends of which replace hydrogen atoms of the same $CH_2$ moiety.

The term "C₆-spiroalkyl," as used herein, means hex-1,6-ylene, both ends of which replace hydrogen atoms of the same CH₂ moiety.

The term "NH protecting group," as used herein, means trichloroethoxycarbonyl, tribromoethoxycarbonyl, benzyloxycarbonyl, para-nitrobenzylcarbonyl, ortho-bromobenzyloxycarbonyl, chloroacetyl, dichloroacetyl, trichloroacetyl, trifluoroacetyl, phenylacetyl, formyl, acetyl, benzoyl, tert-amyloxycarbonyl, tert-butoxycarbonyl, para-methoxybenzyloxycarbonyl, 3,4-dimethoxybenzyl-oxycarbonyl, 4-(phenylazo)benzyloxycarbonyl, 2-furfuryl-oxycarbonyl, diphenylmethoxycarbonyl, 1,1-dimethylpropoxy-carbonyl, isopropoxycarbonyl, phthaloyl, succinyl, alanyl, leucyl, 1-adamantyloxycarbonyl, 8-quinolyloxycarbonyl, benzyl, diphenylmethyl, triphenylmethyl, 2-nitrophenylthio, methanesulfonyl, para-toluenesulfonyl, N,N-dimethylaminomethylene, benzylidene, 2-hydroxybenzylidene, 2-hydroxy-5-chlorobenzylidene, 2-hydroxy-1-naphthyl-methylene, 3-hydroxy-4-pyridylmethylene, cyclohexylidene, 2-ethoxycarbonylcyclohexylidene, 2-ethoxycarbonylcyclopentylidene, 2-acetylcyclohexylidene, 3,3-dimethyl-5-oxycyclohexylidene, diphenylphosphoryl, dibenzylphosphoryl, 5-methyl-2-oxo-2H-1,3-dioxol-4-yl-methyl, trimethylsilyl, triethylsilyl, and triphenylsilyl.

The term "C(O)OH protecting group," as used herein, means methyl, ethyl, n-propyl, isopropyl, 1,1-dimethylpropyl, n-butyl, tert-butyl, phenyl, naphthyl, benzyl, diphenylmethyl, triphenylmethyl, para-nitrobenzyl, para-methoxybenzyl, bis(para-methoxyphenyl)methyl, acetylmethyl, benzoylmethyl, para-nitrobenzoylmethyl, para-bromobenzoylmethyl, para-methanesulfonylbenzoylmethyl, 2-tetrahydropyranyl 2-tetrahydrofuranyl, 2,2,2-trichloro-ethyl, 2-(trimethylsilyl)ethyl, acetoxymethyl, propionyloxymethyl, pivaloyloxymethyl, phthalimidomethyl, succinimidomethyl, cyclopropyl, cyclobutyl, cyclopentyl, cyclohexyl, methoxymethyl, methoxyethoxymethyl, 2-(trimethylsilyl)ethoxymethyl, benzyloxymethyl, methylthiomethyl, 2-methylthioethyl, phenylthiomethyl, 1,1-dimethyl-2-propenyl, 3-methyl-3-butenyl, allyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

The term "OH or SH protecting group," as used herein, means benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, methoxycarbonyl, ethoxycarbonyl, tert-butoxycarbonyl, 1,1-dimethylpropoxycarbonyl, isopropoxycarbonyl, isobutyloxycarbonyl, diphenylmethoxycarbonyl, 2,2,2-trichloroethoxycarbonyl, 2,2,2-tribromoethoxycarbonyl, 2-(trimethylsilyl)ethoxycarbonyl, 2-(phenylsulfonyl)ethoxycarbonyl, 2-(triphenylphosphonio)ethoxycarbonyl, 2-furfuryloxycarbonyl, 1-adamantyloxycarbonyl, vinyloxycarbonyl, allyloxycarbonyl, S-benzylthiocarbonyl, 4-ethoxy-1-naphthyloxycarbonyl, 8-quinolyloxycarbonyl, acetyl, formyl, chloroacetyl, dichloroacetyl, trichloroacetyl, trifluoroacetyl, methoxyacetyl, phenoxyacetyl, pivaloyl, benzoyl, methyl, tert-butyl, 2,2,2-trichloroethyl, 2-trimethylsilylethyl, 1,1-dimethyl-2-propenyl, 3-methyl-3-butenyl, allyl, benzyl(phenylmethyl), para-methoxybenzyl, 3,4-dimethoxybenzyl, diphenylmethyl, triphenylmethyl, tetrahydrofuryl, tetrahydropyranyl, tetrahydrothiopyranyl, methoxymethyl, methylthiomethyl, benzyloxymethyl, 2-methoxyethoxymethyl, 2,2,2-trichloroethoxymethyl, 2-(trimethylsilyl)ethoxymethyl, 1-ethoxyethyl, methanesulfonyl, para-toluenesulfonyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitution on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

This patent application uses the terms "substituent" and "radical" interchangeably.

As stated, the selective Bcl-2 inhibitor compounds of the current invention encompass all possible combinations of the substituents for the genus compound of Formula (I). Suitable examples of compounds that fall within the scope of the current invention include, but are not limited to, N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-[(6-fluoro-1H-indazol-4-yl)oxy]benzamide; 4-(4-{[2-(4-chlorophenyl)-4,4-dimethylcyclohex-1-en-1-yl]methyl}piperazin-1-yl)-N-{[4-({[(2S)-4-cyclopropylmorpholin-2-yl]methyl}amino)-3-nitrophenyl]sulfonyl}-2-(1H-pyrrolo[2,3-b]pyridin-5-yloxy)benzamide; N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide; 4-(4-{[2-(4-chlorophenyl)-4,4-dimethylcyclohex-1-en-1-yl]methyl}piperazin-1-yl)-2-[(6-fluoro-1H-indol-5-yl)oxy]-N-({4-[(4-fluorotetrahydro-2H-pyran-4-yl)methoxy]-3-nitrophenyl}sulfonyl)benzamide; 4-(4-{[2-(4-chlorophenyl)-4,4-dimethylcyclohex-1-en-1-yl]methyl}piperazin-1-yl)-N-[(4-{[(4,4-difluorocyclohexyl)methyl]amino}-3-nitrophenyl)sulfonyl]-2-(1H-pyrrolo[2,3-b]pyridin-5-yloxy)benzamide; 2-(1H-benzimidazol-4-yloxy)-4-(4-{[2-(4-chlorophenyl)-4,4-dimethylcyclohex-1-en-1-yl]methyl}piperazin-1-yl)-N-({5-fluoro-6-[(4-fluorotetrahydro-2H-pyran-4-yl)methoxy]pyridin-3-yl}sulfonyl)benzamide; 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)

benzamide; N-({3-chloro-4-[(4-fluorotetrahydro-2H-pyran-4-yl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide; 2-(1H-benzimidazol-4-yloxy)-4-(4-{[2-(4-chlorophenyl)-4,4-dimethylcyclohex-1-en-1-yl]methyl}piperazin-1-yl)-N-[(4-{[(4-cyanocyclohexyl)methyl]amino}-3-nitrophenyl)sulfonyl]benzamide; N-({5-chloro-6-[(cis-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide; N-[(3-chloro-4-{[4-fluoro-1-(oxetan-3-yl)piperidin-4-yl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide; 4-(4-{[2-(4-chlorophenyl)-4,4-dimethylcyclohex-1-en-1-yl]methyl}piperazin-1-yl)-N-({5-cyano-6-[(4-fluorotetrahydro-2H-pyran-4-yl)methoxy]pyridin-3-yl}sulfonyl)-2-(1H-indol-4-yloxy)benzamide; 4-(4-{[2-(4-chlorophenyl)-4,4-dimethylcyclohex-1-en-1-yl]methyl}piperazin-1-yl)-N-[(4-{[(4-fluorotetrahydro-2H-pyran-4-yl)methyl]amino}-3-nitrophenyl)sulfonyl]-2-(1H-pyrrolo[2,3-b]pyridin-5-yloxy)benzamide; N-({3-chloro-4-[(4-fluorotetrahydro-2H-pyran-4-yl)methoxy]phenyl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide; 4-(4-{[2-(4-chlorophenyl)-4,4-dimethylcyclohex-1-en-1-yl]methyl}piperazin-1-yl)-N-({5-fluoro-6-[(4-fluorotetrahydro-2H-pyran-4-yl)methoxy]pyridin-3-yl}sulfonyl)-2-(1H-indazol-4-yloxy)benzamide; 4-(4-{[2-(4-chlorophenyl)-4,4-dimethylcyclohex-1-en-1-yl]methyl}piperazin-1-yl)-N-{4-({[(2R)-4-cyclopropylmorpholin-2-yl]methyl}amino)-3-nitrophenyl]sulfonyl}-2-(1H-pyrrolo[2,3-b]pyridin-5-yloxy)benzamide; 4-(4-{[2-(4-chlorophenyl)-4,4-dimethylcyclohex-1-en-1-yl]methyl}piperazin-1-yl)-N-[(4-{[(trans-4-cyanocyclohexyl)methyl]amino}-3-nitrophenyl)sulfonyl]-2-(1H-pyrrolo[2,3-b]pyridin-5-yloxy)benzamide; Trans-2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)benzamide; 4-(4-{[2-(4-chlorophenyl)-4,4-dimethylcyclohex-1-en-1-yl]methyl}piperazin-1-yl)-N-[4-({(3R)-1-[2-fluoro-1-(fluoromethyl)ethyl]pyrrolidin-3-yl}amino)-3-nitrophenyl]sulfonyl}-2-(1H-pyrrolo[2,3-b]pyridin-5-yloxy)benzamide; Trans-N-({5-chloro-6-[(4-hydroxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide; N-({3-chloro-4-[(trans-4-hydroxycyclohexyl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide; N-({5-chloro-6-[(trans-4-hydroxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-[(6-fluoro-1H-indazol-4-yl)oxy]benzamide; 2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[trans-4-(morpholin-4-yl)cyclohexyl]amino}-3-nitrophenyl)sulfonyl]benzamide; 4-(4-{[2-(4-chlorophenyl)-4,4-dimethylcyclohex-1-en-1-yl]methyl}piperazin-1-yl)-N-[(4-{[(cis-4-hydroxy-4-methylcyclohexyl)methyl]amino}-3-nitrophenyl)sulfonyl]-2-(1H-pyrrolo[2,3-b]pyridin-5-yloxy)benzamide; 4-(4-{[2-(4-chlorophenyl)-4,4-dimethylcyclohex-1-en-1-yl]methyl}piperazin-1-yl)-N-({5-cyano-6-[(4-fluorotetrahydro-2H-pyran-4-yl)methoxy]pyridin-3-yl}sulfonyl)-2-(1H-indazol-4-yloxy)benzamide; N-[(5-chloro-6-{[4-fluoro-1-(oxetan-3-yl)piperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide; 2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide; 4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)-2-(1H-pyrrolo[2,3-b]pyridin-5-yloxy)benzamide; Trans-4-(4-{[2-(4-chlorophenyl)-4,4-dimethylcyclohex-1-en-1-yl]methyl}piperazin-1-yl)-N-({4-{[(4-methoxycyclohexyl)methyl]amino}-3-nitrophenyl)sulfonyl]-2-(1H-pyrrolo[2,3-b]pyridin-5-yloxy)benzamide; Trans-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide; 4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-(1H-pyrrolo[2,3-b]pyridin-5-yloxy)benzamide; 2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(3R)-1-(2,2-difluoroethyl)pyrrolidin-3-yl]amino}-3-nitrophenyl)sulfonyl]benzamide; N-({5-chloro-6-[(trans-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide; N-({5-chloro-6-[(cis-1-fluoro-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide; 2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]benzamide; N-({5-chloro-6-[(trans-1-fluoro-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide; 4-(4-{[2-(4-chlorophenyl)-4,4-dimethylcyclohex-1-en-1-yl]methyl}piperazin-1-yl)-N-[(4-{[(trans-4-hydroxy-4-methylcyclohexyl)methyl]amino}-3-nitrophenyl)sulfonyl]-2-(1H-pyrrolo[2,3-b]pyridin-5-yloxy)benzamide; 2-[(3-amino-1H-indazol-4-yl)oxy]-4-(4-{[2-(4-chlorophenyl)-4,4-dimethylcyclohex-1-en-1-yl]methyl}piperazin-1-yl)-N-[(4-{[(trans-4-methoxycyclohexyl)methyl]amino}-3-nitrophenyl)sulfonyl]benzamide; 4-(4-{[2-(4-chlorophenyl)-4,4-dimethylcyclohex-1-en-1-yl]methyl}piperazin-1-yl)-N-({3-nitro-4-[(2-oxaspiro[3.5]non-7-ylmethyl)amino]phenyl}sulfonyl)-2-(1H-pyrrolo[2,3-b]pyridin-5-yloxy)benzamide; 4-(4-{[2-(4-chlorophenyl)-4,4-dimethylcyclohex-1-en-1-yl]methyl}piperazin-1-yl)-N-({5-cyano-6-[(trans-4-hydroxy-4-methylcyclohexyl)methoxy]pyridin-3-yl}sulfonyl)-2-(1H-indazol-4-yloxy)benzamide; 4-(4-{[2-(4-chlorophenyl)-4,4-dimethylcyclohex-1-en-1-yl]methyl}piperazin-1-yl)-2-[(6-fluoro-1H-indol-5-yl)oxy]-N-{[3-nitro-44 {[4-(oxetan-3-yl)morpholin-2-yl]methyl}amino)phenyl]sulfonyl}benzamide; N-({5-chloro-6-[(trans-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-

[(6-fluoro-1H-indazol-4-yl)oxy]benzamide; 4-(4-{[2-(4-chlorophenyl)-4,4-dimethylcyclohex-1-en-1-yl]methyl}piperazin-1-yl)-N-[(5-cyano-6-{[4-fluoro-1-(oxetan-3-yl)piperidin-4-yl]methoxy}pyridin-3-yl)sulfonyl]-2-(1H-pyrrolo[2,3-b]pyridin-5-yloxy)benzamide; 2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4-hydroxycyclohexyl)methyl]amino}-3-nitrophenyl)sulfonyl]benzamide; N-({5-chloro-6-[(trans-4-hydroxy-4-methylcyclohexyl)methoxy]pyridin-3-yl}sulfonyl)-2-[(3-chloro-1H-indazol-4-yl)oxy]-4-(4-{[2-(4-chlorophenyl)-4,4-dimethylcyclohex-1-en-1-yl]methyl}piperazin-1-yl)benzamide; 4-[4-{[2-(4-chlorophenyl)-4,4-dimethylcyclohex-1-en-1-yl]methyl}($^2H_8$)piperazin-1-yl]-N-({3-nitro-4-[(tetrahydro-2H-pyran-4-ylmethyl)amino]phenyl}sulfonyl)-2-(1H-pyrrolo[2,3-b]pyridin-5-yloxy)benzamide; N-({5-chloro-6-[(trans-1-fluoro-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide; 4-(4-{[2-(4-chlorophenyl)-4,4-dimethylcyclohex-1-en-1-yl]methyl}piperazin-1-yl)-N-[(6-{[(cis-4-hydroxy-4-methylcyclohexyl)methyl]amino}-5-nitropyridin-3-yl)sulfonyl]-2-(1H-pyrrolo[2,3-b]pyridin-5-yloxy)benzamide; 4-(4-{[2-(4-chlorophenyl)-4,4-dimethylcyclohex-1-en-1-yl]methyl}piperazin-1-yl)-N-({5-nitro-6-[(tetrahydro-2H-pyran-4-ylmethyl)amino]pyridin-3-yl}sulfonyl)-2-(1H-pyrrolo[2,3-b]pyridin-5-yloxy)benzamide; 4-(4-{[2-(4-chlorophenyl)-4,4-dimethylcyclohex-1-en-1-yl]methyl}piperazin-1-yl)-N-({6-[(trans-4-hydroxy-4-methylcyclohexyl)methoxy]-5-(trifluoromethyl)pyridin-3-yl}sulfonyl)-2-(1H-indazol-4-yloxy)benzamide; 4-(4-{[2-(4-chlorophenyl)-4,4-dimethylcyclohex-1-en-1-yl]methyl}piperazin-1-yl)-N-[(4-{[(cis-4-ethyl-4-hydroxycyclohexyl)methyl]amino}-3-nitrophenyl)sulfonyl]-2-(1H-pyrrolo[2,3-b]pyridin-5-yloxy)benzamide; and 4-(4-{[2-(4-chlorophenyl)-4,4-dimethylcyclohex-1-en-1-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide. Each of the above compounds and methods for making these compounds are described in U.S. Ser. No. 12/787,682, filed on May 26, 2010, U.S. Ser. No. 12/793,418 filed on Jun. 3, 2010 which is a continuation-in-part of U.S. Ser. No. 12/631,404 filed on Dec. 4, 2009 and U.S. Ser. No. 12/793,413 filed on Jun. 3, 2010 which is a continuation in part of U.S. Ser. No. 12/631,367, filed on Dec. 4, 2009, the contents of each of which are herein incorporated by reference.

The selective Bcl-2 inhibitor compounds used in the methods of the current invention may also include a pharmaceutically acceptable salt form of a compound having Formula (I). The phrase "pharmaceutically acceptable salt(s)", as used herein, means those salts of the selective Bcl-2 inhibitors of the invention that are safe and effective for administration to a patient and that do not adversely affect the therapeutic qualities of the compound. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the invention can form pharmaceutically acceptable salts with various amino acids. Suitable base salts include, but are not limited to, aluminum, calcium, lithium, magnesium, potassium, sodium, zinc, and diethanolamine salts. For a review on pharmaceutically acceptable salts see Berge et al., 66 *J. Pharm. Sci.*, 1-19 (1977), incorporated herein by reference, in its entirety.

The compounds used in the methods of the current invention may also comprise geometric isomers. Compounds of this invention may contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers. Substituents around a cycloalkyl or heterocycloalkyl are designated as being of cis or trans configuration. Furthermore, the invention contemplates the various isomers and mixtures thereof resulting from the disposal of substituents around an adamantane ring system. Two substituents around a single ring within an adamantane ring system are designated as being of Z or E relative configuration. For examples, see C. D. Jones, M. Kaselj, R. N. Salvatore, W. J. le Noble *J. Org. Chem.* 1998, 63, 2758-2760 and E. L. Eliel, and S. H. Wilen. (1994) *Stereochemistry of Organic Compounds.* New York, N.Y.: John Wiley & Sons, Inc.

The selective Bcl-2 inhibitor compounds may also contain asymmetrically substituted carbon atoms in the R or S configuration, in which the terms "R" and "S" are as defined by the IUPAC 1974 Recommendations for Section E, Fundamental Stereochemistry, Pure Appl. Chem. (1976) 45, 13-10. Compounds having asymmetrically substituted carbon atoms with equal amounts of R and S configurations are racemic at those carbon atoms. Atoms with an excess of one configuration over the other are assigned the configuration present in the higher amount, such an excess of about 85%-90%, an excess of about 95%-99%, or an excess greater than about 99%. Accordingly, this invention includes racemic mixtures, relative and absolute stereoisomers, and mixtures of relative and absolute stereoisomers.

The selective Bcl-2 inhibitor compounds used in the methods of the current invention containing NH, C(O)OH, OH or SH moieties may have attached thereto prodrug-forming moieties. The prodrug-forming moieties are removed by metabolic processes and release the compounds having the freed hydroxyl, amino or carboxylic acid in vivo. Prodrugs are useful for adjusting such pharmacokinetic properties of the compounds as solubility and/or hydrophobicity, absorption in the gastrointestinal tract, bioavailability, tissue penetration, and rate of clearance.

The compounds used in the various embodiments can also exist in isotope-labeled or isotope-enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to, $^2H$, $^3H$, $^{13}C$, $^{14}C$, $^{15}N$, $^{18}O$, $^{32}P$, $^{35}S$, $^{18}F$, $^{36}Cl$, and $^{125}I$. Compounds that contain other isotopes of these and/or other atoms are within the scope of this invention.

In another embodiment, the isotope-labeled compounds contain deuterium ($^2H$), tritium ($^3H$) or $^{14}C$ isotopes. Isotope-labeled compounds of this invention can be prepared by the general methods well known to persons having ordinary skill in the art. Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4/D_2O$. In addition to the above, relevant procedures and intermediates are disclosed, for instance, in Lizondo, J et al., *Drugs Fut,* 21(11), 1116 (1996); Brickner, S J et al., *J Med Chem,* 39(3), 673 (1996); Mallesham, B et al., *Org Lett,* 5(7), 963 (2003); PCT publications WO1997010223, WO2005099353, WO1995007271, WO2006008754; U.S. Pat. Nos. 7,538,189; 7,534,814; 7,531,685; 7,528,131; 7,521, 421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of Bcl-2 inhibitors in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., J. *Labelled Comp. Radiopharmaceut.,* 36(10):927-932 (1995); Kushner et al., *Can. J. Physiol. Pharmacol.,* 77, 79-88 (1999)).

In addition, non-radio active isotope containing drugs, such as deuterated drugs called "heavy drugs," can be used for the treatment of diseases and conditions related to Bcl-2 activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czakja D M et al., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. *Advanced Medical Publishing, Madison Wis.* pp. 125-134; *Diabetes Metab.* 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmacokinetic profile or efficacy relative to the non-isotopic compound.

The current methods may also incorporate a prodrug form of the selective Bcl-2 inhibitor compound. Prodrugs are derivatives of an active drug designed to ameliorate some identified, undesirable physical or biological property. The physical properties are usually solubility (too much or not enough lipid or aqueous solubility) or stability related, while problematic biological properties include too rapid metabolism or poor bioavailability which itself may be related to a physicochemical property. Prodrugs are usually prepared by: a) formation of ester, hemi esters, carbonate esters, nitrate esters, amides, hydroxamic acids, carbamates, imines, Mannich bases, phosphates, phosphate esters, and enamines of the active drug, b) functionalizing the drug with azo, glycoside, peptide, and ether functional groups, c) use of aminals, hemiaminals, polymers, salts, complexes, phosphoramides, acetals, hemiacetals, and ketal forms of the drug. For example, see Andrejus Korolkovas's, "*Essentials of Medicinal Chemistry*", John Wiley-Interscience Publications, John Wiley and Sons, New York (1988), pp. 97-118, which is incorporated in its entirety by reference herein.

Furthermore, the methods of the current invention may involve administration of the compounds having Formula (I) by, for example, at least one mode selected from parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, and transdermal.

As previously stated, the "therapeutically effective amount" of the current invention refers to that amount of the compound being administered sufficient to prevent development of or alleviate to some extent one or more of the symptoms of the condition or disorder being treated. Therapeutically effective amounts of compounds having Formula (I) depend on the recipient of the treatment, the disorder being treated and the severity thereof, the composition containing the compound, the time of administration, the route of administration, the duration of treatment, the compound potency, its rate of clearance and whether or not another drug is co-administered. Generally, the methods of the current invention involve administering a dose of the selective Bcl-2 inhibitor ranging from about 0.001 mg/kg to about 1000 mg/kg. In one embodiment, the methods involve administering a dose of selective Bcl-2 inhibitor ranging from about 0.01 mg/kg to about 500 mg/kg. In a further embodiment, the methods involve administering a dose of selective Bcl-2 inhibitor ranging from about 0.1 mg/kg to about 300 mg/kg.

The methods of the current invention may have illustrated improved efficacy in treating disease states such as SLE, lupus nephritis, and Sjogren's Syndrome compared to methods currently known within the art due to the fact that the compounds disclosed herein may selectively inhibit the Bcl-2 protein. The Bcl-2 family of proteins is a group of proteins that have regulatory effects on many developmental and homeostasis functions, such as apoptosis (programmed cell death). The Bcl-2 family includes other proteins include Bcl-$x_L$ and Bcl-w. However, inhibition of the Bcl-$x_L$ protein has been shown to have an adverse impact on platelet counts, in some cases resulting in thrombocytopenia. The selective Bcl-2 inhibitor compounds having Formula (I) have shown a higher binding affinity (as evidenced by lower $K_i$ values) for Bcl-2 compared to other Bcl-2 family proteins, such as Bcl-$x_L$ and Bcl-w. As such, the methods of the current invention provide the advantages of inhibition of the Bcl-2 protein, with a decreased risk of the adverse effects associated with Bcl-$x_L$ and Bcl-w inhibition. The binding affinity for the various proteins is measured as a value of which represents the amount of the compound required to inhibit a physiologic process or compound (such as a protein) by 50%. The selective Bcl-2 compounds used in the methods of the current invention generally have a binding affinity ($K_i$) of less than about 1 micromolar, less than about 500 nanomolar, less than about 400 nanomolar, less than about 300 nanomolar, less than about 200 nanomolar, less than about 100 nanomolar, less than about 50 nanomolar, less than about 25 nanomolar, less than about 10 nanomolar, less than about 5 nanomolar, less than about 1 nanomolar, less than about 900 picomolar, less than about 800 picomolar, less than about 700 picomolar, less than about 600 picomolar, less than about 500 picomolar, less than about 400 picomolar, less than about 300 picomolar, less than about 200 picomolar, and less than about 100 picomolar to Bcl-2.

The selective Bcl-2 inhibitors used in the methods of the current invention selectively bind to and elicit a response on Bcl-2 proteins at much lower concentrations than those required to bind to and elicit a response on Bcl-$x_L$. As such, when the selective Bcl-2 inhibitor is administered to the patient, the inhibitor is more prone to inhibit Bcl-2, rather than Bcl-$x_L$. The selective inhibitors used in the methods of the current invention tend to have a competitive binding affinity ($K_i$) for Bcl-2 that is at least about 500, at least about 1000, at least about 2000, at least about 2500, at least about 3000, at least about 3500, and at least about 4000 times less than the binding affinity for Bcl-$x_L$. As such, even at low concentrations (i.e., picomolar concentrations), the selective Bcl-2 inhibitor will bind to and inhibit the Bcl-2 protein.

Further, the methods of the invention include administering compounds having Formula (I) with or without an excipient. Excipients include, for example, encapsulating materials or additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof.

Excipients for preparation of compositions comprising a compound having Formula (I) to be administered orally in solid dosage form include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl cellulose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, and mixtures thereof. Excipients for preparation of compositions comprising a compound of this invention having Formula (I) to be administered ophthalmically or orally in liquid dosage forms include, for example, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water and mixtures thereof. Excipients for preparation of compositions comprising a compound of this invention having Formula (I) to be administered osmotically include, for example, chlorofluorohydrocarbons, ethanol, water and mixtures thereof. Excipients for preparation of compositions comprising a compound of this invention having Formula (I) to be administered parenterally include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water and mixtures thereof. Excipients for preparation of compositions comprising a compound of this invention having Formula (I) to be administered rectally or vaginally include, for example, cocoa butter, polyethylene glycol, wax and mixtures thereof.

The methods of the current invention encompass methods of administering the selective Bcl-2 inhibitor alone or in combination with other therapeutic products. Many proteins have been implicated in general autoimmune and inflammatory responses. Accordingly, it may be possible to combine the selective Bcl-2 inhibitors with compounds capable of altering the function of other proteins implicated in general autoimmune and inflammatory responses. Examples of proteins associated with autoimmune and inflammatory response include C5, CCL1 (I-309), CCL11 (eotaxin), CCL13 (mcp-4), CCL15 (MIP-1d), CCL16 (HCC-4), CCL17 (TARC), CCL18 (PARC), CCL19, CCL2 (mcp-1), CCL20 (MIP-3a), CCL21 (MIP-2), CCL23 (MPIF-1), CCL24 (MPIF-2 eotaxin-2), CCL25 (TECK), CCL26, CCL3 (MIP-1a), CCL4 (MIP-1b), CCL5 (RANTES), CCL7 (mcp-3), CCL8 (mcp-2), CXCL1, CXCL10 (IP-10), CXCL11 (I-TAC/IP-9), CXCL12 (SDF1), CXCL13, CXCL14, CXCL2, CXCL3, CXCL5 (ENA-78 LIX), CXCL6 (GCP-2), CXCL9, IL13, IL8, CCL13 (mcp-4), CCR1, CCR2, CCR3, CCR4, CCR5, CCR6, CCR7, CCR8, CCR9, CX3CR1, IL8RA, XCR1 (CCXCR1), IFNA2, IL10, IL13, IL17C, IL1A, IL1B, IL1F10, IL1F5, IL1F6, IL1F7, IL1F8, IL1F9, IL22, IL5, IL8, IL9, LTA, LTB, MIF, SCYE1 (endothelial Monocyte-activating cytokine), SPP1, TNF, TNFSF5, IFNA2, IL10RA, IL10RB, IL13, IL13RA1, IL5RA, IL9, IL9R, ABCF1, BCL6, C3, C4A, CEBPB, CRP, ICEBERG, IL1R1, IL1RN, IL8RB, LTB4R, TOLLIP, FADD, IRAK1, IRAK2, MYD88, NCK2, TNFAIP3, TRADD, TRAF1, TRAF2, TRAF3, TRAF4, TRAF5, TRAF6, ACVR1, ACVR1B, ACVR2, ACVR2B, ACVRL1, CD28, CD3E, CD3G, CD3Z, CD69, CD80, CD86, CNR1, CTLA4, CYSLTR1, FCER1A, FCER2, FCGR3A, GPR44, HAVCR2, OPRD1, P2RX7, TLR2, TLR3, TLR4, TLR5, TLR6, TLR7, TLR8, TLR9, TLR10, BLR1, CCL1, CCL2, CCL3, CCL4, CCL5, CCL7, CCL8, CCL11, CCL13, CCL15, CCL16, CCL17, CCL18, CCL19, CCL20, CCL21, CCL22, CCL23, CCL24, CCL25, CCR1, CCR2, CCR3, CCR4, CCR5, CCR6, CCR7, CCR8, CCR9, CX3CL1, CX3CR1, CXCL1, CXCL2, CXCL3, CXCL5, CXCL6, CXCL10, CXCL11, CXCL12, CXCL13, CXCR4, GPR2, SCYE1, SDF2, XCL1, XCL2, XCR1, AMH, AMHR2, BMPR1A, BMPR1B, BMPR2, C19orf10 (IL27w), CERT, CSF1, CSF2, CSF3, DKFZp451J0118, FGF2, GFI1, IFNA1, IFNB1, IFNG, IGF1, IL1A, IL1B, IL1R1, IL1R2, IL2, IL2RA, IL2RB, IL2RG, IL3, IL4, IL4R, IL5, IL5RA, IL6, IL6R, IL6ST, IL7, IL8, IL8RA, IL8RB, IL9, IL9R, IL10, IL10RA, IL10RB, IL11, IL11RA, IL12A, IL12B, IL12RB1, IL12RB2, IL13, IL13RA1, IL13RA2, IL15, IL15RA, IL16, IL17, IL17R, IL18, IL18R1, IL19, IL20, KITLG, LEP, LTA, LTB, LTB4R, LTB4R2, LTBR, MIF, NPPB, PDGFB, TBX21, TDGF1, TGFA, TGFB1, TGFB1I1, TGFB2, TGFB3, TGFBI, TGFBR1, TGFBR2, TGFBR3, TH1L, TNF, TNFRSF1A, TNFRSF1B, TNFRSF7, TNFRSF8, TNFRSF9, TNFRSF11A, TNFRSF21, TNFSF4, TNFSF5, TNFSF6, TNFSF11, VEGF, ZFPM2, RNF110 (ZNF144), FGF family, PLGF, DLL4, and NPR-1.

It should be understood that the invention can be used alone or in combination with an additional agent, e.g., a therapeutic agent, the additional agent being selected by the skilled artisan for its intended purpose. For example, the additional agent can be a therapeutic agent, recognized in the art as being useful to treat the disease or condition being treated by the present invention. The additional agent also can be an agent that imparts a beneficial attribute to the therapeutic composition e.g., an agent that affects the viscosity of the composition.

It should further be understood that the combinations which are to be included within this invention are those combinations comprising treatment with the selective Bcl-2 inhibitors described herein and one or more additional therapeutic agents.

Combinations to treat autoimmune and inflammatory diseases are non-steroidal anti-inflammatory drug(s) also referred to as NSAIDS which include drugs like ibuprofen. Other combinations are corticosteroids including prednisolone; the well known side-effects of steroid use can be reduced or even eliminated by tapering the steroid dose required when treating patients in combination with this invention. Non-limiting examples of therapeutic agents for lupus with this invention can be combined include the following: cytokine suppressive anti-inflammatory drug(s) (CSAIDs); antibodies to or antagonists of other human cytokines or growth factors, for example, TNF, LT, IL-1, IL-2, IL-3, IL-4, IL-5, IL-6, IL-7, IL-8, IL-9, IL-10, IL-12, IL-13, IL-15, IL-16, IL-17A, IL-17F, IL-18, IL-21, IL-22, IL-23, IL-25, IL-33, interferons (for example, alpha, beta, gamma etc), Tweak, BAFF/BLyS, April, chemokines. The invention can be combined with antibodies to cell surface molecules such as CD2, CD3, CD4, CD8, CD16, CD19, CD20, CD22, CD25, CD28, CD30, CD32, CD40, CD45, CD47, CD52, CD54, CD64, CD69, CD72, CD79, CD80 (B7.1), CD86 (B7.2), CD90, CD100, CD200, CTLA, ICOS-1, B7RP, BR3, TACI, BCMA, or their ligands including CD154 (gp39 or CD40L).

The invention may also be combined with agents, such as mycophenolate mofetil (MMF), Cytoxan, Bortezomib, methotrexate, 6-MP, azathioprine sulphasalazine, mesalazine, olsalazine chloroquinine/hydroxychloroquine, penicillamine, aurothiomalate (intramuscular and oral), azathioprine, cochicine, corticosteroids (oral, inhaled and local injection), selective glucocorticoid receptor modulators (SGRMs), O beta-2 adrenoreceptor agonists (salbutamol, terbutaline, salmeterol), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signaling by proinflammatory cytokines such as TNF-α or IL-1 (e.g., IRAK, NIK, IKK, p38 or MAP kinase inhibitors), IL-1β converting enzyme inhibitors, Jak inhibitors, btk inhibitors, syk inhibitors, PKC family inhibitors, TNF-converting enzyme (TACE) inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g., soluble p55 or p75 TNF receptors and the derivatives p75TNFRIgG (Enbrel™ and p55TNFRIgG (Lenercept)), sIL-1RI, sIL-1RII, sIL-6R), antiinflammatory cytokines (e.g., IL-4, IL-6, IL-10, IL-11, IL12, IL-13, IL-17, IL-18, IL-33 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, human recombinant, tramadol HCl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline HCl, sulfadiazine, oxycodone HCl/acetaminophen, olopatadine HCl, misoprostol, naproxen sodium, omeprazole, cyclophosphamide, rituximab, IL-1 TRAP, MRA, CTLA4-IG, IL-18 BP, anti-IL-18, Anti-ILLS, BIRB-796, SCIO-469, VX-702, AMG-548, VX-740, Roflumilast, IC-485, CDC-801, and Mesopram. Combinations include methotrexate or leflunomide, cyclosporine and S1P agonists.

Examples of therapeutic agents for SLE (Lupus) and lupus nephritis, in which the invention can be combined include the following: NSAIDs, for example, diclofenac, naproxen, ibuprofen, piroxicam, indomethacin; COX2 inhibitors, for example, Celecoxib, rofecoxib, valdecoxib; anti-malarials, for example, hydroxychloroquine; Steroids, for example, prednisone, prednisolone, budenoside, dexamethasone; Cytotoxics, for example, azathioprine, cyclophosphamide, mycophenolate mofetil, methotrexate; inhibitors of PDE4 or purine synthesis inhibitor, for example Cellcept. binding proteins incorporated into the methods of the invention, may also be combined with agents such as sulfasalazine, 5-aminosalicylic acid, olsalazine, Imuran and agents which interfere with synthesis, production or action of proinflammatory cytokines such as IL-1, for example, caspase inhibitors like IL-1β converting enzyme inhibitors and IL-1ra. The invention may also be used with T cell signaling inhibitors, for example, tyrosine kinase inhibitors; or molecules that target T cell activation molecules, for example, CTLA-4-IgG or anti-B7 family antibodies, anti-PD-1 family antibodies. The invention, can be combined with IL-11 or anti-cytokine antibodies, for example, fonotolizumab (anti-IFNg antibody), anti-interferon alpha, or anti-receptor receptor antibodies, for example, anti-IL-6 receptor antibody and antibodies to B-cell surface molecules. The invention may also be used with inhibitors of HMGB1, HDGF. The invention may also be used with inhibitors of toll receptors 1, 2, 3, 4, 7, and 9. The invention may also be used with inhibitors of dendritic cell makers BDCA-1, 2 and 3. The invention may also be used with agents which promote regulatory T cell function. The invention may also be used with LJP 394 (abetimus), agents that inhibit complement, for example, anti-C5, anti-C5a, deplete or inactivate B-cells, for example, Rituximab (anti-CD20 antibody), lymphostat-B (anti-BlyS antibody), anti-CD22, TNF antagonists, for example, anti-TNF antibodies, Adalimumab (PCT Publication No. WO 97/29131; HUMIRA), CA2 (REMICADE), CDP 571, TNFR-Ig constructs, (p75TNFRIgG (ENBREL) and p55TNFRIgG (LENERCEPT)) and inhibitors of other bcl-2 family members such as Bcl-$x_L$, Mcl-1, A-1 etc.

Examples of therapeutic agents used to treat Sjogren's Syndrome, that may be combined with the selective Bcl-2 inhibitors include, but are not limited to artificial tears, cyclosporine, cevimeline, pilocarpine, NSAIDs, corticosteroids, immunosuppressants, disease-modifying antirheumatic drugs (DMARDs) such as methotrexate, and hydroxychloroquine.

It may also be possible to combine the selective Bcl-2 inhibitor with a binding protein to further improve the compound to the desired site of action. In one embodiment the binding protein used in the methods of the invention has an on rate constant (Kon) to the one or more targets selected from the group consisting of: at least about $10^2 M^{-1}$ at least about $10^3\ M^{-1}s^{-1}$; at least about $10^4\ M^{-1}s^{-1}$; at least about $10^5\ M^{-1}s^{-1}$; and at least about $10^6\ M^{-1}s^{-1}$, as measured by surface plasmon resonance. In an embodiment, the binding protein of the invention has an on rate constant (Kon) to one or more targets between $10^2\ M^{-1}s^{-1}$ and $10^3 M^{-1}s^{-1}$; between $10^3\ M^{-1}s^{-1}$ and $10^4 M^{-1}s^{-1}$; between $10^4 M^{-1}s^{-1}$ and $10^5 M^{-1}s^{-1}$; or between $10^5 M^{-1}s^{-1}$ and $10^6 M^{-1}s^{-1}$, as measured by surface plasmon resonance.

In another embodiment the binding protein has an off rate constant (Koff) for one or more targets selected from the group consisting of: at most about $10^{-3}s^{-1}$; at most about $10^{-4}s^{-1}$; at most about $10^{-5}s^{-1}$; and at most about $10^{-6}s^{-1}$, as measured by surface plasmon resonance. In an embodiment, the binding protein of the invention has an off rate constant (Koff) to one or more targets of $10^{-3}s^{-1}$ to $10^{-4}s^{-1}$; of $10^{-4}s^{-1}$ to $10^{-5}s^{-1}$; or of $10^{-5}s^{-1}$ to $10^{-6}s^{-1}$, as measured by surface plasmon resonance.

In another embodiment the binding protein has a dissociation constant ($K_D$) to one or more targets selected from the group consisting of: at most about $10^{-7}$ M; at most about $10^{-8}$ M; at most about $10^{-9}$ M; at most about $10^{-10}$ M; at most about $10^{-11}$ M; at most about $10^{-12}$ M; and at most about $10^{-13}$ M. In an embodiment, the binding protein of the invention has a dissociation constant ($K_D$) to its targets of $10^{-7}$ M to $10^{-8}$ M; of $10^{-8}$ M to $10^{-9}$ M; of $10^{-9}$ M to $10^{-10}$ M; of $10^{-10}$ to $10^{-11}$ M; of $10^{-11}$ M to $10^{-12}$ M; or of $10^{-12}$ to M $10^{-13}$ M.

In another aspect, the binding protein is a conjugate comprising a binding protein and an agent selected from the group consisting of an immunoadhesion molecule, an imaging agent, a therapeutic agent, and a cytotoxic agent. Examples of imaging agents include a radiolabel, an enzyme, a fluorescent label, a luminescent label, a bioluminescent label, a magnetic label, and biotin. Examples of radiolabels include 3H, 14C, 35S, 90Y, 99Tc, 111In, 125I, 131I, 177Lu, 166Ho, and 153Sm. In yet another embodiment, the therapeutic or cytotoxic agent is selected from the group consisting of an antimetabolite, an alkylating agent, an antibiotic, a growth factor, a cytokine, an anti-angiogenic agent, an anti-mitotic agent, an anthracycline, toxin, and an apoptotic agent.

In another aspect, the binding protein is a crystallized binding protein, for example, a carrier-free pharmaceutical controlled release crystal. In yet another embodiment, the crystallized binding protein has a greater half life in vivo than the soluble counterpart of the binding protein. In still another embodiment, the crystallized binding protein retains biological activity.

In another embodiment, the binding protein described herein is glycosylated. For example, the glycosylation is a human glycosylation pattern.

Another aspect of the invention pertains to an isolated nucleic acid encoding any one of the binding proteins disclosed herein. A further embodiment provides a vector comprising the isolated nucleic acid disclosed herein wherein the vector is selected from the group consisting of pcDNA; pTT (Durocher et al., *Nucleic Acids Research* 2002, Vol 30, No. 2); pTT3 (pTT with additional multiple cloning site; pEFBOS (Mizushima, S. and Nagata, S., (1990) *Nucleic Acids Research Vol* 18, No. 17); pBV; pJV; pcDNA3.1 TOPO, pEF6 TOPO and pBJ. In an embodiment, the vector is a vector disclosed in U.S. Patent Application Ser. No. 61/021,282.

In another aspect a host cell is transformed with the vector disclosed herein. In an embodiment, the host cell is a prokaryotic cell. In another embodiment, the host cell is *E. Coli*. In a related embodiment the host cell is a eukaryotic cell. In another embodiment, the eukaryotic cell is selected from the group consisting of a protist cell, an animal cell, an avian cell, a plant cell and a fungal cell. In yet another embodiment, the host cell is a mammalian cell including, but not limited to, CHO, COS; NS0, SP2, PER.C6 or a fungal cell such as *Saccharomyces cerevisiae*; or an insect cell such as Sf9.

Another aspect of the invention provides a method of producing a binding protein disclosed herein comprising culturing any one of the host cells also disclosed herein in a culture medium under conditions sufficient to produce the binding protein. In an embodiment, 50%-75% of the binding protein produced by this method is a dual specific tetravalent binding protein. In a particular embodiment, 75%-90% of the binding protein produced by this method is a dual specific tetravalent binding protein. In a particular embodiment, 90%-95% of the binding protein produced is a dual specific tetravalent binding protein.

One embodiment provides a composition for the release of a binding protein wherein the composition comprises a formulation that in turn comprises a crystallized binding protein, as disclosed herein, and an ingredient, and at least one polymeric carrier. For example, the polymeric carrier is a polymer selected from one or more of the group consisting of: poly (acrylic acid), poly(cyanoacrylates), poly(amino acids), poly (anhydrides), poly(depsipeptide), poly(esters), poly(lactic acid), poly(lactic-co-glycolic acid) or PLGA, poly(b-hydroxybutryate), poly(caprolactone), poly(dioxanone); poly (ethylene glycol), poly((hydroxypropyl) methacrylamide, poly[(organo)phosphazene], poly(ortho esters), poly(vinyl alcohol), poly(vinylpyrrolidone), maleic anhydride-alkyl vinyl ether copolymers, pluronic polyols, albumin, alginate, cellulose and cellulose derivatives, collagen, fibrin, gelatin, hyaluronic acid, oligosaccharides, glycaminoglycans, sulfated polysaccharides, blends and copolymers thereof. For example, the ingredient is selected from the group consisting of albumin, sucrose, trehalose, lactitol, gelatin, hydroxypropyl-β-cyclodextrin, methoxypolyethylene glycol and polyethylene glycol. Another embodiment provides a method for treating a mammal comprising the step of administering to the mammal an effective amount of the composition disclosed herein.

The invention also provides a pharmaceutical composition comprising a binding protein, as disclosed herein and a pharmaceutically acceptable carrier. In a further embodiment the pharmaceutical composition comprises at least one additional therapeutic agent for treating a disorder. For example, the additional agent is selected from the group consisting of: a therapeutic agent, an imaging agent, a cytotoxic agent, an angiogenesis inhibitor (including but not limited to an anti-VEGF antibody or a VEGF-trap), a kinase inhibitor (including but not limited to a KDR and a TIE-2 inhibitor), a co-stimulation molecule blocker (including but not limited to anti-B7.1, anti-B7.2, CTLA4-Ig, anti-CD20), an adhesion molecule blocker (including but not limited to an anti-LFA-1 antibody, an anti-E/L selectin antibody, a small molecule inhibitor), an anti-cytokine antibody or functional fragment thereof (including but not limited to an anti-IL-18, an anti- TNF, and an anti-IL-6/cytokine receptor antibody), methotrexate, cyclosporin, rapamycin, FK506, a detectable label or reporter, a TNF antagonist, an antirheumatic, a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog, a cytokine, and a cytokine antagonist.

In another aspect the invention provides a method of treating a patient suffering from a disorder comprising the step of administering any one of the binding proteins disclosed herein before, concurrent, or after the administration of a second agent, as discussed herein. In a particular embodiment the second agent is selected from the group consisting of budenoside, epidermal growth factor, corticosteroids, cyclosporin, sulfasalazine, aminosalicylates, 6-mercaptopurine, azathioprine, metronidazole, lipoxygenase inhibitors, mesalamine, olsalazine, balsalazide, antioxidants, thromboxane inhibitors, IL-1 receptor antagonists, anti-IL-1β mAbs, anti-IL-6 or IL-6 receptor mAbs, growth factors, elastase inhibitors, pyridinyl-imidazole compounds, antibodies or agonists of TNF, LT, IL-1, IL-2, IL-6, IL-7, IL-8, IL-12, IL-13, IL-15, IL-16, IL-18, IL-23, EMAP-II, GM-CSF, FGF, and PDGF, antibodies of CD2, CD3, CD4, CD8, CD-19, CD25, CD28, CD30, CD40, CD45, CD69, CD90 or their ligands, methotrexate, cyclosporin, FK506, rapamycin, mycophenolate mofetil, leflunomide, NSAIDs, ibuprofen, corticosteroids, prednisolone, phosphodiesterase inhibitors, adensosine agonists, antithrombotic agents, complement inhibitors, adrenergic agents, IRAK, NIK, IKK, p38, MAP kinase inhibitors, IL-1β converting enzyme inhibitors, TNFα converting enzyme inhibitors, T-cell signalling inhibitors, metalloproteinase inhibitors, sulfasalazine, azathioprine, 6-mercaptopurines, angiotensin converting enzyme inhibitors, soluble cytokine receptors, soluble p55 TNF receptor, soluble p75 TNF receptor, sIL-1RI, sIL-1RII, sIL-6R, antiinflammatory cytokines, IL-4, IL-10, IL-11, IL-13 and TGFβ.

One aspect of the invention provides at least one anti-idiotype antibody to at least one binding protein of the present invention. The anti-idiotype antibody includes any protein or peptide containing molecule that comprises at least a portion of an immunoglobulin molecule such as, but not limited to, at least one complementarily determining region (CDR) of a heavy or light chain or a ligand binding portion thereof, a heavy chain or light chain variable region, a heavy chain or light chain constant region, a framework region, or any portion thereof, that can be incorporated into a binding protein of the present invention.

A binding protein of the invention can be used alone or in combination to treat such diseases. It should be understood that the binding proteins can be used alone or in combination with an additional agent, e.g., a therapeutic agent, the additional agent being selected by the skilled artisan for its intended purpose. For example, the additional agent can be a therapeutic agent art-recognized as being useful to treat the disease or condition being treated by the antibody of the present invention. The additional agent also can be an agent that imparts a beneficial attribute to the therapeutic composition e.g., an agent which affects the viscosity of the composition.

It should further be understood that the combinations which are to be included within this invention are those combinations useful for their intended purpose. The agents set forth below are illustrative for purposes and not intended to be limited. The combinations, which are part of this invention, can be the antibodies of the present invention and at least one additional agent selected from the lists below. The combination can also include more than one additional agent, e.g., two or three additional agents if the combination is such that the formed composition can perform its intended function.

Combinations to treat autoimmune and inflammatory diseases are non-steroidal anti-inflammatory drug(s) also referred to as NSAIDS which include drugs like ibuprofen. Other combinations are corticosteroids including prednisolone; the well known side-effects of steroid use can be reduced or even eliminated by tapering the steroid dose required when treating patients in combination with the DVD Igs of this invention. Non-limiting examples of therapeutic agents for rheumatoid arthritis with which an antibody, or antibody portion, of the invention can be combined include the following: cytokine suppressive anti-inflammatory drug(s) (CSAIDs); antibodies to or antagonists of other human cytokines or growth factors, for example, TNF, LT, IL-1, IL-2, IL-3, IL-4, IL-5, IL-6, IL-7, IL-8, IL-15, IL-16, IL-18, IL-21, IL-23, interferons, EMAP-II, GM-CSF, FGF, and PDGF. binding proteins incorporated into the methods of the invention, or antigen binding portions thereof, can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Combinations of therapeutic agents may interfere at different points in the autoimmune and subsequent inflammatory cascade; examples include TNF antagonists like chimeric, humanized or human TNF antibodies, Adalimumab, (WO 97/29131), CA2 (Remicade™), CDP 571, and soluble p55 or p75 TNF receptors, derivatives, thereof, (p75TNFR1gG (Enbrel™) or p55TNFR1gG (Lenercept), and also TNFα converting enzyme (TACE) inhibitors; similarly IL-1 inhibitors (Interleukin-1-converting enzyme inhibitors, IL-1RA etc.) may be effective for the same reason. Other combinations include Interleukin 11. Yet another combination includes key players of the autoimmune response which may act parallel to, dependent on or in concert with IL-12 function; especially are IL-18 antagonists including IL-18 antibodies or soluble IL-18 receptors, or IL-18 binding proteins. It has been shown that IL-12 and IL-18 have overlapping but distinct functions and a combination of antagonists to both may be most effective. Yet another combination are non-depleting anti-CD4 inhibitors. Yet other combinations include antagonists of the co-stimulatory pathway CD80 (B7.1) or CD86 (B7.2) including antibodies, soluble receptors or antagonistic ligands.

The binding proteins incorporated into the methods of the invention may also be combined with agents, such as methotrexate, 6-MP, azathioprine sulphasalazine, mesalazine, olsalazine chloroquininehydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNF-α or IL-1 (e.g., IRAK, NIK, IKK, p38 or MAP kinase inhibitors), IL-1β converting enzyme inhibitors, TNFα converting enzyme (TACE) inhibitors, T-cell signalling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g., soluble p55 or p75 TNF receptors and the derivatives p75TNFRIgG (Enbrel™ and p55TNFRIgG (Lenercept)), sIL-1RI, sIL-1RII, sIL-6R), antiinflammatory cytokines (e.g., IL-4, IL-10, IL-11, IL-13 and TGFα), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, human recombinant, tramadol HCl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline HCl, sulfadiazine, oxycodone HCl/acetaminophen, olopatadine HCl, misoprostol, naproxen sodium, omeprazole, cyclophosphamide, rituximab, IL-1 TRAP, MRA, CTLA4-IG, IL-18 BP, anti-IL-18, Anti-ILLS, BIRB-796, SCIO-469, VX-702, AMG-548, VX-740, Roflumilast, IC-485, CDC-801, and Mesopram. Combinations include methotrexate or leflunomide and in moderate or severe rheumatoid arthritis cases, cyclosporine.

Examples of therapeutic agents for SLE (Lupus) and lupus nephritis, in which binding proteins incorporated into the methods of the invention can be combined include the following: NSAIDS, for example, diclofenac, naproxen, ibuprofen, piroxicam, indomethacin; COX2 inhibitors, for example, Celecoxib, rofecoxib, valdecoxib; anti-malarials, for example, hydroxychloroquine; Steroids, for example, prednisone, prednisolone, budenoside, dexamethasone; Cytotoxics, for example, azathioprine, cyclophosphamide, mycophenolate mofetil, methotrexate; inhibitors of PDE4 or purine synthesis inhibitor, for example Cellcept. binding proteins incorporated into the methods of the invention, may also be combined with agents such as sulfasalazine, 5-aminosalicylic acid, olsalazine, Imuran and agents which interfere with synthesis, production or action of proinflammatory cytokines such as IL-1, for example, caspase inhibitors like IL-1β converting enzyme inhibitors and IL-1ra. binding proteins incorporated into the methods of the invention may also be used with T cell signaling inhibitors, for example, tyrosine kinase inhibitors; or molecules that target T cell activation molecules, for example, CTLA-4-IgG or anti-B7 family antibodies, anti-PD-1 family antibodies. binding proteins incorporated into the methods of the invention, can be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. Antibodies of the invention or antigen binding portion thereof may also be used with LJP 394 (abetimus), agents that deplete or inactivate B-cells, for example, Rituximab (anti-CD20 antibody), lymphostat-B (anti-BlyS antibody), TNF antagonists, for example, anti-TNF antibodies, Adalimumab (PCT Publication No. WO 97/29131; HUMIRA), CA2 (REMICADE), CDP 571, TNFR-Ig constructs, (p75TNFRIgG (ENBREL) and p55TNFRIgG (LENERCEPT)) and bcl-2 inhibitors, because bcl-2 overexpression in transgenic mice has been demonstrated to cause a lupus like phenotype (see Marquina, Regina et al., Journal of Immunology (2004), 172(11), 7177-7185), therefore inhibition is expected to have therapeutic effects.

The pharmaceutical compositions of the invention may include a "therapeutically effective amount" or a "prophylactically effective amount" of a binding protein of the invention. A "therapeutically effective amount" refers to an amount effective, at dosages and for periods of time necessary, to achieve the desired therapeutic result. A therapeutically effective amount of the binding protein may be determined by a person skilled in the art and may vary according to factors such as the disease state, age, sex, and weight of the individual, and the ability of the binding protein to elicit a desired response in the individual. A therapeutically effective amount is also one in which any toxic or detrimental effects of the antibody, or antibody portion, are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of a binding protein of the invention is 0.1-20 mg/kg, for example, 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

It will be readily apparent to those skilled in the art that other suitable modifications and adaptations of the methods of the invention described herein are obvious and may be made using suitable equivalents without departing from the scope of the invention or the embodiments disclosed herein. Having now described the present invention in detail, the same will be more clearly understood by reference to the following examples, which are included for purposes of illustration only and are not intended to be limiting of the invention.

Example 1

In Vitro Competitive Binding Affinity Assays for Selective Bcl-2 Inhibitors

In order to test the selective binding affinity for Bcl-2 receptors, in vitro testing of certain selective Bcl-2 inhibitors was performed and compared to a non-selective Bcl-2 inhibitor. Specifically, two compounds: 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide (hereinafter "Compound 1," a selective Bcl-2 inhibitor); and N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (hereinafter "Compound 2," a non-selective Bcl-2 inhibitor) were introduced into murine (FL5.12) cells engineered to depend on either Bcl-2 (FL5.12-Bcl-2) or Bcl-$x_L$ (FL5.12-Bcl-$x_L$) for survival. These compounds as well as additional compounds listed in Table 1A. These compounds and the additional compounds in Tables 1A were also introduced into human tumor cell lines that have been previously demonstrated to be predominantly dependent on either Bcl-2 (RS4;11) or Bcl-xL (H146) for survival, and the effect of the compounds measured. A comparison of the binding affinity for each of the compounds was performed to determine target affinity, as measured by Time-Resolved Fluorescence Resonance Energy Transfer (TR FRET). Testing was also performed to determine the effective concentration required to inhibit at least 50% of the target protein, as measured by the EC50 value, for all compounds (Ref. WO2010/138588A2). The results of the in vitro testing for the compounds in Table 1A are provided in Table 1B below:

TABLE 1A

Listing of Compound Number and the associated compound name

| Compound Number | Name |
|---|---|
| 1 | 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide |
| 2 | N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide |
| 3 | 3 is 4-(4-{[2-(4-chlorophenyl)-4,4-dimethylcyclohex-1-en-1-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide. |
| 4 | Trans-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide |
| 5 | Trans-4-(4-{[2-(4-chlorophenyl)-4,4-dimethylcyclohex-1-en-1-yl]methyl}piperazin-1-yl)-N-(4-{[(4-methoxycyclohexyl)methyl]amino}-3-nitrophenyl]sulfonyl]-2-(1H-pyrrolo[2,3-b]pyridin-5-yloxy)benzamide |
| 6 | Trans-N-({5-chloro-6-[(4-hydroxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide |
| 7 | 4-(4-{[2-(4-chlorophenyl)-4,4-dimethylcyclohex-1-en-1-yl]methyl}piperazin-1-yl)-N-{[4-({[(2S)-4-cyclopropylmorpholin-2-yl]methyl}amino)-3-nitrophenyl]sulfonyl}-2-(1H-pyrrolo[2,3-b]pyridin-5-yloxy)benzamide |

TABLE 1A-continued

Listing of Compound Number and the associated compound name

| Compound Number | Name |
|---|---|
| 8 | 4-(4-{[2-(4-chlorophenyl)-4,4-dimethylcyclohex-1-en-1-yl]methyl}piperazin-1-yl)-N-[(4{[(cis-4-hydroxy-4-methylcyclohexyl)methyl]amino}-3-nitrophenyl)sulfonyl]-2-(1H-pyrrolo[2,3-b]pyridin-5-yloxy)benzamide |
| 9 | 4-(4-{[2-(4-chlorophenyl)-4,4-dimethylcyclohex-1-en-1-yl]methyl}piperazin-1-yl)-N-[(4-{[(trans-4-hydroxy-4-methylcyclohexyl)methyl]amino}-3-nitrophenyl)sulfonyl]-2-(1H-pyrrolo[2,3-b]pyridin-5-yloxy)benzamide |
| 10 | 4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)-2-(1H-pyrrolo[2,3-b]pyridin-5-yloxy)benzamide |
| 11 | N-[(3-chloro-4-{[4-fluoro-1-(oxetan-3-yl)piperidin-4-yl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide |
| 12 | N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide |
| 13 | N-[(5-chloro-6-{[4-fluoro-1-(oxetan-3-yl)piperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide |
| 14 | N-({5-chloro-6-[(trans-4-hydroxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-[(6-fluoro-1H-indazol-4-yl)oxy]benzamide |
| 15 | N-({3-chloro-4-[(4-fluorotetrahydro-2H-pyran-4-yl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide |
| 16 | 4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-(1H-pyrrolo[2,3-b]pyridin-5-yloxy)benzamide |
| 17 | Trans-2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)benzamide |

TABLE 1B

Binding affinities for Bcl-2 family proteins and cellular efficacy in Bcl-2 or Bcl-$x_L$ dependent cell lines for representative compounds.

| | Target Affinity TR FRET, [nM] | | | | Cellular Efficacy, $EC_{50}$, [nM] | | | |
|---|---|---|---|---|---|---|---|---|
| | | | | | FL5.12, 3% FBS | | Human Tumor Cell Lines, 10% HS | |
| | | | | | | | RS4; 11 | H146 |
| Compound | Bcl-2 | Bcl-$x_L$ | Bcl-w | Mcl-1 | Bcl-2 | Bcl-$x_L$ | (Bcl-2) | (Bcl-$x_L$) |
| 2 | 0.04 | 0.05 | 7 | >224 | 20 | 13 | 110 | 75 |
| 1 | <0.01 | 48 | 21 | >440 | 4 | 261 | 12 | 3,600 |
| 3 | 0.119 | 151 | | 111 | 12 | 1060 | 41 | >5000 |
| 4 | <0.01 | 7.2 | | | 1.2 | 70 | 32 | >5000 |
| 5 | <0.01 | 126 | | | 1.2 | 67 | 8 | >5000 |
| 6 | <0.01 | 27 | | >224 | | | 23 | 3657 |
| 7 | <0.01 | 9.4 | | | | | 2.7 | 926 |
| 8 | <0.01 | 16 | 405 | >440 | | | 4.0 | 3343 |
| 9 | <0.01 | 16 | 227 | >440 | | | 2.5 | 3757 |
| 10 | 0.02 | 21 | | >440 | 12 | 273 | 31 | 2904 |
| 11 | <0.01 | 12 | | | | | 12 | 2994 |
| 12 | <0.01 | 23 | | | 2.3 | 59 | 17 | 2747 |
| 13 | <0.01 | 9 | 167 | >440 | | | 7 | 3158 |
| 14 | <0.01 | 20 | | | | | 22 | 3543 |
| 15 | <0.01 | 61 | | | | | 35 | >5000 |
| 16 | <0.01 | 15 | | | 0.7 | 31 | 2.1 | 3931 |
| 17 | <0.01 | 12 | 357 | >440 | 4.0 | 65 | 17 | 3236 |

As illustrated in Table 1B, Compound 1 has picomolar affinity for Bcl-2, but >4,000-fold lower affinity for Bcl-$x_L$ in competitive binding assays. The significantly greater affinity for Bcl-2, as compared to Bcl-$x_L$ suggests a selective binding affinity. Additionally, Compound 1 potently killed FL5.12-Bcl-2 cells (EC50=4 nM), but exhibited much weaker activity against FL5.12-Bcl-$x_L$ cells (EC50=261 nM), further indicating functional selectivity for Bcl-2. Additionally, Compound 1 potently killed RS4;11 cells (EC50=12 nM), but exhibited much weaker activity against H146 cells (EC50=3600 nM), further indicating functional selectivity for Bcl-2. As also shown in Table 1B, additional compounds show selective binding affinity for Bcl-2 over Bcl-xL and other Bcl-2 family proteins. Additional compounds also inhibit Bcl-2 dependent cell lines than Bcl-xL dependent cell lines. Cellular inhibition and killing by Compound 1 displays the hallmarks of apoptotic cell death, including rapid cytochrome c release, caspase-3 and -7 activation, and membrane phosphatidylserine (PS) externalization. Compound 1 cell killing is caspase-dependent and can be ablated by the pan caspase inhibitor z-VAD-fmk. Cell killing is completely inhibited when Bax and Bak, the essential downstream effectors, are genetically ablated. These data indicate that Compound 1 potently and selectively disrupts Bcl-2 protein-protein interactions and induces mechanism-based cell death in cells dependent on Bcl-2 for survival.

Example 2

Pharmacodynamic Response with Bcl-2 Selective Inhibitor Compound 1

It is known within the art that inhibition of certain members of the Bcl-2 family of proteins may induce dose-limiting thrombocytopenia. The dose-limiting thrombocytopenia that severely limited the therapeutic use of some non-selective Bcl-2 inhibitors for autoimmune indications is thought to be due to inhibition of Bcl-$x_L$ (See Mason, K. D., et al., *Programmed anuclear cell death delimits platelet life span*. CELL, 2007. 128(6): p. 1173-86). Therefore, the effect of the Bcl-2 selective Bcl-$x_L$ sparing Compound 1, on peripheral blood immune cells and platelets was evaluated in (NZB×NZW)F1 mice. Mice were treated four days with Compound 1 (1-100 mg/kg, orally every day) and cell numbers were measured with a Cell Dyn hematology analyzer. As shown in FIG. 1B, Compound 1 resulted in a dose dependent decrease in lymphocytes while maintaining normal platelet counts compared to control. As shown in FIG. 1A, Compound 2 also resulted in a decrease in lymphocytes, but caused a significant decrease in platelet counts. These data are consistent with the in vitro selectivity profile and underscore the essential role of Bcl-2 on lymphocyte and Bcl-$x_L$ on platelet survival respectively. The data also establish lymphopenia as a convenient mechanistic biomarker for Compound 1.

The effect of the Bcl-2 selective Bcl-$x_L$ sparing compounds on peripheral blood immune cells was also evaluated in C57BL6 mice. Mice were treated four days with individual compounds (100 mg/kg, orally every day) and cell numbers were measured with a Cell Dyn hematology analyzer. As shown in Table 2, treatment with all compounds resulted in a decrease in lymphocytes after a single oral dose of 100 mg/kg and after 4 oral doses of 100 mg/kg.

TABLE 2

Lymphocyte numbers and degree of reduction in C57BL/6 mice treated with 1 and 4 doses of a Bcl-2 selective inhibitor (100 mg/kg)

| | Day 1 | | Day 4 | |
|---|---|---|---|---|
| Compound | Lymphocytes (×10⁶) | % Reduction vs. Vehicle | lymphocytes (×10⁶) | % Reduction vs. Vehicle |
| 1 | 1.38 | 83 | 1.32 | 83 |
| 3 | 2.3 | 63 | 1.34 | 79 |
| 4 | 2.62 | 57 | 1.72 | 73 |
| 5 | 0.98 | 84 | 1.02 | 84 |
| 6 | 1.91 | 69 | 0.98 | 85 |
| 7 | 0.89 | 85 | 0.95 | 85 |
| 8 | 0.92 | 85 | 1.02 | 84 |
| 9 | 0.75 | 88 | 0.88 | 86 |

TABLE 2-continued

Lymphocyte numbers and degree of reduction in C57BL/6 mice treated with 1 and 4 doses of a Bcl-2 selective inhibitor (100 mg/kg)

| Compound | Day 1 | | Day 4 | |
|---|---|---|---|---|
| | Lymphocytes ($\times 10^6$) | % Reduction vs. Vehicle | lymphocytes ($\times 10^6$) | % Reduction vs. Vehicle |
| 10 | 2.25 | 65 | 2.48 | 71 |
| 11 | 1.76 | 73 | 1.71 | 80 |
| 12 | 1.44 | 78 | 2.21 | 74 |
| 13 | 2.32 | 64 | 2.61 | 70 |
| 14 | 3.02 | 54 | 2.33 | 73 |
| 15 | 1.85 | 72 | 1.65 | 81 |
| 16 | 1.77 | 73 | 1.99 | 77 |
| 17 | 1.84 | 77 | 1.30 | 83 |

Example 3

Pharmacodynamic Response with Bcl-2 Selective Inhibitor Compound 3

Figure 2:
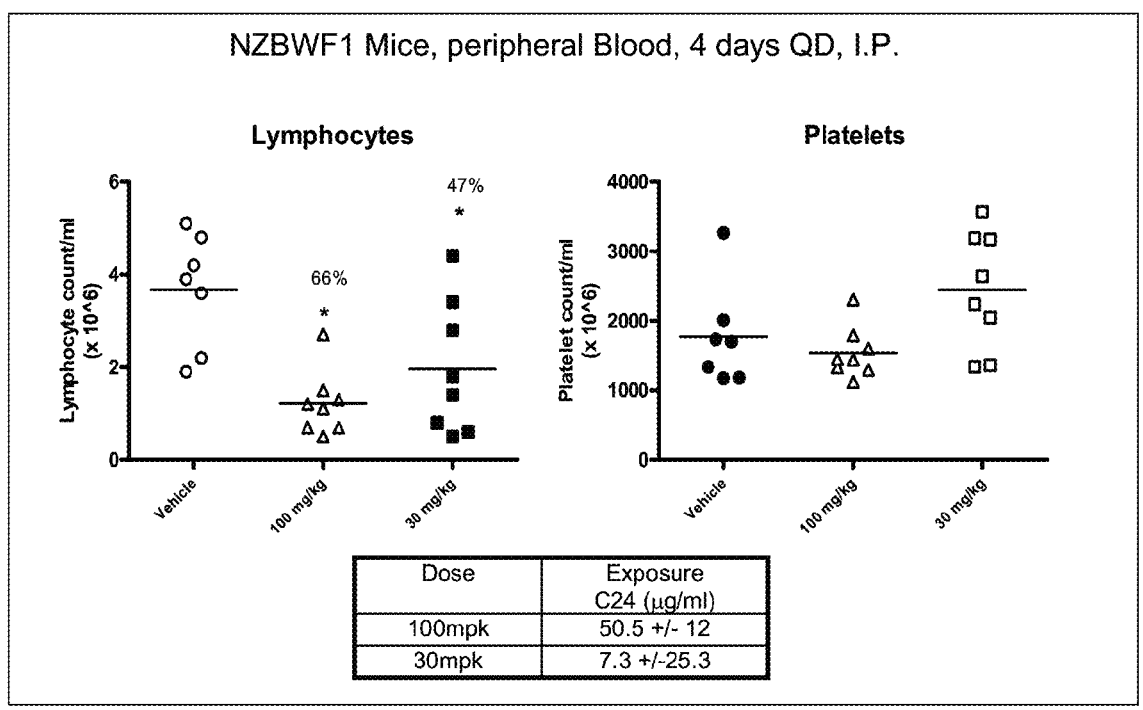
FIG. 2 illustrates the effect of treatment with a selective Bcl-2 inhibitor (Compound 3) in mice on lymphocytes and platelets. Specifically.
Figure 3:
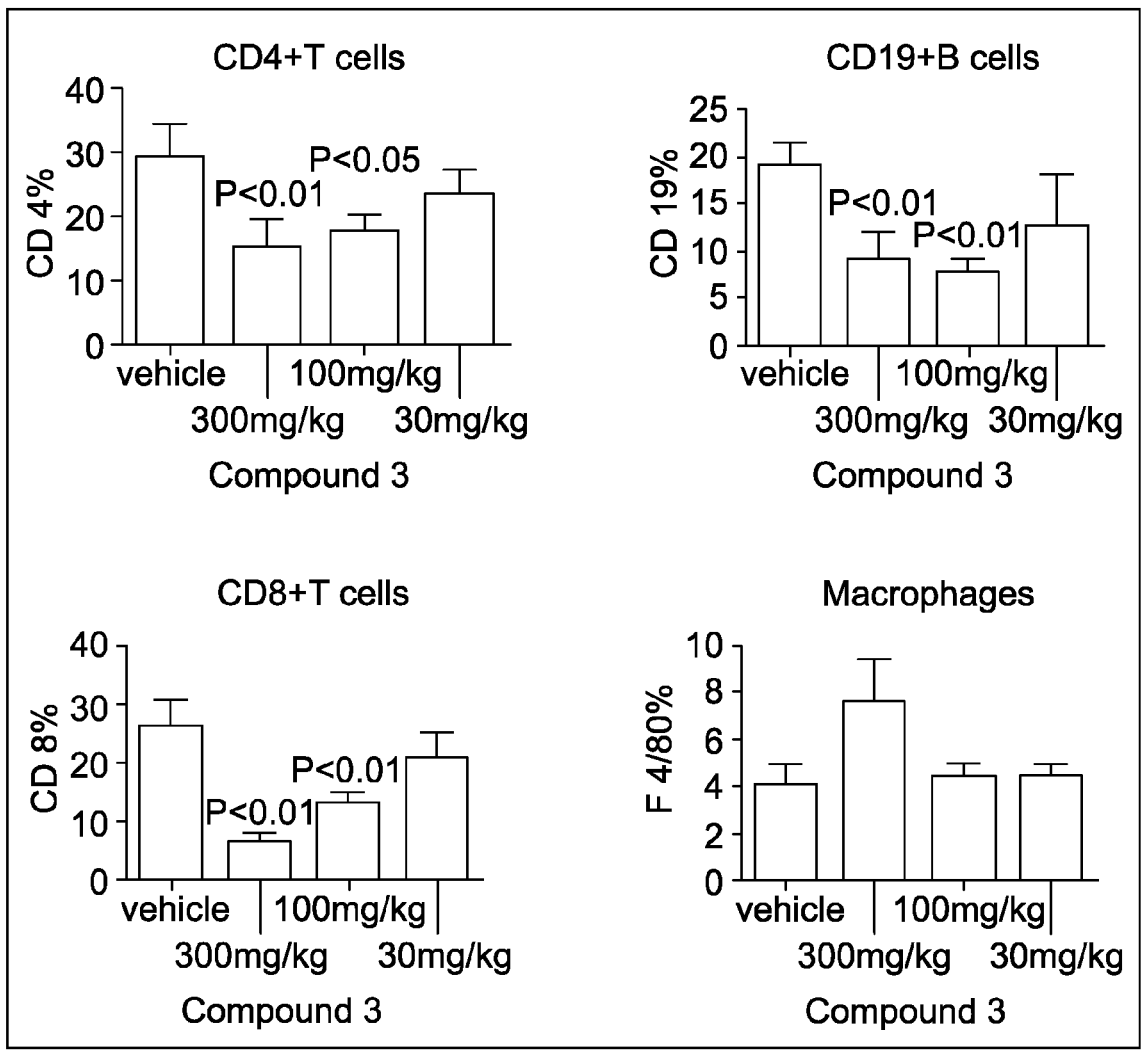
FIG. 3 illustrates the reduction in T cells and B cells in mice treated with various doses of a selective Bcl-2 inhibitor (Compound 3), as compared to treatment with phosal vehicle. Specifically.

An experiment was performed to evaluate the effect of an additional selective Bcl-2 inhibitor compound, 4-(4-{[2-(4-chlorophenyl)-4,4-dimethylcyclohex-1-en-1-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide, hereinafter "Compound 3," on immune cells and platelets, as evaluated in (NZB×NZW)F1 mice. Mice were treated four days with Compound 3 (doses of 30 mg/kg and 100 mg/kg, administered by intraperitoneal injection every day) and cell numbers were measured with a Cell Dyn hematology analyzer. Exposure of the compound was calculated 24 hours after the last dose. The results of this experiment are illustrated in FIGS. 2 and 3. As shown in FIG. 2, Compound 3 resulted in a dose dependent decrease in lymphocytes while maintaining normal platelet counts compared to a phosal vehicle control. Specifically, the 30 mg/kg and 100 mg/kg doses of Compound 3 resulted in lymphocyte reductions of 47% and 66%, respectively, without significantly affecting platelet counts. Moreover, FIG. 3 illustrates a statistically significant decrease in CD4+ T cells, CD8+ T cells, and CD19+ B cells, for doses of Compound 3 comprising 100 mg/kg and 300 mg/kg. As such, these pharmacodynamic studies illustrate the ability of Compound 3, a selective Bcl-2 inhibitor to effectively reduce lymphocytes, without the adverse effects associated with non-selective Bcl-2 inhibitors.

Example 4

Treatment with Selective Bcl-2 Inhibitors in the Spontaneous Murine Model of Lupus To demonstrate that Compound 1 and Compound 17 are viable therapeutics for human SLE or lupus nephritis, experiments were conducted in the spontaneous (NZB×NZW)F$_1$ murine model of lupus. (See Liu, K. and C. Mohan, What do mouse models teach us about human SLE? Clin Immunol, 2006. 119(2): p. 123-30) This model has been well-characterized with respect to the patho-physiological changes analogous to those of human SLE. They exhibit a female bias in disease prevalence and high serum titers of IgG anti-ds-DNA antibodies that are hallmarks of human SLE, with accompanying renal IgG deposition. Renal histopathological changes include severe glomerulonephritis, mesangial and peripheral proliferative changes, capillary membrane thickening, tubular atrophy, and infiltration of lymphocytes and monocytesmacrophages as in the majority of human SLE patients. These changes result in disruption of kidney function as evidenced by severe proteinuria (PU) greater than 300 mg/dL as measured by albumin sticks, followed by mortality as measured by survival. Two of the clinical benchmarks for lupus nephritis, MMF and cyclophosphamide, have been shown to decrease autoantibody titer, improve renal pathology, delay onset of severe proteinuria and prolong survival in these animals. (See Gelfand, M. C. and A. D. Steinberg, Therapeutic studies in NZB-W mice. II. Relative efficacy of azathioprine, cyclophosphamide and methylprednisolone. Arthritis Rheum, 1972. 15(3): p. 247-52; and Ramos, M. A., et al., Modulation of autoantibody production by mycophenolate mofetil: effects on the development of SLE in (NZB×NZW)F1 mice. Nephrol Dial Transplant, 2003. 18(5): p. 878-83)

(NZB×NZW)F1 females were purchased from The Jackson Laboratory (Bar Harbor, Me., USA) and maintained in a conventional animal housing facility throughout the experiment. Anti-ds DNA was measured in 25-week-old (NZB×NZW)F1 mice and animals were distributed to various treatment groups (N=14-18/group) at 26 weeks of age and administered daily oral doses of Compound 1 or Compound 17 ranging from 1 to 100 mg/kg, or mycophenolate mofetil (MMF) at a dose of 100 mg/kg. Proteinuria (PU) and survival were monitored weekly, followed by biweekly measurement of lymphocyte and platelet counts, and anti-ds DNA production. PK parameters were also measured throughout the study. Impact on IgG deposition and renal pathology were assessed at the conclusion of the study. Severe PU was defined by two consecutive weekly measurements of PU≥300 mg/dl using Albustix test strips (VWR). When mice became moribund, they were sacrificed according to Institutional Animal Care and Use Committee protocols. PU and survival data were presented as Kaplan-Meyer survival curves using Graphpad Prism software and group differences were considered significant at the level of $p<0.05$. Histologic scores were analyzed using ANOVA analysis. Anti-ds DNA were analyzed using one-way ANOVA analysis and Tukey post-test.

Figure 4:
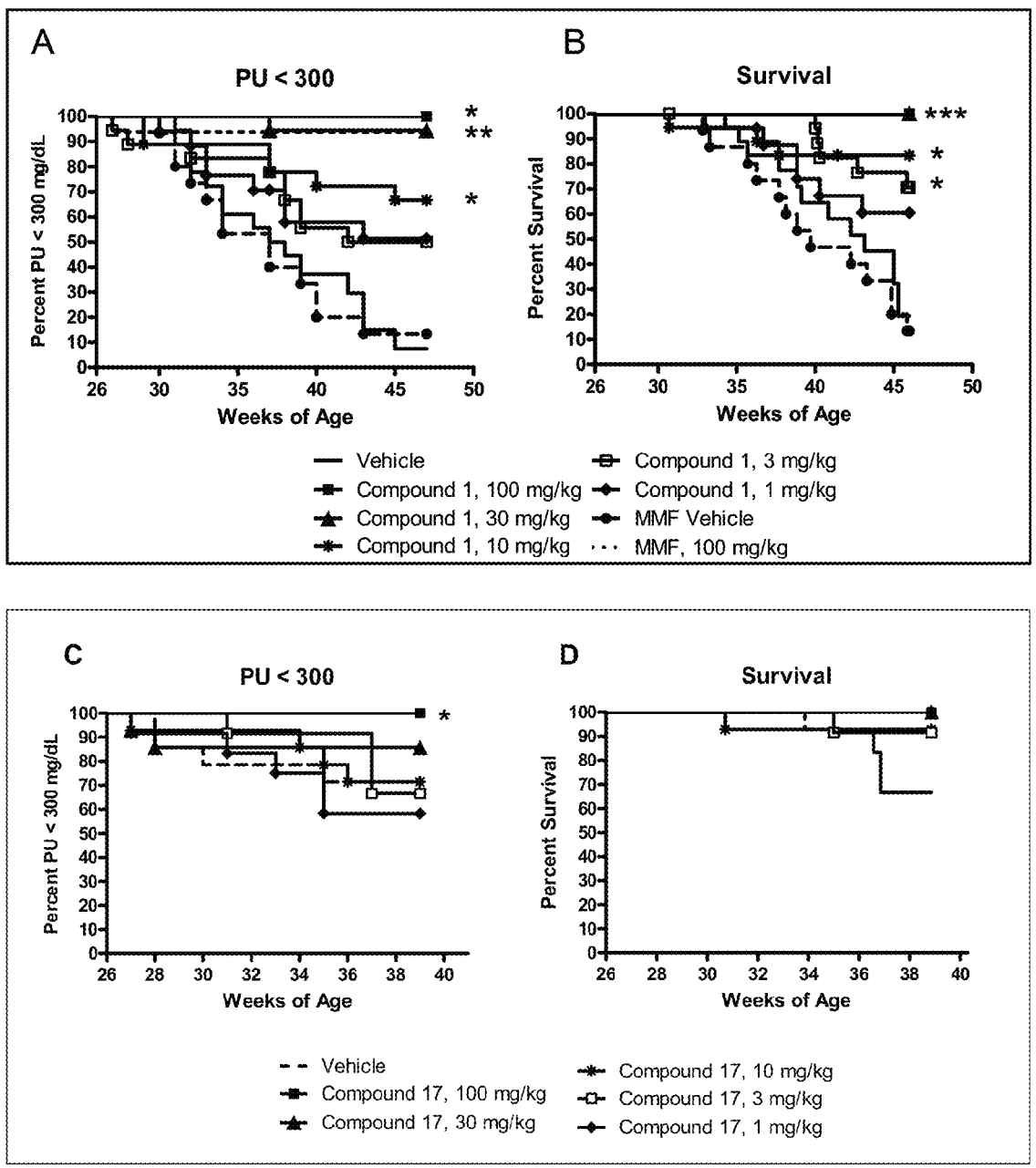
FIG. 4 illustrates the efficacy of treatment with a selective Bcl-2 inhibitor (Compound 1) in a spontaneous (NZBxNZW) F$_1$ murine model of lupus as assessed by (A) incidence of severe proteinuria (PU≥300 mg/dL) and (B) Kaplan-Meier cumulative survival.

As illustrated in FIG. 4A, treatment with Compound 1 resulted in the delayed onset of severe PU in a dose-dependent fashion, reaching significance at 10, 30 and 100 mg/kg. In addition, treatment with Compound 1 at 3, 10, 30, and 100 mg/kg significantly prolonged survival as illustrated in FIG. 4B and Table 3A. These data also correlated with a dose-dependent and sustained reduction of lymphocytes in peripheral blood, with 30 and 100 mg/kg dosing of Compound 1 both resulting in 70% lymphopenia. Efficacy on both disease endpoints at the 30 mg/kg dose of Compound 1 was comparable to MMF treatment at 100 mg/kg. The exposure in this model at the 30 mg/kg dosing was 40 μg·h/mL. Similar efficacy results were also obtained for Compound 17 as illustrated in FIG. 4 C, D and Table 3B.

TABLE 3A

Compound 1 PU and Survival Efficacy at Week 47

| Treatment Groups | % Mice with PU < 300 mg/dL | % Survival |
|---|---|---|
| Compound 1 | | |
| VehicleControl | 7 | 19 |
| 1 mg/kg | 51 | 60 |
| 3 mg/kg | 50 | 70* |
| 10 mg/kg | 66* | 83* |
| 30 mg/kg | 94* | 100* |
| 100 mg/kg | 100* | 100* |

TABLE 3A-continued

Compound 1 PU and Survival Efficacy at Week 47

| Treatment Groups | % Mice with PU < 300 mg/dL | % Survival |
|---|---|---|
| MMF | | |
| Vehicle Control | 13 | 13 |
| 100 mg/kg | 94* | 100* |

*P < 0.05

TABLE 3b

Compound 17 PU and Survival Efficacy at Week 39

| Treatment Groups Compound 17 | % Mice with PU < 300 mg/dL | % Survival |
|---|---|---|
| Vehicle Control | 71 | 93 |
| 1 mg/kg | 58 | 67 |
| 3 mg/kg | 67 | 92 |
| 10 mg/kg | 71 | 93 |
| 30 mg/kg | 86 | 100 |
| 100 mg/kg | 100* | 100 |

*P < 0.05

Example 5

Effect of Selective Bcl-2 Inhibitors on Anti-Ds DNA Titer in Spontaneous Mouse Model It is believed that Compound 1 triggers apoptosis of lymphocytes that are responsible for production of antibodies, which play a role in the progression of systemic lupus erythematosus, as well as Sjogren's Syndrome. As such, it was hypothesized that treatment with Compound 1 would decrease anti-ds DNA titer. Specifically, anti-dsDNA antibody levels were measured by ELISA and assigned arbitrary activity unit concentrations per ml relative to a standard plasma pool derived from proteinuric 9-10 month old NZBW mice. ELISA assay was performed by coating plates with poly-L-lysine followed by calf-*thymus* DNA. Diluted mouse plasma was incubated and developed using anti-IgG HRP conjugated antibodies and the mean OD from duplicate wells was compared to a titrated standard curve of pooled high tittered anti-dsDNA plasma. The undiluted standard plasma pool was arbitrarily assigned a value of 1000 anti-dsDNA Units/ml. A linear regression analysis was then used to calculate the relative units of a given sample multiplied by the given dilution factor.

Figure 5:
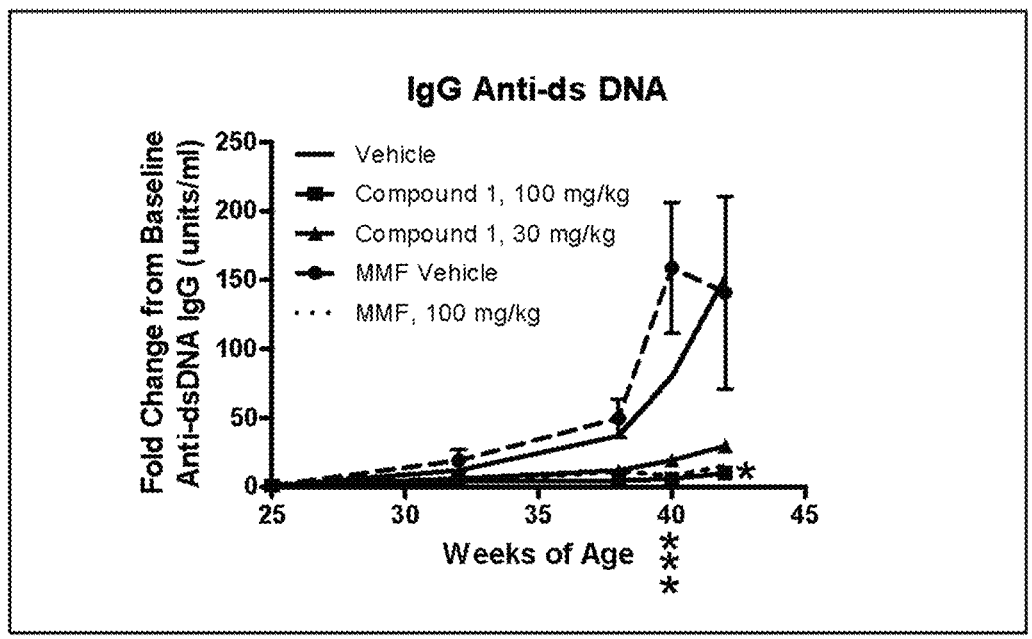
FIG. 5 illustrates the effect of treatment with a selective Bcl-2 inhibitor (Compound 1), as well as treatment with mycophenolate mofetil (MMF), on inhibition of anti-ds DNA titer production in a spontaneous SLE model for Compound 1 at 30 mg/kg and 100 mg/kg, and MMF at 100 mg/kg compared to vehicle controls. Asterisks represent statistical significance of P<0.05.

The results of this experiment are illustrated in FIG. 5. In control animals, the IgG anti-ds DNA levels increased from an average of <100 unit/mL at baseline (25 week) to an average of ~600 unit/mL by week 32, with a further increase to ~1800 unit/mL by week 40. The apparent increase in anti-ds DNA titer occurred with a concomitant increase in disease severity and incidence as measured by PU and survival. There was no appreciable reduction on anti-ds DNA titer in the groups treated with 1, 3 and 10 mg/kg of Compound 1. However, at week 40, treatment with Compound 1 at 30 and 100 mg/kg significantly inhibited the increase in anti-ds DNA titer compared to vehicle control, comparable to the effect observed with MMF.

Example 6

Infiltration of Renal Tissue with Selective Bcl-2 Inhibitors

Figure 6:
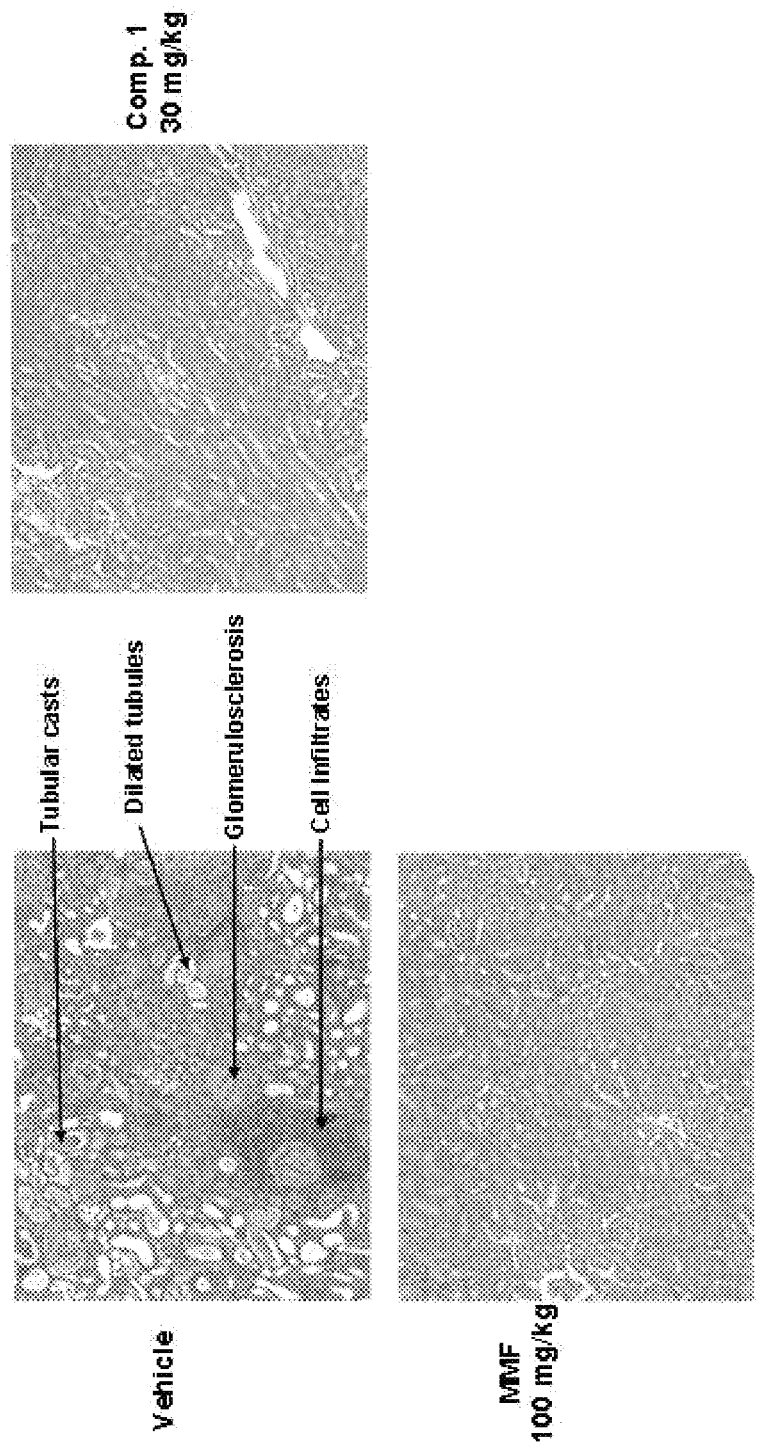
FIG. 6 illustrates the representative images demonstrating a reduction of infiltrates in renal tissue in spontaneous lupus nephritis mice, after dosing with a selective Bcl-2 inhibitor (Compound 1), as evidenced by histological assessment. Magnification 200×.
Figure 7:
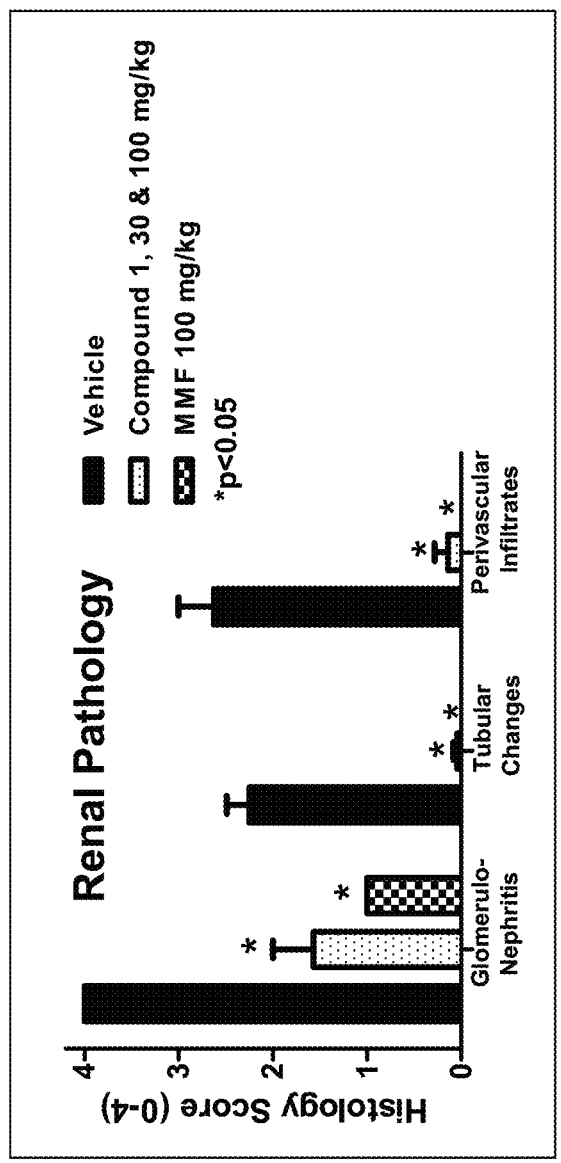
FIG. 7 illustrates changes in histology scores for renal tissue treated with one of three treatment regimens: treatment with the vehicle, treatment with Compound 1 at a dose of 30 mg/kg and 100 mg/kg, and treatment with MMF at a dose of 100 mg/kg, as they related to histological signs of glomerulonephritis, tubular changes, and perivascular infiltrates. Specifically.

An experiment was performed to determine the extent to which the selective Bcl-2 inhibitors infiltrated the kidney tissue. Specifically, a histologic assessment of the penetration of selective Bcl-2 inhibitors into the renal tissue of spontaneous murine model for lupus was performed. The spontaneous murine model of lupus, as described in Example 3, was used for the histological assessment described herein. The kidneys were bisected and then fixed in 10% neutral-buffered formalin or cryopreserved (snap frozen). For H&E staining, 5-μm sections from paraffin-embedded tissues were semiquantitatively scored (0-4) by an experienced pathologist for glomerulonephritis and tubular changes (dilation and casts). For IgG immunohistochemistry, 5-μm cryosections were fixed with acetone, washed, and blocked with 10% normal goat serum. Sections were then incubated with FITC-conjugated goat anti-mouse IgG (Cappel/ICN Pharmaceuticals) or negative control HRP-goat IgG (Jackson ImmunoResearch Laboratories) and coverslipped using Vectashield with 4',6-diamidino-2-phenylindole (Vector Laboratories). Sections were evaluated for severity of IgG deposition using a semiquantitative scoring system (from 0-4). To identify for B and T cells, immunohistochemistry for CD45R (B cells) and CD3 (T cells) was completed on paraffin sections. FIGS. 6 and 7 illustrate the results of the histological assessment, and FIG. 8 illustrates the effect of selective Bcl-2 inhibitor treatment on IgG deposition, B cells, and T cells in the kidneys.

As illustrated in FIG. 6, phosal vehicle dosed spontaneous lupus nephritis mice typically had extensive renal infiltrates, as evidenced by tubular casts, dilated tubules, glomerulocle-rosis, and cell infiltrates. Renal tissue infiltrates in spontaneous lupus nephritis mice dosed with 30 or 100 mg/kg of Compound 1 were small, discrete and less frequent. In addition, FIG. 7 includes a bar graph illustrating the difference in histology scores for renal tissue that was not treated, tissue treated with Compound 1 at doses of 30 mg/kg and 100 mg/kg, and tissue treated with MMF at a dose of 100 mg/kg. As noted in FIG. 7, the tissue treated with Compound 1 at doses of 30 mg/kg and 100 mg/kg showed a statistically significant improvement (decrease in severity) in histology scores, as they pertained to glomerulonephritis, tubular changes, and perivascular infiltrates.

Figure 8:
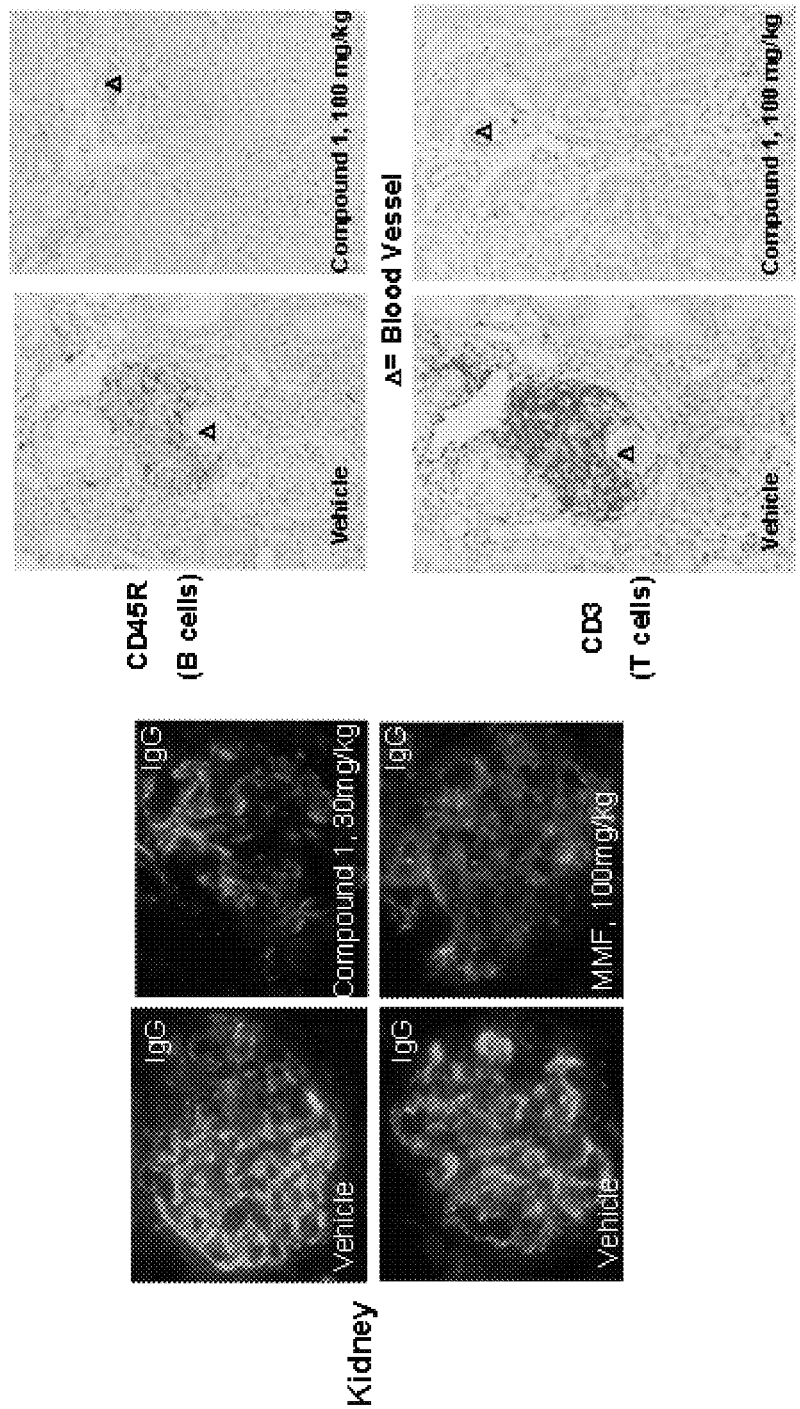
FIG. 8 illustrates immunoglobulin G (IgG), B cell, and T cell deposition in renal tissue for spontaneous lupus nephritis mice dosed with phosal vehicle, Compound 1 at doses of 30 mg/kg and 100 mg/kg, and MMF at a dose of 100 mg/kg. Specifically, mice treated with Compound 1 showed decreased deposition of IgG, B cells, and T cells, as compared to phosal vehicle.

Further, FIG. 8 illustrates a decrease in IgG deposition in renal tissue treated with Compound 1 at a dose of 30 mg/kg, as well as decreases in B cell and T cell numbers in renal tissue treated with Compound 1 at a dose of 100 mg/kg. Accordingly, the selective Bcl-2 inhibitor, Compound 1, illustrated an amelioration in the deposition of IgG, infiltration and expansion of B cells, and T cells in renal tissue, and also resulted in a statistically significant improvement in histological scores, as compared to treatment with phosal vehicle.

Example 7

Treatment with a Selective Bcl-2 Inhibitor in an Interferon-α Accelerated Lupus Model Due to the fact that studies in the spontaneous (NZB× NZW)F1 model require 6-8 months to complete due to the slow development of disease manifestations, additional testing of selective Bcl-2 inhibitors was performed in alternative models. To provide a faster measurement, an IFNα-accelerated lupus model was established and used to assess the therapeutic potential of Compound 1. An increased IFNα serum level and a concomitant enhanced "IFNα responsive gene signature" has been reported in a subset of SLE patients (See Kwok, S. K., et al., Dysfunctional interferon-alpha production by peripheral plasmacytoid dendritic cells upon Toll-like receptor-9 stimulation in patients with systemic lupus erythematosus. *Arthritis Res Ther,* 2008. 10(2): p. R29; and Rong, Z., et al., Effect of Interferon-alpha in systemic lupus erythematosus (SLE) serum on the differentiation and maturation of dendritic cells derived from CD34+ hematopoietic precursor cells. *Journal of Nanjing Medical University,* 2009. 23(6): p. 380-385) A drug-induced SLE-like disease has also been reported in HCV patients given IFNα therapy. (See Wilson, L. E., et al., Autoimmune disease complicating antiviral therapy for hepatitis C virus infection. *Semin Arthritis Rheum,* 2002. 32(3): p. 163-73) These observations underscore an important role for IFNα signaling in SLE pathogenesis.

To recapitulate the IFNα effect in rodents, the inventors and others in the art (See Bardwell, P. D., et al., The Bcl-2 family antagonist ABT-737 significantly inhibits multiple animal models of autoimmunity. J Immunol, 2009. 182(12): p. 7482-9; and Mathian, A., et al., IFN-alpha induces early lethal lupus in preautoimmune (New Zealand Black×New Zealand White) F1 but not in BALBc mice. *J Immunol,* 2005. 174(5): p. 2499-506) established an adenovirus-mediated IFNα-induced (NZB×NZW)F$_1$ lupus model, which features a rapid and severe disease with many characteristics similar to the spontaneous (NZB×NZW)F$_1$ lupus mice, including death due to severe glomerulonephritis. However, there are also differences between these two models: (1) a supraphysiological production of IFNα in blood is required for severe lupus nephritis (see Mathian, A., et al., IFN-alpha induces early lethal lupus in preautoimmune (New Zealand Black×New Zealand White) F1 but not in BALBc mice. J Immunol, 2005. 174(5): p. 2499-506); (2) a sustained, >50% peripheral blood lymphopenia is observed within 2 weeks of IFNα treatment; (3) the augmentation of disease is not associated with a robust increase in immoral autoimmunity such as anti-ds DNA titer as observed in spontaneous (NZB×NZW)F$_1$ mice. The data collected in this experiment was consistent with recent findings in IFN-α adenovirus treated B6.Sle123 mice (See Fairhurst, A. M., et al., Systemic IFN-alpha drives kidney nephritis in B6.Sle123 mice. *Eur J Immunol.,* 2008. 38(7): p. 1948-60) and supported the idea that the major effect of IFNα treatment on disease pathogenesis in this model is to drive end organ disease, possibly through activation of many types of immune cells and production of proinflammatory cytokines.

Compound 1, MMF and BAFFR3-Ig (a surrogate for Belimumab) were evaluated in the IFNα-induced (NZB×NZW) F$_1$ model. BAFFR3-Ig specifically blocks binding of BAFF/BLyS to its cognate receptor BAFFR3, resulting in systemic reduction in B cell numbers in lymphoid organs (See Kayagaki, N., et al., BAFF/BLyS receptor 3 binds the B cell survival factor BAFF ligand through a discrete surface loop and promotes processing of NF-kappaB2. Immunity, 2002. 17(4): p. 515-24). Treatment was initiated in a late-prophylactic mode (7 days after IFNα adenovirus). Specifically, (NZB x NZW)F1 mice (The Jackson Laboratory), 13-15 wk old, were injected with a single intravenous dose of IFN-α adenovirus (Abbott) at a concentration of 5×10$^9$ viral particles/mouse. Treatment groups consisted of administration of Compound 1 in doses ranging from 1-100 mg/kg/day, given orally; mycophenolate mofetil (MMF) at a dose of 100 mg/kg/day, given orally; and BAFFR3-Ig (BAFF/BLyS blocker) at a dose of 15 mg/kg, 3×/week, by intraperitoneal injection. All treatment groups were administered treatment 7 days after adenovirus injection. Following adenovirus injection, mice were monitored weekly for proteinuria (PU) using Albustix test strips (VWR). Severe PU was defined by consecutive weekly measurements of PU≥300 mg/dl. When mice became moribund, they were sacrificed according to Institutional Animal Care and Use Committee protocols.

Figure 9:
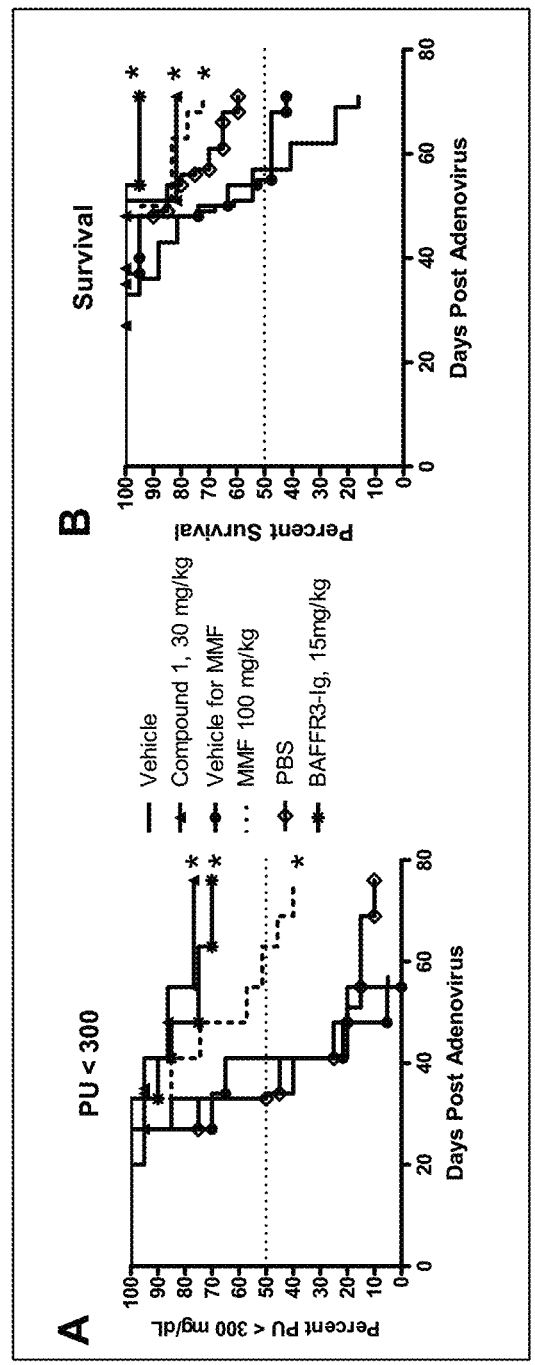
FIG. 9 illustrates the efficacy of treatment with a selective Bcl-2 inhibitor (Compound 1), MMF and BAFFR3-Ig in an IFNα-induced SLE model as assessed by (A) incidence of severe proteinuria (PU≥300 mg/dL) and (B) Kaplan-Meier cumulative survival. Asterisks represent a statistical significance of P<0.05.

The results of this experiment are illustrated in FIG. 9, and Table 4 below. Consistent with the finding in spontaneous lupus mice, treatment with both 30 and 100 mg/kg of Compound 1 significantly delayed the onset of severe PU and prolonged survival. The efficacy was comparable to, if not better than, MMF and BAFFR3-Ig, and correlated with sustained lymphopenia. The target efficacious exposure was approximately 40 μg·h/mL.

TABLE 4

| PU and Survival Efficacy in Compound 1, MMF and BAFF-R3-Ig Treated Animals | | |
|---|---|---|
| Treatment Groups | % Mice with PU < 300 mg/dL | % Survival |
| Compound 1 | | |
| Vehicle Control | 0 | 16 |
| 30 mg/kg | 77* | 82* |
| MMF | | |
| Vehicle Control | 0 | 42 |
| 100 mg/kg | 40* | 72* |
| BAFFR3-Ig | | |
| PBS | 10 | 60 |
| 15 mg/kg | 70* | 95* |

*P < 0.05

Example 8

Effect of Selective Bcl-2 Inhibitors on Anti-Ds DNA Titer in Interferon-α Accelerated Lupus Model An additional experiment was performed to determine the effects of treatment with a selective Bcl-2 inhibitor on anti-DS DNA titer in the Interferon-a accelerated lupus model. Anti-dsDNA antibody levels were measured by ELISA and assigned arbitrary activity unit concentrations per ml relative to a standard plasma pool derived from proteinuric 9-10 month old NZBW mice. ELISA assay was performed by coating plates with poly-L-lysine followed by calf-thymus DNA. Diluted mouse plasma was incubated and developed using anti-IgG HRP conjugated antibodies and the mean OD from duplicate wells was compared to a titrated standard curve of pooled high tittered anti-dsDNA plasma. The undiluted standard plasma pool was arbitrarily assigned a value of 1000 anti-dsDNA Units/ml. A linear regression analysis was then used to calculate the relative units of a given sample multiplied by the given dilution factor. The results of this experiment are illustrated in FIG. 10.

Figure 10:
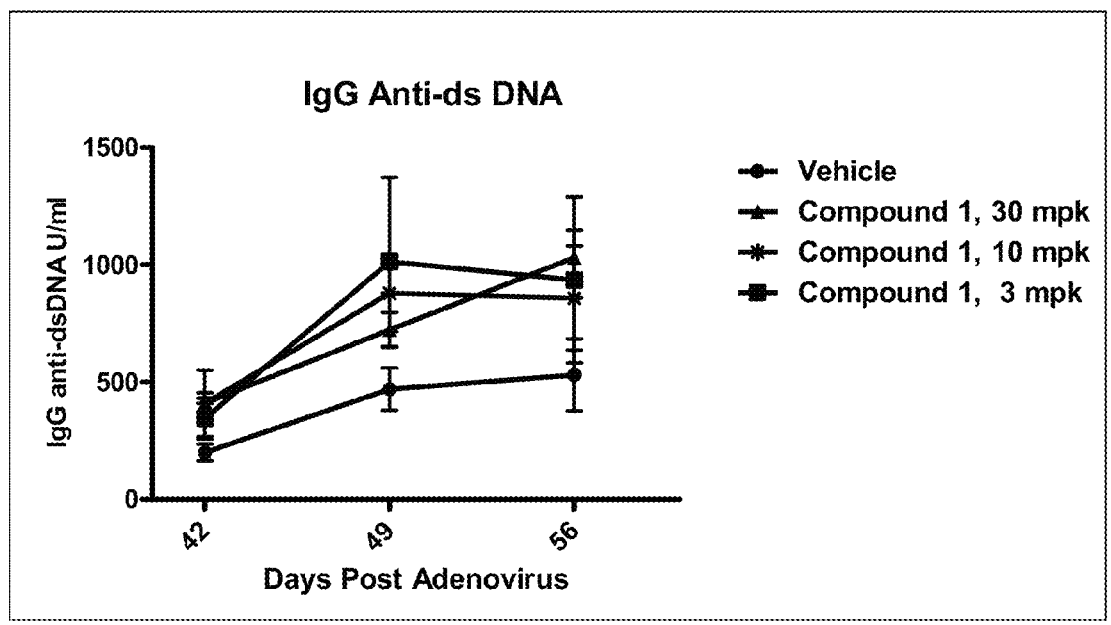
FIG. 10 illustrates anti-ds DNA production in IFNα-induced (NZBxNZW)F1 mice treated with a selective Bcl-2 inhibitor (Compound 1), at doses ranging from 3-30 mg/kg, compared to vehicle control, as evidenced by Immunoglobulin G (IgG) levels.

In contrast to the findings from the spontaneous (NZB× NZW)F1 mice model, illustrated in FIG. 5, Compound 1 did not significantly inhibit anti-ds DNA titer in the interferon-induced model, as shown in FIG. 10. There was a 2 fold but non-statistically significant induction of anti-ds DNA titer between day 42 and 55, which was not dose dependent. It should be noted that at 30 mg/kg, Compound 1 treatment of these animals maintained a >70% lymphopenia in the blood throughout treatment and protected the animals from lupus nephritis.

Example 9

Infiltration of Selective Bcl-2 Inhibitors into the Salivary Glands

It is recognized within the art that Sjogren's Syndrome is a chronic disease state that affects the moisture-producing glands of the body, including the salivary glands of the mouth. As such, it was theorized that penetration of the selective Bcl-2 inhibitors into the salivary glands of patients with Sjogren's Syndrome could provide an effective treatment to decrease lymphocytes associated with Sjogren's Syndrome, without the dose-limiting thrombocytopenia associated with non-selective Bcl-2 inhibition. A histologic assessment of the penetration of selective Bcl-2 inhibitors into the salivary glands of spontaneous murine model for lupus was performed to test this theory. The spontaneous murine model of lupus, as described in Example 3, was used for the histological assessment described herein. Specifically, sublingual and submandibular salivary glands were fixed in 10% neutral-buffered formalin and paraffin embedded. Five μm sections were H&E stained and semiquantitatively scored (0-4) by an experienced pathologist for inflammatory cell infiltrates. Salivary gland infiltrate scoring categories: (1) 3 or fewer small periductular foci, (2) 3 or more medium sized foci, (3) several extensive foci, and (4) coalescing to diffuse infiltrates. The histologic assessment of the submandibular tissue sections is illustrated in FIG. 11.

Figure 11:
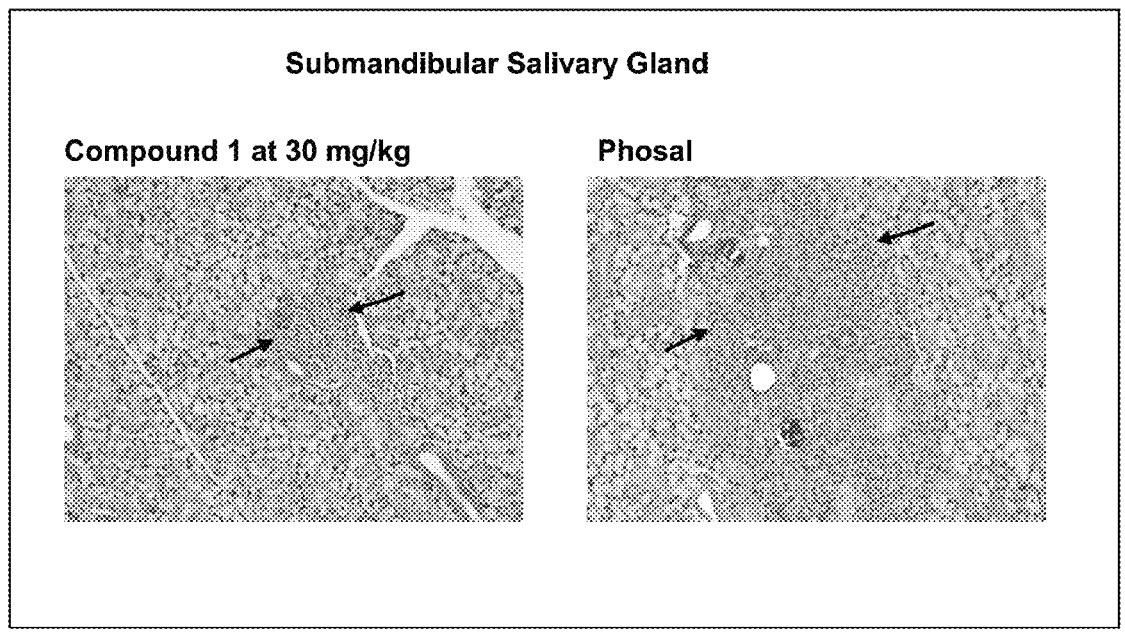
FIG. 11 illustrates representative images demonstrating the reduction of periductular infiltrates in the submandibular salivary gland of spontaneous murine model mice treated with a selective Bcl-2 inhibitor (Compound 1), with a magnification 200×.
Figure 12:
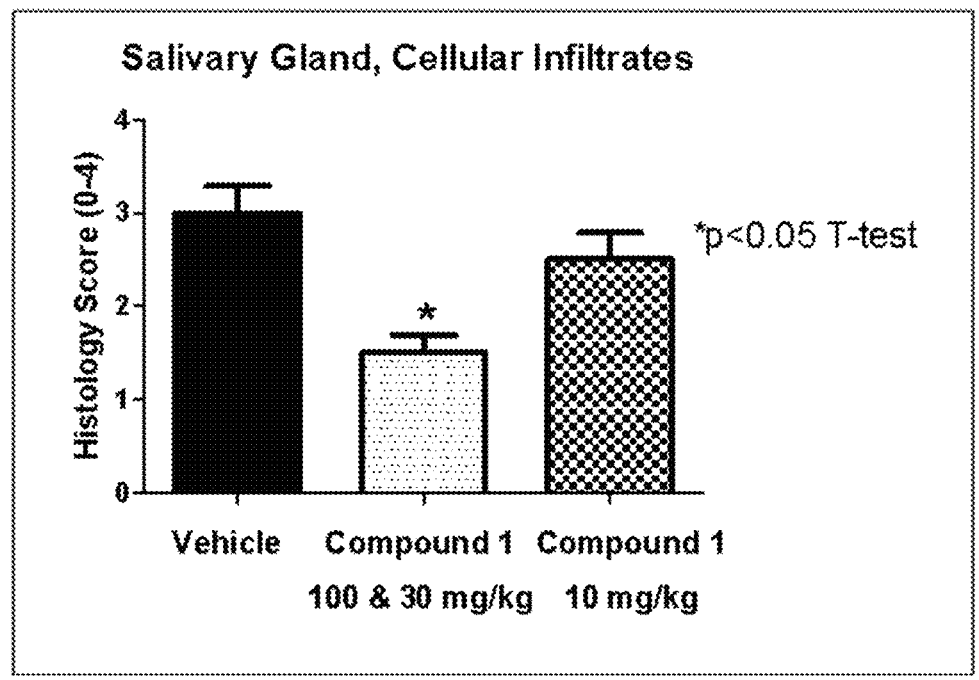
FIG. 12 illustrates the histology scores for submandibular salivary gland tissue treated with one of three treatment regimens: treatment with a phosal vehicle, treatment with a selective Bcl-2 inhibitor (Compound 1) at a dose of 10 mg/kg; and treatment with Compound 1 at a dose of 30 mg/kg and 100 mg/kg.

As illustrated in FIG. 11, phosal vehicle dosed spontaneous lupus nephritis mice typically had extensive to coalescing periductular infiltrates. Salivary gland infiltrates in spontaneous lupus nephritis mice dosed with 30 or 100 mg/kg of Compound 1 were small, discrete and less frequent. In addition, FIG. 12 includes a bar graph illustrating the difference in histology scores for submandibular tissue that was not treated, tissue treated with Compound 1 at a dose of 10 mg/kg, and tissue treated with Compound 1 at doses of 30 mg/kg and 100 mg/kg. As noted in FIG. 11, the tissue treated with Compound 1 at doses of 30 mg/kg and 100 mg/kg illustrated histology scores showed a statistically significant improvement in histology scores, as evidenced by the fact that the histology scores for 30 mg/kg and 100 mg/kg treatment were less severe.

Accordingly, Sjogren's Syndrome is an inflammatory disease that affects the moisture-producing glands of the body, including the salivary gland. Histologic assessment of salivary glands in spontaneous murine models was performed to determine if treatment with a selective Bcl-2 inhibitor could decrease the inflammatory processes in the salivary gland, and ultimately provide a treatment option for Sjogren's Syndrome. The histological assessment showed that doses of 30 mg/kg and 100 mg/kg of Compound 1 resulted in decreased inflammation in the salivary glands, as evidenced by an improvement in the histology score from 3-4 in mice that were not treated to a score of 1-2 in mice that were treated. Thus, it was determined that selective Bcl-2 inhibitors may provide an effective treatment for patients with Sjogren's Syndrome.

What is claimed is:

1. A method of treating systemic lupus erythematosus and lupus nephritis in a patient, said method comprising administering to the patient a therapeutically effective amount of a compound selected from 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide or a pharmaceutically acceptable salt thereof and 4-(4-{[2-(4-chlorophenyl)-4,4-dimethylcyclohex-1-en-1-yl]methyl}piperazin-1-yl)-N-[(4-{[(trans-4-hydroxy-4-methylcyclohexyl)methyl]amino}-3-nitrophenyl)sulfonyl]-2-(1H-pyrrolo[2,3-b]pyridin-5-yloxy)benzamide or a pharmaceutically acceptable salt thereof.

2. A method of treating Sjogren's Syndrome in a patient, said method comprising administering to the patient a therapeutically effective amount of a compound selected from 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide or a pharmaceutically acceptable salt thereof and 4-(4-{[2-(4-chlorophenyl)-4,4-dimethylcyclohex-1-en-1-yl]methyl}piperazin-1-yl)-N-[(4-{[(trans-4-hydroxy-4-methylcyclohexyl)methyl]amino}-3-nitrophenyl)sulfonyl]-2-(1H-pyrrolo[2,3-b]pyridin-5-yloxy)benzamide or a pharmaceutically acceptable salt thereof.

3. The method of claim 1 wherein the therapeutically effective amount of the compound is between 0.01 mg/kg and 500 mg/kg.

4. The method of claim 1 wherein the therapeutically effective amount of the compound is between 0.1 mg/kg and 300 mg/kg.

5. The method of claim 1 wherein the therapeutically effective amount of the compound is between 1 mg/kg and 100 mg/kg.

6. The method of claim 1 wherein the compound is 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide or a pharmaceutically acceptable salt thereof.

7. The method of claim 1 wherein the compound is 4-(4-{[2-(4-chlorophenyl)-4,4-dimethylcyclohex-1-en-1-yl]methyl}piperazin-1-yl)-N-[(4-{[(trans-4-hydroxy-4-methylcyclohexyl)methyl]amino}-3-nitrophenyl)sulfonyl]-2-(1H-pyrrolo[2,3-b]pyridin-5-yloxy)benzamide or a pharmaceutically acceptable salt thereof.

8. The method of claim 2 wherein the therapeutically effective amount of the compound is between 0.01 mg/kg and 500 mg/kg.

9. The method of claim 2 wherein the therapeutically effective amount of the compound is between 0.1 mg/kg and 300 mg/kg.

10. The method of claim 2 wherein the therapeutically effective amount of the compound is between 1 mg/kg and 100 mg/kg.

11. The method of claim 2 wherein the compound is 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide or a pharmaceutically acceptable salt thereof.

12. The method of claim 2 wherein the compound is 4-(4-{[2-(4-chlorophenyl)-4,4-dimethylcyclohex-1-en-1-yl]methyl}piperazin-1-yl)-N-[(4-{[(trans-4-hydroxy-4-methylcyclohexyl)methyl]amino}-3-nitrophenyl)sulfonyl]-2-(1H-pyrrolo[2,3-b]pyridin-5-yloxy)benzamide or a pharmaceutically acceptable salt thereof.

* * * * *